(12) United States Patent
Lukehart et al.

(10) Patent No.: US 6,232,264 B1
(45) Date of Patent: May 15, 2001

(54) POLYMETALLIC PRECURSORS AND COMPOSITIONS AND METHODS FOR MAKING SUPPORTED POLYMETALLIC NANOCOMPOSITES

(75) Inventors: Charles M. Lukehart, Nashville, TN (US); William D. King, Aiken, SC (US); Stephen B. Milne, Wayne, NJ (US); Frank E. Jones, III, Antioch, TN (US); James D. Corn, Nashville, TN (US); Deborah L. Boxall, Franklin, TN (US); Krzysztof C. Kwiatkowski, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/099,556

(22) Filed: Jun. 18, 1998

(51) Int. Cl.$^7$ ..................................................... B01J 23/42
(52) U.S. Cl. ........................................... 502/339; 502/150
(58) Field of Search .................................. 502/326, 150, 502/339

(56) References Cited

U.S. PATENT DOCUMENTS

| | | | |
|---|---|---|---|
| 4,081,409 | | 3/1978 | McNicol et al. . |
| 4,590,288 | * | 5/1986 | Klemann ............................ 556/112 |
| 4,609,639 | * | 9/1986 | Braunstein et al. ................. 502/326 |
| 4,937,220 | * | 6/1990 | Nickols, Jr. ......................... 502/185 |
| 5,277,789 | * | 1/1994 | Kounaves et al. ................... 205/238 |
| 5,489,563 | * | 2/1996 | Brand et al. ......................... 502/185 |
| 5,589,537 | * | 12/1996 | Golden et al. ....................... 524/780 |
| 5,767,036 | * | 6/1998 | Freund et al. ....................... 502/185 |
| 5,789,027 | * | 8/1998 | Watkins et al. ..................... 427/250 |
| 5,922,488 | * | 7/1999 | Marucchi-Soos et al. ............ 429/44 |
| 5,939,220 | * | 8/1999 | Gunner et al. ...................... 429/40 |

FOREIGN PATENT DOCUMENTS 2657726   9/1977   (DE) .

OTHER PUBLICATIONS

Lorenson et al., "The Effect of Particle Size on Microwave Heated Carbon and the Subsequent Crystallite Growth", from Sutton, ed., "Microwave Processing of Materials III", *Materials Research Society*, Symposium Proceedings, vol. 269, pp. 129–135 (1992).

King, et al., "Synthesis of a heteronuclear cluster containing Pt, Ru and Hg and the preparation of carbon–supported metal nanoparticles from this molecular precursor," Book of Abstracts, 215th ACS National Meeting, Mar. 29–Apr. 2, 1998, abstract.*

S. Galema, "Microwave Chemistry", *Chem. Soc. Reviews*, vol. 26, (1997), pp. 233–238.

M.S. Nasher et al., "Structural Characterization of Carbon–Supported Platinum–Ruthenium Nanoparticles from the Molecular Cluster Precursor PtRu$_5$C(CO)$_{16}$", *J. Am. Chem. Soc.*, 119, pp. 7760–7771 (Aug. 20, 1997).

W.–F. Lin et al., "One–Line FTIR Spectroscopic Investigations of Methanol Oxidation in a Direct Methanol Fuel Cell", *J. Electrochem. Soc.*, vol. 144, No. 6 (Jun. 1997), pp. 1917, 1922.

A. Hamnett, "Mechanism and Electrocatalysis in the Direct Methanol Fuel Cell", *Catalysis Today*, 38 (1997) pp. 445–457.

T.R. Ralph, "Proton Exchange Membrane Fuel Cells, Progress In Cost Reduction Of the Key Components", *Platinum Metals Rev.*, 41(3) (1997) pp. 102–113.

G.K. Chandler et al., "Electrodes Based On Noble Metals, Essential Components For Electrochemical Technology", *Platinum Metals Rev.*, 41(2) (1997), pp. 54–63.

Naomi Nallas et al., "Bipyrimidine–Bridged Mixed–Metal Trimetallic Complexes of Ruthenium (II) With Rhodium (III) or Iridium (III), $\{[(bpy)_2Ru(bpm)]_2MCl_2\}^{5+}$", *Inorg. Chem.*, 35 (1996), pp. 6974–6980.

Lukehart et al., "Nanocomposites Containing Nanoclusters Of Selected First–Row Transition metal Phosphides", *ACS Symposium*, Chapter 13, 622:195 (1996), pp. 195–204.

G.A. Pathanjali et al., "Methanol–Air Fuel Cell", *Bull. Electrochemistry*, 12 (3–4) (Mar.–Apr. 1996), pp. 193–195.

Iskander et al., ed., "Microwave Processing of Materials V", *Materials Research Society Symposium Proceedings*, vol. 430 (1996), Table of Contents, pp. v–xiii.

R.R. Di Fiore et al., "Microwave Processing of Redox Ceramic–Metal Composites", *Mat. Res. Soc. Symp. Proc.*, vol. 430 (1996), pp. 101–106.

M. Gonzalez et al., "Microwave Processing Applied to Ceramic Reactions", *Mat. Res. Soc. Symp. Proc.*, vol. 430 (1996), pp. 107–112.

(List continued on next page.)

*Primary Examiner*—Tom Dunn
(74) *Attorney, Agent, or Firm*—Akin, Gump, Strauss, Hauer & Feld, L.L.P.

(57) ABSTRACT

The present invention relates to methods for preparing polymetallic precursors and for preparing improved nanocomposites formed from such precursors which are useful in fuel cell catalyst compositions. The nanocomposites include a support and a plurality of polymetallic nanoparticles with a selected metal atomic ratio. The metals in the polymetallic precursors have a stoichiometric ratio which is approximately equal to the selected atomic ratio of metals in the nanoparticles such that stoichiometric control is provided for the resulting nanocomposite catalyst. Crystalline intermetallic or metal alloy nanoparticles form when a polymetallic precursor having a particular metal stoichiometry is contacted with a conductive support, and the precursor is thermally degraded on the support leading to retention of the metal core of the precursor on the support. The polymetallic alloy nanoparticles formed have a selected metal atomic ratio which is approximately equal to the stoichiometric ratio of metals in the polymetallic precursor. Fuel cell catalysts comprising such nanocomposites have utility as either anode or cathode fuel cell catalysts, particularly in DMFCs.

26 Claims, 12 Drawing Sheets

OTHER PUBLICATIONS

I. Gomez et al., "Kinetics of Reduction of Iron Oxides Using Microwaves as Power Source", *Mat. Res. Soc. Symp. Proc.*, vol. 430 (1996), pp. 423–428.

X. Ren et al., "High Performance Direct Methanol Polymer Electrolyte Fuel Cells", *J. Electrochem. Soc.*, vol. 143, No.l 1 (Jan. 1996), pp. L12–L15.

K. Wang et al., "On the Reaction Pathway For Methanol and Carbon Monoxide Electrooxidation on Pt–Sn Alloy Versus Pt–Ru alloy Surfaces", *Electrochimica Acta*, vol. 41, No. 16, (1996), pp. 2587–2593.

J. Carpenter et al., "Di– and Polynuclear Complexes As Precursors To Nanocomposite Materials: An Overview", *Inorganica Chimica Acta*, 251 (1996), pp. 151–156.

M.P. Hogarth et al., "Direct Methanol Fuel Cells, Technological Advances and Further Requirements", *Platinum Metals Rev.* 40 (4) (1996), pp. 150–159.

J.P. Carpenter et al., "Nanocomposites From Molecularly Doped Silica Xerogels: An Overview", *27th International SAMPE Technical Conference*, Oct. 9–12 (1995), pp. 549–559.

K. Severin et al., "Heterobimetallic Chloro Bridged Complexes of $(\eta^3:\eta^3-C_{10}H_{16})$–ruthenium(IV) with palladium(II), platinum(II), rhodium (III), iridium(III), copper (I) and rhodium(I)", *Inorganica Chimica Acta* 240 (1995), pp. 339–346.

M.P. Hogarth et al., "Electrooxidation of Methanol On Carbon Supported Finely Dispersed Pt–Ru Catalyst", *Proceedings of First International Symp. New Mater. Fuel Cells* (1995) pp. 310–325.

A.G. Whittaker et al., "Microwave–Assisted Solid–State Reactions Involving Metal Powders", *J. Chem. Soc. Dalton Trans.* (1995) pp. 2073–2079.

V. Radmilović et al., "Structure and Chemical Composition of a Supported Pt–Ru Electrocatalyst for Methanol Oxidation", *J. of Catalysis* 154 (1995), pp. 98–106.

J.P. Carpenter et al., "Formation of a Nanocomposite Containing Particles of $Co_3C$ from a Single–Source Precursor Bound to a Silica Xerogel Host Matrix", *Chemistry of Materials* 7 (1995) pp. 201–205.

S. Surampudi et al., "Advances in Direct Oxidation Methanol Fuel Cells", *J. of Power Sources*, 47 (1994), pp. 377–385.

M. Iskander et al., ed., "Microwave Processing of Materials IV", *Materials Research Society Symposium Proceedings*, vol. 347 (Apr. 4–8, 1994) Table of Contents, pp. v–xi.

G.A. Kriegsmann et al., "Microwave Heating of Carbon Coated Ceramic Fibers", *Mat. Res. Soc. Symp. Proc.*, vol. 347 (1994), pp. 579–584.

D.E. Clark et al., "Microwave Processing At the University of Florida", *Mat. Res. Soc. Symp. Proc.*, vol. 347 (1994), pp. 489–500.

H.Y. Kim et al., "Calcination of Metal Oxide/Activated Carbon Catalysts Under Electromagnetic Fields", *Mat. Res. Soc. Symp. Proc.*, (1994) pp. 507–512.

H.A. Gasteiger et al., "Temperature Dependent Methanol Electro–Oxidation on Well–Characterized Pt–Ru Alloys", *J. Electrochem. Soc.*, vol. 141, No. 7 (Jul. 1994), pp. 1795–1803.

H.A. Gasteiger et al., "Methanol Electrooxidation on Well–Characterized Pt–Ru Alloys", *J. Phys. Chem.*, 97 (1993) pp. 12020–12029.

A.G. Whittaker et al., "Microwave–assisted Solid State Reactions Involving Metal Powders and Gases", *J. Chem. Soc. Dalton Trans.* (1993), pp. 2541–2543.

A.G. Whittaker et al., "Microwave–assisted Sold–state Reactions Involving Metal Powders", *J. Chem. Soc. Dalton Trans.* (1992), pp. 2751–2752.

R. Srinivasan et al., "X–ray Diffraction and Electron Microscopy Studies of Platinum–Tin–Silica Catalysts", *Applied Catalysis A: General*, 87 (1992) pp. 45–67.

A. Hamnett et al., "Electrocatalysis and the Direct Methanol Fuel Cell", *Chem. and Industry*, 480, No. 13 (1992), 4 pages.

R.L. Beatty et al., ed., "Microwave Processing of Materials III", *Materials Research Society Symposium Proceedings*, vol. 269 (Apr. 27–May 1, 1992), Table of Contents, pp. v–xi.

C.P. Lorenson et al., "The Effect of Particle Size on Microwave Heated Carbon and the Subsequent Crystallite Growth", *Mat. Res. Soc. Symp. Proc.*, vol. 269 (1992), pp. 129–135.

R. Srinivasan et al., "The Structure of Platinum–Tin Reforming Catalysts", *Plat. Metals. Rev.*, 36, No. 3, (1992), pp. 151–163.

M. Ichikawa, "Metal Cluster Compounds as Molecular Precursors for Tailored Metal Catalysts", D. Eley et al., ed., *Advances in Catalysis*, vol. 38, (1992) pp. 283–296.

A.N. Haner, "The Surface Structure and Composition of <111> and <100> Oriented Single Crystals of the Ordered Alloy $Pt_3Sn$", *Surface Science*, 249 (1991) pp. 15–20.

B. Brietscheidel, "Metal Complexes in Inorganic Matrices. 7. Nanometer–Sized, Uniform Metal Particles in a $SiO_2$ Matrix by Sol–Gel Processing of Metal Complexes", *Chem. Mater.*, 3 (1991), pp. 559–566.

C.N. Satterfield, *Heterogeneous Catalysis in Industrial Practice*, 2d ed., "Table of Contents", pp. v–xi "Chapter 4: Catalyst Preparation and Manufacture", pp. 87–130 and "Chapter 6: Supported Metal Catalysts", pp. 175– (1991).

T.P. Chojnacki et al., "Microstructures of Pt–Sn and Rh–Sn Particles on $SiO_2$", *J. of Catalysis*, 129 (1991), pp. 473–485.

R.Srinivasan et al., "Electron Microdiffraction Study of Pt–Sn–Alumina Reforming Catalysts", *J. of Catalysis* 129 (1991), pp. 257–268.

N.C. Payne, "Synthesis, Structure, and Reactivity of $Pt_3Au$ and $Pt_3Au_2$ Cluster Complexes", *J. Inorganic Chem.*, vol. 30, (1991), pp. 4052–4056.

B.E. Handy et al., "Morphologies of Sn and Pt–Sn Phases on Thin films of Alumina and Graphite", *J. of Catalysis* (1990), pp. 160–182.

M.C. Jennings, "Synthesis, Structure, and Reactivity of cluster Complexes Containing the $Pt_3(\mu_3-Sn)$ Unit and a Possible Relationship to Heterogeneous Platinum–Tin Catalysts", *Organometallics*, 10 (1991) pp. 580–586.

L. Liu et al., "Quantum–Dot Size–Distribution Analysis and Precipitation Stages in Semiconductor Doped Glasses", *J. Appl. Phys.*, 68 (1) (Jul. 1, 1990), pp. 28–32.

L.L. Hench et al., "The Sol–Gel Process", *Chem. Rev.*, 90 (1990), pp. 33–72.

W.H. Sutton, "Microwave Processing of Ceramic Materials", *Ceramic Bull.*, vol. 68, No. 2 (1989), pp. 376–386.

W.H. Sutton et al., ed., "Microwave Processing of Materials", *Materials Research Society Symposium Proceedings*, vol. 124 (Apr. 5–8, 1988), Table of Contents, pp. v–x.

A.K. Thorsrud, "Dielectric Heating Sensitizers for Processing of Polymers", *Mat. Res. Soc. Symp. Proc.*, vol. 124 (1988), pp. 195–200.

A. Hamnett et al., "Bimetallic Carbon Supported Anodes for the Direct Methanol–Air Fuel Cell", *J. Electrochimica Acta*, vol. 33, No. 11, pp. 1613–1617 (1988).

M. Watanabe et al., "Preparation of Highly Dispersed Pt + Ru Alloy Clusters and the Activity for the Electrooxidation of Methanol", *J. Electroanal. Chem.*, 229 (1987) pp. 395–406.

J. Venter et al., "Carbon–Supported Fe–Mn and K–Fe–Mn Clusters for the Synthesis of $C_2$–$C_4$ Olefins from CO and $H_2$, 1. Chemisorption and Catalytic Behavior", *J. of Catalysis*, 103 (1987), pp. 450–465.

R. Sahai et al., "A Ruthenium (II)/Platinum(II) Binuclear Complex Bridged by 2,2'–Bipyrimidine", *Inorganica Chimica Acta*, 118 (1986), pp. L35–L37.

R. Sahai et al., "A Novel Hetero–oligomer Containing One Ruthenium (II) and Three Platinum (II) Metal Centres Bridged by 2,3–bis(2–pyridyl)quinoxaline", *J. Chem. Soc., Chem. Commun.* (1986), pp. 1133–1134.

G. Ferguson et al., "A Platinum Cluster Complex Containing a Triply Bridging Carbonyl: The Synthesis and Structure of ($\mu_3$–Carbonyl)tris[$\mu$–bis(dipheylphosphino)methane]–triangulo–triplatinum(2+) Hexafluorophosphate", *Organometallics*, 5 (1986), pp. 344–348.

M. Kaminsky et al., "Carbon–Supported Fe–Ru Catalysts Prepared from Stoichiometric Mixed–Metal Carbonyl Clusters", *J. of Catalysis*, 91 (1985), pp. 338–351.

R. Hemmerich et al., "Anchoring of Hydridic Clusters by Acid–Base Reactions: New Method for the Preparation of Highly Active Fischer—Tropsch Catalysts" *J. Chem. Soc., Chem. Commun.*, (1983), pp. 428–430.

V. Ponec, "Catalysis by Alloys in Hydrocarbon Reactions", D. Eley et al, eds., *Advances in Catalysis*, vol. 32 (1983), pp. 149–150, 205 and Table of Contents, pp. v–vii (1983).

Y.I. Yermikov, "Supported Catalysts Obtained by Interaction of Organometallic Compounds of Transition Elements with Oxide Supports", *Catal. Rev.–Sci. Eng.*, 13(1) (1976), pp. 77–120.

B.D. McNichol et al., "Pt/Sn Bimetallic Catalysts for the Electro–Oxidation of Methanol: Poisoning by Silicate and Phosphate Anions", *J. of Appl. Electrochem.*, 6 (1976), pp. 221–227.

B.D. McNichol et al., "Methanol Electro–Oxidation Catalysts, Platinum Promoted by Tin", *J. Chem. Soc. Faraday I*, 72 (1976), pp. 2735–2737 and 2742–2743.

M.R. Andrew et al., "The Characterization of Pt/Sn Catalyst for the Electrochemical Oxidation of Methanol", *J. of Applied Electrochemistry* 6 (1976), pp. 99–106.

K.J. Cathro, "The Oxidation of Water–Soluble Organic Fuels Using Platinum–Tin Catalysts", *J. Electrochem. Soc.: Electrochem. Tech.*, vol. 116, No. 11 (Nov. 1969), pp. 1608–1611.

K.J. Cathro, "The Use of Platinum–Rhenium Catalysts for the Oxidation of Aqueous Methanol", *J. Electroch. Tech.* (Sep.–Oct. 1967), pp. 441–445.

H.P. Klug, *X–Ray Diffraction Procedures for Polycrystalline and Amorphous Materials*, 2d ed., (1974), Table of Contents, pp. xiii–xxv.

A.J. Appleby, *Fuel–Cell Handbook* (1989), Table of Contents, pp. xiii–xxi.

C.J. Brinker et al., *Sol–Gel Science: The Physics and Chemistry of Sol–Gel Processing* (1990), Table of Contents, pp. vii–x.

W.R. Moser, ed., *Advanced Catalysts and Nanostructured Materials, Modern Synthetic Methods*, (1996), Table of Contents, pp. v–xviii.

J.H. Sinfelt, *Bimetallic Catalysts, Discoveries, Concepts, and Applications* (1983) Table of Contents, pp. xi.

A.B. Stiles, *Catalyst Supports and Supported Catalysts, Theoretical and Applied Concepts*, Table of Contents, pp. v–vii (no date).

* cited by examiner

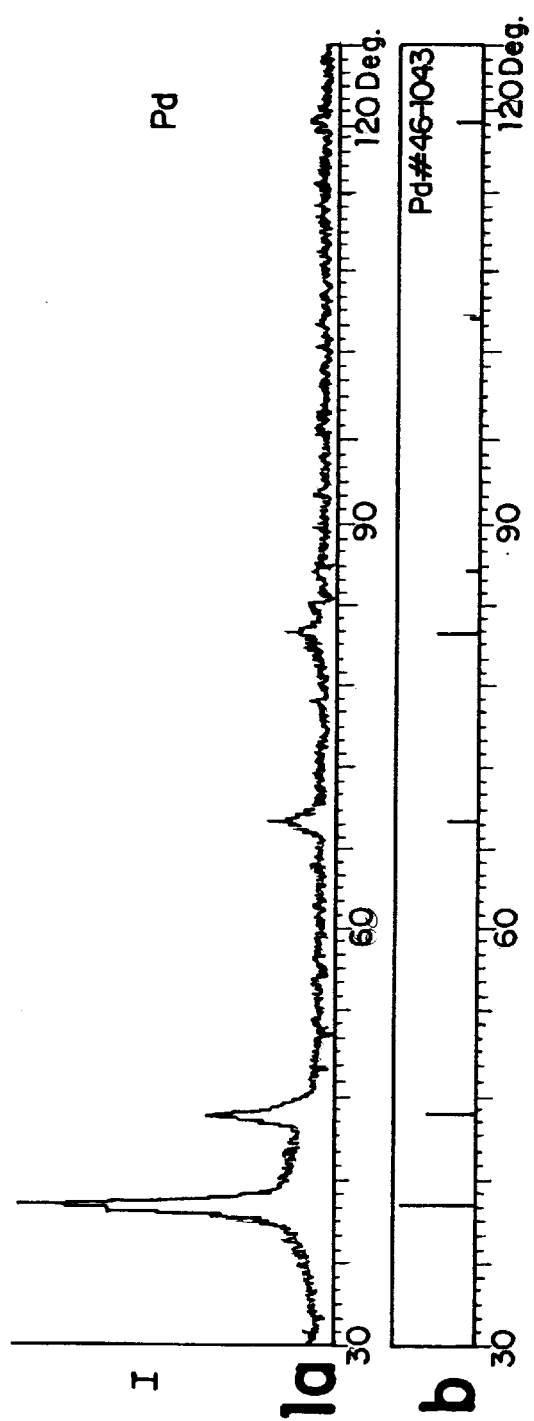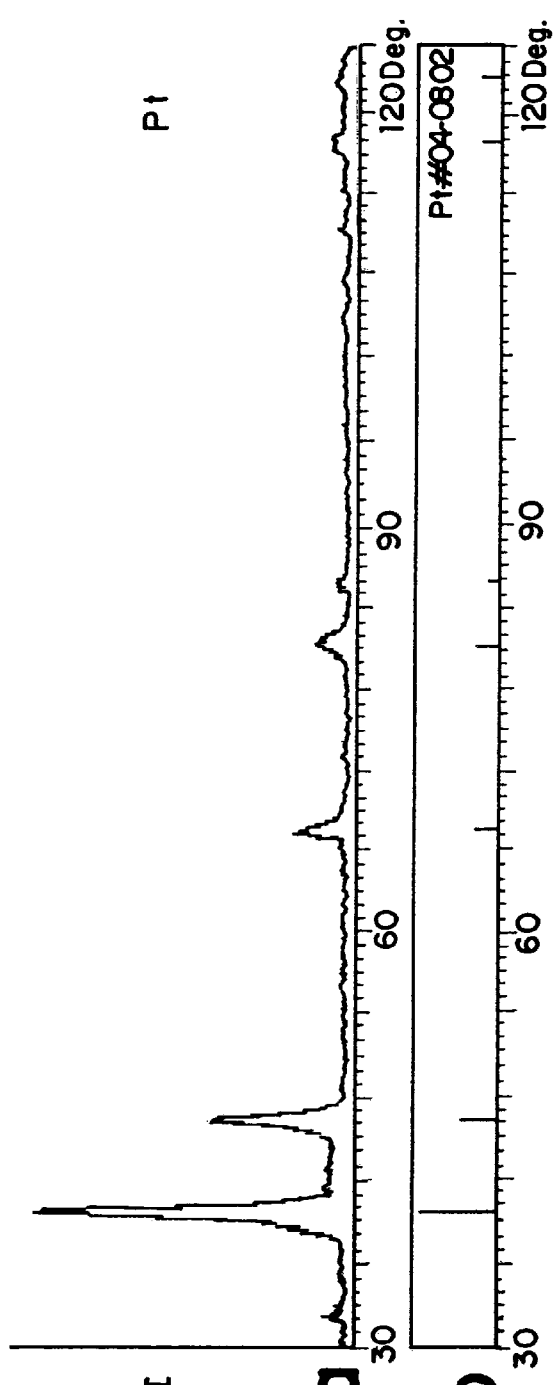
FIG.11a FIG.11b FIG.12a FIG.12b

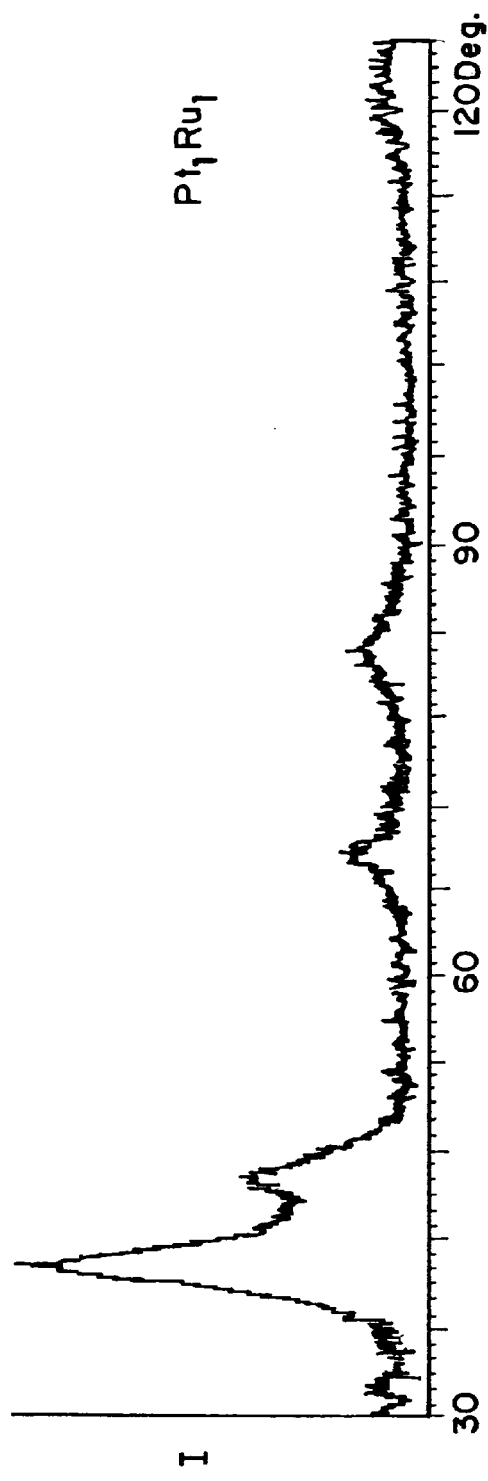
FIG. 13
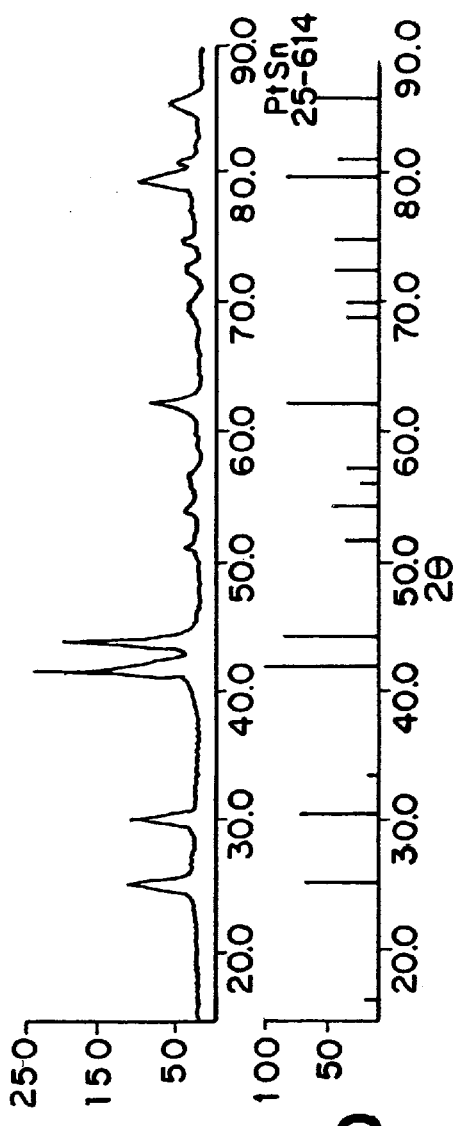
FIG.14a
FIG.14b

POLYMETALLIC PRECURSORS AND COMPOSITIONS AND METHODS FOR MAKING SUPPORTED POLYMETALLIC NANOCOMPOSITES

STATEMENT REGARDING FEDERALLY SPONSORED RESEARCH OR DEVELOPMENT

This research was supported in part by U.S. Government funds by the Army Research Office (U.S. Army grants numbers DAAH04-95-0146, DAAH04-96-1-0179, and DAAH04-96-1-0302), and the U.S. Government may therefore have certain rights in the invention.

BACKGROUND OF THE INVENTION

Nanocomposites comprise very small particles typically having diameters less than 100 nm deposited on the surface of a support or within a host matrix. In recent years, nanocomposites have become a topic of great interest. When the particles are metal particles, the nanocomposites exhibit interesting electronic and nonlinear optical properties. When the particles are metallic with a high surface area, the nanocomposites exhibit high chemical reactivity as catalysts for a variety of chemical reactions. The average diameter of metallic nanoparticles usually can be controlled by varying annealing conditions or by metal loading. Generally, nanoparticle diameter can be increased by using high-temperature annealing. Various support matrices for nanocomposites may be chosen for various chemical uses. For example, the matrix may be porous and/or conductive for various catalytic applications, or for optical applications, a transparent matrix may be useful.

A fuel cell directly converts chemical energy of fuel and oxidant reactants into low-voltage direct current by means of electrode-catalyzed electrochemical reactions. However, unlike conventional batteries, fuel cells do not consume the materials comprising the electrodes. In a fuel cell system, the cell converts chemical energy into electricity without undergoing irreversible chemical change to the cell. Provided the catalyst remains active, a fuel cell can operate as long as it has a source of fuel and oxidant, and the reaction products are removed.

A fuel cell performs the same function as a galvanic cell or a discharging storage battery. However, in a fuel cell, the reactants are stored outside the reaction areas. The reactants are provided to the electrodes only when power generation is required. The oxidizing reactant in most fuel cells is atmospheric oxygen. When a fuel cell runs out of a reactant, generation of electricity ceases. Power generation resumes when the reactant is provided to the system.

A fuel cell comprises a fuel electrode (anode) and an oxidant electrode (cathode) separated by an ion-conducting electrolyte. The electrodes are conductively connected through a load by an external electronic circuit. The electric current is transported by the flow of electrons in the conductive part of the circuit. A simple hydrogen-oxygen fuel cell has the theoretical potential of generating direct current at a voltage up to 1.229 V at standard temperature and pressure.

The first successful fuel cells resulted from research conducted as a part of the United States aerospace program in the mid-1960's. By around 1970, several problems with fuel cells had become apparent. One problem was identifying a fuel that was efficient enough for practical use. Gaseous hydrogen was the only fuel that fell into this category. Hydrocarbons and alcohols had insufficient reactivity with even the most active catalysts, and other fuels, such as hydrazine, were not commercially feasible. Another problem with such fuel cells was that, for fuel cells constructed with aqueous electrolytes capable of handling reformed hydrocarbons, the only effective catalysts were expensive noble metal catalysts, such as platinum or palladium catalysts having relatively high loadings (about 25 mg/cm$^2$ of noble metal). Because of the high cost, widespread commercial use of these noble metal catalysts was not practical. A third problem was the lifetime of the catalysts, which was initially only in the hundreds of hours, owing to catalyst degradation.

The energy crisis in 1974 and environmental concerns over fossil fuel related pollution awakened interest in fuel cell research. The products generated by fuel cells are less environmentally harmful than the products generated by combustion of fossil fuels. More recently, better understanding of electrocatalysis and improved techniques of catalyst preparation have made it possible to use electrodes having much lower platinum loadings without compromising fuel cell performance. As a result of this renewed research, catalyst loadings have been reduced to as low as 0.5 mg/cm$^2$ of noble metal or less for hydrogen/oxygen fuel cells. Also, recovering and recycling fuel cell catalysts is now possible. Lifetimes of fuel cell electrode catalysts have also been greatly increased, from hundreds of hours to more than 50,000 hours.

Currently, many different aspects of fuel cell chemistry are being researched in an effort to enhance the efficiency of fuel cells including fuel cell design, the fuel type and oxidant type, as well as the type and activity of the catalyst. To design a fuel cell for practical, commercial use, the cells should be mechanically stable and not require cost-prohibitive fuels, design, or catalysts. Several types of fuel cells are generally accepted for practical application.

One type, hydrogen-oxygen fuel cells, are practical because the high electrochemical reactivity of hydrogen makes these cells the most efficient of all fuel cells yet designed. Hydrogen-oxygen fuel cells are also attractive because water is the only product, as indicated in the following reaction scheme:

$$2H_2 \longrightarrow 4H^+ + 4e^- \quad \varepsilon° = 0 \text{ V} \tag{I}$$

$$O_2 + 4H^+ + 4e^- \longrightarrow 2H_2O \quad \varepsilon° = 1.229 \text{ V} \tag{II}$$

$$2H_2 + O_2 \longrightarrow 2H_2O \tag{III}$$

While hydrogen has a high energy density and unlimited availability, so long as there is water available to decompose into hydrogen, it has the disadvantages of having a low mass density, creating storage difficulties for large quantities. It is also flammable and explosive.

A second type of fuel cell being studied for practical purposes is an indirect methanol-oxygen fuel cell. Indirect methanol-oxygen fuel cells rely upon steam reformation of methanol to produce a hydrogen-rich gas. The hydrogen reacts with oxygen in the cell to generate water:

$$2H_2 + O_2 \rightarrow 2H_2O \tag{IV}$$

While the indirect methanol-oxygen fuel cell may be an improvement over hydrogen-oxygen fuel cells with respect to less expensive and safer storage of the fuel (methanol), the portability of such fuel cells is limited by the size of the methanol reforming device required for the reaction and by the operating temperature of that device.

The third type of practical fuel cell is the direct methanol fuel cell (DMFC). The DMFC has the advantages of the indirect methanol fuel cell without sacrificing portability or safety. The DMFC electrochemically converts methanol into carbon dioxide and water without requiring an intermediate reformation of methanol into hydrogen gas. The overall reaction for this type of fuel cell is as follows:

$$CH_3OH + 3/2 O_2 \rightarrow CO_2 + 2H_2O \qquad (V)$$

The products of this reaction are environmentally less harmful than products released by other commercial electricity generation methods. Unfortunately, the conversion rate of aqueous methanol is low using currently available catalysts. The rate of conversion increases in acidic media. However, this imposes an additional requirement: that the catalyst be chemically resistant to acid. Another shortcoming of existing DMFCs is that the platinum anode catalysts can become poisoned by a variety of methanol partial oxidation products. As such, there is a need in the art to develop a less poisoning-susceptible catalysts for such cells and to make the DMFCs more commercially feasible.

There is still a significant need in the art for improved DMFC catalysts, particularly anode catalysts. At the anode of such fuel cells, the following reaction takes place:

$$CH_3OH + H_2O \rightarrow CO_2 + 6H^+ + 6e^- \qquad (VI)$$

The first anode catalysts used in DMFCs were platinum black. Platinum catalysts are fairly effective in DMFCs, but become poisoned by methanol partial oxidation products, thereby lowering the lifetime of the catalyst. Catalyst poisoning is believed to occur when partially oxidized products of methanol react and bond to the surface of the platinum catalyst, reducing the number of available catalytic sites. Continued poisoning eventually renders the catalyst useless.

A DMFC design includes two catalytic electrodes separated by a conductive ion-exchange membrane. The anode side of the cell is typically filled with a 0.5–2.0 molar aqueous methanol solution. On the cathode side, oxygen is bubbled through a low pH aqueous solution at a pressure of 1.0–5.0 atmospheres of oxygen. The reaction products, carbon dioxide and water, are continuously removed from the cell. The anode and cathode are connected by an electrical circuit. Methanol must be introduced into the anode in the vapor phase to avoid the problem of dehydration of the electrode membrane. The efficiency of DMFCs can be increased by raising the temperature of the fuel cell above 100° C. which vaporizes the methanol and accelerates the rate of reaction (V) noted above. Use of metal catalysts supported on conductive supports of high surface area is preferred for practical applications.

Attempts to enhance reactivity at the anode include addition to the catalyst composition of another metal wherein a metal-oxygen bond energy similar to that of the platinum-carbon bond energy is postulated to reduce catalyst poisoning. Catalysts comprising the metal combinations platinum-ruthenium, platinum-rhenium, and platinum-tin were shown to exhibit enhanced catalytic activity relative to catalysts consisting of platinum alone.

There is still a need in the art for a commercially feasible method for making polymetallic nanocomposites in the form of well-dispersed, uniformly sized crystalline nanoparticles on a support and in which the metals are present in commercially desired stoichiometric ratios. This need in the art is the focus of intense research in DMFC catalysis. The purity of the nanoparticles, that is a high degree of dispersion with little or no variation of phases or impurities is important. The purity of the alloy is significant in that it enables successful methanol oxidation by avoiding poisoning and facilitating the methanol oxidation reaction.

Metal/carbon nanocomposites formed of metal nanoparticles supported on a carbon powder of high surface area are commonly used heterogeneous catalysts in both small- and large-scale chemical processes in various fields, particularly those involving hydrogenation/dehydrogenation reactions. Bird, In: *Catalyst Supports and Supported Catalysts: Theoretical and Applied Concepts*, Stiles, Ed., Buttersworth, Boston, pp. 107–137 (1987); Satterfield, In: *Heterogeneous Catalysis in Industrial Practice*, McGraw-Hill, New York (1991). Heterogeneous catalysts comprising bimetallic alloy nanoparticles as the active catalyst have been of great interest because of their unique chemical reactivity. Sinfelt, In: *Bimetallic Catalysts: Discoveres, Concepts, and Applications*, Wiley, New York (1983); Ponec, *Adv. Catal.* 32:149 (1983); Moser, Ed., In: *Advanced Catalysts and Nanostructured Materials*, Academic Press, San Diego (1996).

Such carbon-supported nanoparticles, particularly platinum and platinum-rich alloy nanoparticles, such as platinum-ruthenium, are useful fuel cell catalysts. Catalysts that have been studied include PtRu, $Pt_3Ru$, and PtPb. Gasteiger et al., *J. Electrochem. Soc.* 141:1796 (1994); Hamnett et al., *J. Electrochimica Acta* 33:1613 (1988); Watanabe et al., *J. Electroanal. Chem.* 229:396 (1987). These catalysts have also been investigated for use as anode catalysts in fuel cells. For a fuel cell to work efficiently, a good cathode catalyst is also required. Pt—Ru nanoparticles supported on an electrically conductive carbon support of high surface area (such as VULCAN™ Carbon XC-72R, Cabot Corporation) are now recognized as highly reactive anode catalysts in DMFCs. Hamnett, *Catal. Today* 38:445 (1997); Hogarth et al., *Platinum Metals Rev.* 40:150 (1996); Chandler et al., *Platinum Metals Rev.* 41:54 (1997); Ralph, *Platinum Metals Rev.* 41:102 (1997); Hamnett et al., *Chem. Ind.* 480 (1992); Ren et al., *Electrochem. Soc.* 143:L12 (1996); Hogarth et al., *Proc. First Intern. Symp. New Mater. Fuel Cells* 310 (1995); Lin et al., *J. Electrochem. Soc.* 144:1917 (1997); Gasteiger et al., *Electrochem. Soc.* 141:1795 (1994); Surampudi et al., *J. Power Sources* 47:377 (1994); Wang et al., *Electrochim. Acta* 41:2587 (1996); Pathanjali et al., *Bull. Electrochem.* 12:193 (1996).

Binary Pt—Ru/carbon catalysts wherein the metal alloy comprises at least 50 atomic percent platinum have been found to exhibit superior activity for fuel cells relative to that of Ru-rich catalysts. Gasteiger et al., *J. Electrochem. Soc.* 141:1795 (1994). $Pt_1Ru_1$/Vulcan carbon powder nanocomposites are now commercially available, e.g. from ElectroChem, Inc., Woburn, Mass.; E-TEK, Inc., Natick, Mass.; Electrosynthesis Co., Inc., Lancaster, N.Y.; and, Johnson Matthey Plc., Hertfordshire, England.

Carbon-supported metal or metal alloy nanocomposites containing Pt (or Pd) are commonly prepared using various impregnation/reduction or chemical vapor deposition methods. A typical procedure involves impregnation of powdered carbon by solutions of Pd or Pt salts followed by drying and subsequent chemical reduction of the metal ions to the metal. Bird, In: *Catalyst Supports and Supported Catalysts: Theoretical and Applied Concepts*, Stiles, Ed., Buttersworth, Boston, pp. 107–137 (1987); Satterfield, In: *Heterogeneous Catalysis in Industrial Practice*, McGraw-Hill, New York (1991). Mixtures of hydrogen and nitrogen gases, such as 10 percent by volume hydrogen and 90 percent by volume nitrogen (known as "getter gas") are common reducing agents. Pt—Ru/Vulcan carbon composites are usually synthesized by either co-deposition of Pt and Ru from aqueous solutions of platinum and ruthenium salts upon chemical reduction or by co-deposition of Pt and Ru from aqueous solutions of the sulfito complexes, $N_6[Pt(SO_3)_4]$ and $Na_4[Ru(SO_3)_3]$, following the Watanabe procedure. Watanabe et al., *Electroanal. Chem. Interfacial Electrochem*, 229:395 (1987).

Metal alloy/carbon nanocomposites have also been prepared using cluster complexes as molecular precursors to attempt to better control the relative metal stoichiometry of the metal alloy particles. Ichikawa, *M. Adv. Catal.* 38:283 (1992). Fe—Ru and Fe—Mn/carbon composites have been prepared from mixed-metal carbonyl cluster complexes as precursors. Kaminsky et al., *J. Catal.* 91:338 (1985); Venter et al., *J. Catal.* 103:450 (1987). In cluster-type polymetallic precursors, at least one atom of one of the metals is directly bonded to an atom of the second metal in the cluster. In addition, Pt—Ru composites with a $PtRu_5$ stoichiometry on carbon have been formed from a $PtRu_5C(CO)_{16}$ cluster precursor. Nashner et al., *J.Am.Chem.Soc.* 119, 7760–7771 (1997). However, there is still a need for nanocomposites and precursors for making such composites which are commercially economical and which provide desirable and controlled mixed metal nanocluster stoichiometries of at least a 1:1 ratio and preferably with at least 50% platinum.

Significant needs remain for improved catalysts suitable for uses such as anode catalysis in DMFCs and for methods of making such improved catalysts. The present invention satisfies these needs.

BRIEF SUMMARY OF THE INVENTION

The invention includes a polymetallic precursor having at least one first metal and at least one second metal and comprising at least one metal-ligand-metal group represented by the formula:

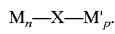

wherein M is an atom of the first metal, X is a thermally degradable ligand having a degradation temperature lower than degradation temperatures of M and M', M' is an atom of the first metal or the second metal, and n and p are each at least one.

In one embodiment of the invention, the polymetallic precursors are selected from the group consisting of Pt(triphenylphosphine)(Cl)($\mu$-Cl$_2$)Ru(Cl)-trihapto:trihapto-2,7-dimethyloctadienediyl); {Pt$_3$[$\mu$-bis(diphenylphosphino)-ethane]$_3$(Ru)(pentahapto-cyclopentadienyl)}[hexafluorophosphate]; [Ru($\mu$-2,3-bis(2-pyridyl)quinoxaline)PtCl$_2$)$_3$]-[tetrafluoroborate]$_2$; {Pt$_3$[$\mu$-bis(diphenylphosphino)-methane]$_3$($\mu_3$-Mo)(pentahapto-cyclopentadienyl)(CO)}[hexafluorophosphate]; {Pt$_3$[$\mu$-bis(diphenylphosphino)methane]$_3$($\mu_3$-Mo)(pentahapto-cyclopentadienyl)(CO)}[tetraphenylborate]; {Pt$_3$[$\mu$-bis(diphenylphosphino)methane]$_3$[$\mu_4$-Hg—Ru(pentahapto-cyclopentadienyl)(CO)$_2$]$_2$}[hexafluorophosphate]$_2$; [Ru(2,2'-bipyridine)$_2$($\mu$-bipyrimidine)PtCl$_2$][tetrafluoroborate]$_2$; Pt(dihapto-ethylene)(Cl)($\mu$-Cl)$_2$Ru(Cl)-(trihapto:trihapto-2,7-dimethyloctadienediyl); and {Pt$_3$($\mu$-W)(pentahapto-cyclopentadienyl)(CO)[$\mu$-bis(diphenylphosphino)methane]$_3$}[hexafluorophosphate].

A method of making a supported polymetallic nanoparticle is also included in the invention. The method comprises contacting a support with a polymetallic precursor comprising at least one first metal and at least one second metal and at least one metal-ligand-metal group represented by the formula:

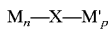

wherein M is an atom of the first metal; X is a thermally degradable ligand having a degradation temperature lower than degradation temperatures of M and M'; M' is an atom of the first metal or the second metal; and n and p are each at least one. The contacted support is heated in the substantial absence of an oxidizing agent to form a supported polymetallic nanoparticle comprising the first metal and the second metal at a selected atomic ratio, wherein the selected atomic ratio is approximately equal to a stoichiometric ratio of the first metal to the second metal in the polymetallic precursor.

The invention also includes a method of making a supported polymetallic nanoparticle, which comprises contacting a conductive support with a polymetallic precursor comprising at least one first metal and at least one second metal and at least one thermally degradable ligand. The contacted support is heated in the presence of an oxidizing agent to a first temperature to initiate degradation of the ligand. The contacted support is then heated to a second temperature in the substantial absence of an oxidizing agent to form a supported polymetallic nanoparticle comprising the first metal and the second metal at a selected atomic ratio, wherein the selected atomic ratio is approximately equal to a stoichiometric ratio of the first metal to the second metal in the polymetallic precursor.

The invention further includes a supported nanocomposite which comprises an electrically conductive support and a plurality of polymetallic nanoparticles which comprise at least one first metal and at least one second metal and which are formed from a polymetallic precursor comprising a metal-ligand-metal group represented by the formula:

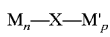

wherein M is an atom of the first metal, X is a thermally degradable ligand having a degradation temperature lower than degradation temperatures of M and M'; M' is an atom of the first metal or the second metal, and n and p are each at least one. The stoichiometric ratio of the first metal atoms to the second metal atoms in the polymetallic precursor is approximately equal to a selected atomic ratio of the first metal atoms to the second metal atoms in the polymetallic nanoparticles.

A supported nanoparticle is further within the invention which includes an electrically conductive support and a plurality of polymetallic nanoparticles, wherein the polymetallic nanoparticles comprise at least one first metal and at least one second metal and are formed by contacting the conductive support with a polymetallic precursor having the at least one first metal, the at least one second metal and at least one thermally degradable ligand, heating the contacted support in the presence of an oxidizing agent to a first temperature to initiate degradation of the ligand, and further heating the contacted support to a second temperature in the substantial absence of an oxidizing agent, wherein a stoichiometric ratio of the first metal atoms to the second metal atoms in the polymetallic precursor is approximately equal to a selected atomic ratio of the first metal atoms to the second metal atoms in the polymetallic nanoparticles.

The invention includes a fuel cell catalyst composition which comprises a supported nanocomposite. The supported nanocomposite comprises an electrically conductive support and a plurality of polymetallic nanoparticles. The nanoparticles are formed from a polymetallic precursor comprising a metal-ligand-metal group represented by the formula:

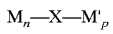

$M_n—X—M'_p$ wherein M is an atom of the first metal, X is a thermally degradable ligand having a degradation temperature lower than degradation temperatures of M and M', M' is an atom of the first metal or the second metal, and n and p are each at least one. The stoichiometric ratio of the first metal atoms to the second metal atoms in the polymetallic precursor is approximately equal to a selected atomic ratio of the first metal atoms to the second metal atoms in the nanoparticles.

A fuel cell catalyst composition is also within the scope of the invention which comprises a supported nanocomposite, wherein the nanocomposite comprises an electrically conductive support and a plurality of polymetallic nanoparticles, and wherein the polymetallic nanoparticles comprise at least one first metal and at least one second metal and are formed by contacting the conductive support with a polymetallic precursor having the at least one first metal, the at least one second metal and at least one thermally degradable ligand, heating the contacted support in the presence of an oxidizing agent to a first temperature to initiate degradation of the ligand, and further heating the contacted support to a second temperature in the substantial absence of an oxidizing agent, wherein a stoichiometric ratio of the first metal atoms to the second metal atoms in the polymetallic precursor is approximately equal to a selected atomic ratio of the first metal atoms to the second metal atoms in the polymetallic nanoparticles.

The invention also includes a method for making a metallic nanocomposite which comprises contacting a support with a metallic precursor having at least one metal and at least one degradable ligand, wherein the degradation temperature of the at least one ligand is lower than the degradation temperature of the metal in the precursor. The contacted support is heated in the substantial absence of an oxidizing agent by microwave radiation to degrade the at least one ligand and form a metallic nanocomposite.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings:

FIG. 11a–FIG. 11b is an XRD diffraction pattern of a palladium nanocomposite formed in accordance with Example 3;

FIG. 12a–FIG. 12b is an XRD diffraction pattern of a platinum nanocomposite formed in accordance with Example 3;

FIG. 13 is an XRD diffraction pattern of a platinum-ruthenium ($Pt_1Ru_1$) nanocomposite formed in accordance with Example 3;

FIG. 14a–FIG. 14b is an XRD diffraction pattern of the platinum-tin (PtSn) nanocomposite formed in accordance with Example 12;

FIG. 15a–FIG. 15b is an XRD diffraction pattern of the platinum-tin ($Pt_3Sn$) nanocomposite formed in similar to that described in Example 13;

FIG. 16a–FIG. 16b is an XRD diffraction pattern of the platinum-molybdenum ($Pt_3Mo$) nanocomposite formed in accordance with Example 15;

DETAILED DESCRIPTION OF THE INVENTION

Figure 1:
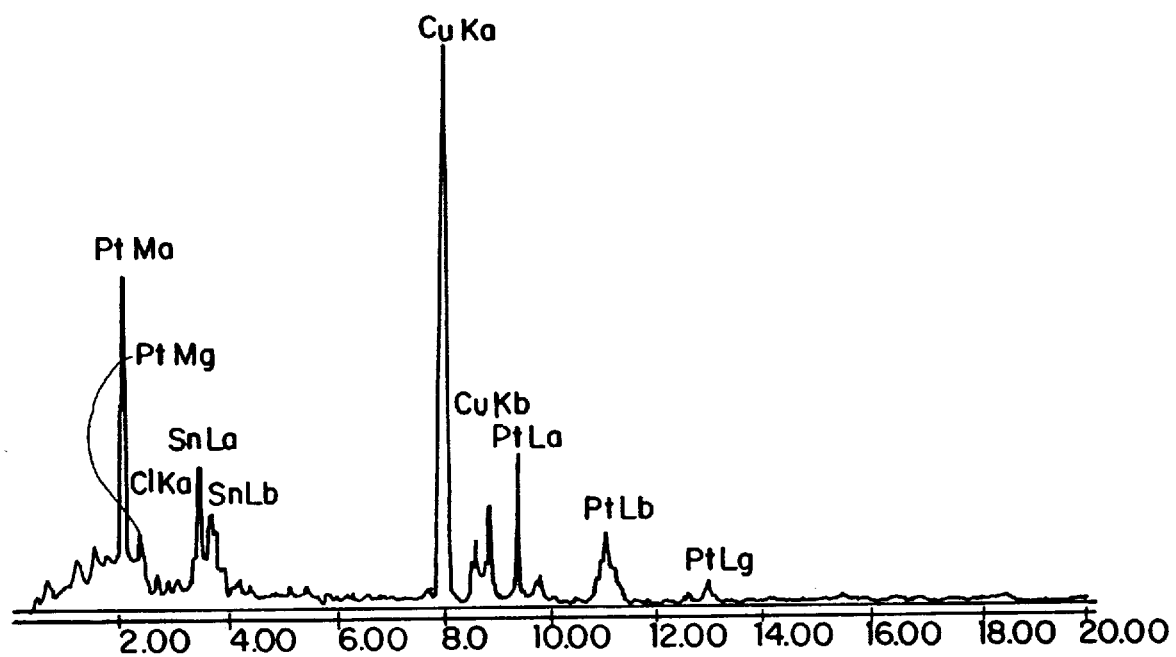
FIG. 1 is the energy dispersive spectrum (EDS) for nanocomposite Composite 7 formed in accordance with Example 1.

The field of the invention is catalysis, particularly fuel cell catalysts useful for DMFCs. The invention includes fuel cell catalyst compositions having supported nanocomposites which include electrically conductive supports and a plurality of polymetallic nanoparticles, supported nanocomposites, methods for making supported polymetallic nanoparticles, and novel polymetallic precursors for use in making nanocomposites. In addition, the invention includes a method of making a metallic nanocomposite from both novel and known precursors by using novel microwave radiation heating. The methods for making nanocomposites in accordance with the invention may use polymetallic precursors of both cluster and non-cluster types, and involve depositing them on or within a support and thermally treating them as described herein, such that the precursors decompose by degradation of the ligands in the precursor to form polymetallic metal alloys.

"Polymetallic" as used herein is intended to include bimetallic, trimetallic, tetrametallic and so forth. The method for forming nanocomposites using microwave radiation in accordance with the invention may be used with any metallic precursor, singular or polymetallic, to quickly form high quality nanocomposites having stoichiometries of commercial importance.

A significant feature of the method described herein for making polymetallic nanocomposites is that a commercially desirable stoichiometry can be predetermined for the nanoparticles in the nanocomposite, and a precursor thereby selected to provide that stoichiometry. This concept is expressed herein with reference to a "selected atomic ratio" of first metal atoms to second metal atoms in the nanoparticles which represents a predetermined, preferably commercially desirable atomic ratio for the nanoparticles in the nanocomposite. The selected atomic ratio also encompasses nanocomposites having nanoparticles of three of more metals atoms in which there is a predetermined, preferably commercially desirable atomic ratio of the first to second metal atoms in the nanoparticles, the second to the third metal atoms and so forth. The selected atomic ratio in the nanoparticles is achieved by selecting a precursor having a stoichiometric ratio of first metal atoms to second metal atoms, and second metal atoms to third metal atoms and so forth for three or more metal atoms, which is approximately equal, and preferably is equal, to the selected atomic ratio(s) in the polymetallic nanoparticles.

Polymetallic precursors of the invention preferably have a stoichiometric ratio of the first metal to the second metal which is approximately equal to, and preferably equal to, the selected atomic ratio in a nanocomposite formed from such a precursor. "Approximately equal to" as used herein means that the stoichiometric ratio does not differ from the atomic ratio by more than 20% of the value of the atomic ratio as measured by EDS, chemical microanalysis or other experimentation yielding a similar degree of accuracy.

The novel polymetallic precursors according to the invention have at least one first metal and at least one second metal, and at least one metal-ligand-metal group wherein the ligand is a thermally degradable ligand. The thermally degradable ligand is preferably interposed between at least one first metal atom and at least one other metal atom in the precursor, as a bridging ligand according to the formula

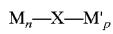

wherein M represents an atom of the first metal in the precursor, X is the thermally degradable ligand, and M' may be an atom of either the first or second metal in the precursor.

The ligand X may act as a bridging ligand between two different metals in the precursor, or two of the same metals in the precursor. Other non-bridging ligands, which are preferably also thermally degradable, may also be attached to only one metal or to another thermally degradable group. More preferably, the ligand X is a bridging ligand which connects two different metals in the precursor which will form the polymetallic alloy in a nanocomposite formed from the precursor. For example, if a platinum/ruthenium nanocomposite is to be formed, the first metal is platinum, and the second metal in the precursor is ruthenium. It is preferable, that at least one thermally degradable ligand extends between at least one platinum atom and at least one ruthenium atom in the precursor. However, the ligand may also extend between two platinum atoms, between two ruthenium atoms, or be simply attached to one of the metal atoms or to other thermally degradable ligands or groups.

The ligand(s) X in the novel polymetallic precursors according to the invention may be selected from numerous elements or groups so long as they are thermally degradable ligands which have a degradation temperature lower than the degradation temperature of the at least one first metal, the at least one second metal or any other metals which are desired in the final nanoparticle alloys. Such substituents may be single atoms, compounds or larger moieties and may include, but are not limited to, halogen atoms such as chlorine and mercury atoms, phosphorus atoms, other main group metal atoms from Groups 14–17 of the Periodic Table such as sulfur and selenium and compounds of these elements, and organic or substituted organic ligands such as alkyl, alkenyl, alkynyl, aryl, aralkyl, alkylphosphino, arylphosphino, alkylsulfido, arylsulfido, alkylselenide, arylselenide, alkylmercuric, arylmercuric, and other groups such as carbon monoxide, ammonia, amines, alkenes, heteroatomic aromatic molecules, arsenes, and derivatives, and substituted and unsubstituted versions of the compounds and moieties. While it is conceivable to use virtually any organic chain length, and branched or straight chain organic substituents, it is preferred, for practicality and economic reasons, that if organic or substituted organic groups are used, the organic group has from one to 50 carbon atoms.

In one preferred embodiment, all of the precursor is thermally degradable, including bridging and non-bridging ligands, with the exception of the core metals, i.e., the first and second metals (or higher numbers of metals for ternary or higher alloys), which would form the alloy phase of a nanocomposite formed from the precursor. The degradation temperature of the thermally degradable ligand(s) is the temperature at which the ligands substantially dissociate from the metal atoms by volatilizing, by substantially destroying the bonds between the ligands and the metal atoms such that the ligands are vaporized or otherwise substantially separated from the metal, or by chemically reacting with gases used during thermal treatment and leaving as volatilized compounds. Preferably all of the ligand(s) degrade. However, it will be understood, based on this disclosure, that some amount of organic or inorganic residue may be retained in the final composite. However, it is intended that the ligands are at least substantially removed by degradation.

The thermal degradation temperature of the ligands is preferably lower than the degradation temperature for the core metal(s) in the precursor which are intended to form the alloy phase of a nanocomposite formed from the precursor. The degradation temperature of the metals, as that term is used herein, refers to a temperature sufficiently high such that the metals are substantially destroyed or otherwise removed through chemical reaction with gases during thermal treatment and subsequent volatilization, or are otherwise substantially volatilized by thermal treatment. It should be understood, based on this disclosure, that degradation of precursors could produce intermediate metal compounds such as metal oxides, metal phosphides and other metal substances. As such, the degradation temperature of the metals would preclude retention of metals in the form of oxides, derivatives or other intermediate forms. As such, when degradation of the ligands occurs according to the invention, it occurs at a temperature sufficient to substantially remove the ligands from the metals while leaving the metals behind as metal atoms, compounds or intermediates, and preferably in a substantially pure, alloy state.

By forming a precursor in which the ligand(s), preferably the bridging ligands, and more preferably all of the precursor with the exception of the core metals are thermally degradable, either by heat or chemical reaction, at a temperature lower than the degradation temperature of the metals, the precursor is easily destroyed leaving only the core metals for forming the alloy phase behind. The exception to such a precursor, however, is that if particular atoms or groups are desired in the final alloy phase in the resulting nanocomposite, such as phosphorus atoms, sulfur atoms, selenium atoms, or other desired derivative groups, as discussed further below, the temperature used for destroying the precursor and forming the alloy must be chosen such that the degradation temperature of the thermally degradable ligands (other than the desired atoms or groups) is lower than the degradation temperature of the desired atoms or groups and also lower than the degradation temperature of the core metals for forming the alloy. In addition, the reaction of desired atoms and groups with gases introduced during thermal treatment should be avoided to prevent reactions forming volatilizable compounds from the desired atoms or groups. In this way, only the metals and the desired groups would remain after degradation.

Preferably, in the precursors, substantially every atom of every ligand bound to a first metal atom or to a second metal atom is thermally degradable therefrom with the exception of groups which may be desired in the final nanocomposite formed from the precursor for some applications. As such, degradation of "substantially every atom" herein means that all but core metals and/or desired atoms or groups in combination with core metals are intended to be thermally degradable. In certain situations, as described above, it is desirable that an atom of one or more ligands is not thermally degradable from the precursor. For example, when it is desired that the composition of the nanoparticle comprise phosphorus, a polymetallic precursor comprising a phosphorus-containing ligand may be used, so that when the precursor is subjected to thermal treatment all of the atoms of the ligand dissociate from the metal atoms of the precursor with the exception of one or more phosphorus atoms. Examples of such ligands include phosphorus atoms and compounds, and phosphorus-containing molecules such as diphenylphosphino and diphenylphosphino methane moieties, and trialkyl phosphino moieties such as triethylphosphine, triarylphosphino moieties such as triphenylphosphine, bisphosphino moieties such as bis (diphenylphosphino)methane, and other similar organic phosphorus-containing molecules. Alternatively, the same precursors having phosphino or similar moieties can be used to form nanocomposites without such groups if the method of making the nanocomposite is adjusted accordingly as discussed below. While examples relating to phosphorus are provided herein, it will be understood, based on this disclosure, that other related atoms, compounds and organo derivatives based on elements such as sulfur, selenium and other Group 14–17 metals from the Periodic Table may be similarly provided to a resulting alloy.

The polymetallic precursors of the invention preferably have at least two different metals in varying stoichiometric ratios and are chosen depending on the selected atomic ratio for nanoparticles formed from the precursors. Exemplary combinations of metals in the precursors are platinum-tin, platinum-ruthenium, platinum-tungsten, platinum-osmium, platinum-iridium, platinum-rhodium and platinum-gold which, using a stoichiometry in the precursor which is approximately that of the nanocomposite formed from the precursor, nanocomposites having desired commercial selected atomic ratios can be formed, e.g., PtSn, PtSn and $PtP_2$, $Pt_3Sn$, $Pt_3Sn$ and $PtP_2$, PtAu, PtAu and $PtP_2$, $Pt_2W$, and $Pt_2W$ and $PtP_2$, PtRu, $Pt_3Ru$, $Pt_3Mo$, RuMo, and others.

Preferred, novel polymetallic precursors which have been formed in accordance with the present invention include a precursor having a trigonal-bipyramidal $Pt_3Hg_2$ moiety, preferably, $\{Pt_3[\mu\text{-bis(diphenylphosphino)methane}]_3[\mu_4\text{-}Hg\text{—}Ru(\text{pentahapto-cyclopentadienyl})(CO)_2]_2\}$ [hexafluorophosphate]$_2$; as well as Pt(triphenylphosphine) $(Cl)(\mu\text{-}Cl_2)Ru(Cl)(\text{trihapto:trihapto-2,7-dimethyloctadienediyl})$; $\{Pt_3[\mu\text{-bis(diphenylphosphino)methane}]_3(Ru)(\text{pentahapto-cyclopentadienyl})\}$ [hexafluorophosphate]; $[Ru(\mu\text{-2,3-bis(2-pyridyl)quinoxaline})PtCl_2)_3][\text{tetrafluoroborate}]_2$; $\{Pt_3[\mu\text{-bis(diphenylphosphino)methane}]_3(_3\text{-Mo})(\text{pentahaptocyclopentadienyl})(CO)\}[\text{hexafluorophosphate}]$; $\{Pt_3[\mu\text{-bis(diphenylphosphino)methane}]_3(\mu_3\text{-Mo})(\text{pentahapto-cyclopentadienyl})(CO)\}[\text{tetraphenylborate}]$; $[Ru(2,2'\text{-bipyridine})_2(\mu\text{-bipyrimidine})PtCl_2]$ [tetrafluoroborate]$_2$; and Pt(dihapto-ethylene)(Cl)$(\mu\text{-Cl})_2$Ru (Cl)(trihapto:trihapto-2,7-dimethyloctadienediyl).

In the polymetallic precursor of the invention, there are at least two different types of metals, referred to herein for reference as a first metal and a second metal, although it should be understood, based on this disclosure, that there may also be a third or more metals in the precursor. It should also be understood that while there are preferably two or more different metals in the precursor, there may be at least one atom of each of the first metal and the second metal. The first metal is preferably a noble metal such as platinum, palladium, gold, or any other transition metal or Lanthanide metal. The at least one second metal may be any of the metals acceptable for the at least one first metal including metals from Groups 13–16, like tin; however, the at least one first metal is preferably different from the at least one second metal.

In one embodiment, of the polymetallic precursors of the invention, the at least one first metal is a noble metal and the stoichiometric ratio of the first metal atoms to the second metal atoms in the precursor is greater than or equal to about one such that there is preferably at least 50 at % of the first metal in the precursor and resulting nanoparticles. The at least one second metal in another embodiment is also a noble metal. In preferred precursors according to the invention, the first metal is platinum and the second metal is at least one of tin, ruthenium, tungsten, gold, molybdenum, rhenium, osmium, and palladium, and the stoichiometric ratio of platinum to the second metal(s) is equal to at least about one such that there is at least 50 at % platinum in the precursor and resulting nanocomposite.

The polymetallic precursors which are useful in the methods described herein may be made using any suitable method, including known techniques or other techniques which may be developed in the art. Typical methods for synthesizing precursors are included in the Examples herein. The precursors of the invention may be cluster and non-cluster types. In the method for forming nanocomposites as discussed below, which may be practiced using the novel precursors, or under certain circumstances, using any polymetallic precursor, it is preferred in some instances to use non-cluster types as they are easier to synthesize with a known stoichiometry which is to be the approximately equal to the selected atomic ratio of the nanoparticles formed from the precursors. However, even though the core metals are bonded in the cluster precursors, cluster precursors according to the present invention which have the desired commercial stoichiometries or which otherwise contain a desired metal-ligand-metal group within the precursor structure between one or more of the metals and having the criteria described above, may be used in accordance with the invention.

The invention also includes methods of making a supported polymetallic nanoparticle. In one embodiment, the invention includes a method in which a support is contacted with a novel polymetallic precursor according to the present invention and the contacted support is heated in the substantial absence of an oxidizing agent. In an alternative embodiment, the invention includes a method in which a conductive support is contacted with any suitable polymetallic precursor, the contacted support is heated in the presence of an oxidizing agent and then further heated in the substantial absence of an oxidizing agent.

The novel polymetallic precursors for use in the first embodiment may be any of the novel precursors above wherein the precursor have at least one first metal, at least one second metal and at least one metal-ligand-metal group including two metal atoms, which may be the same or different, interconnected by a thermally degradable ligand which has a degradation temperature lower than the degradation temperature of the metals to which it is bonded and in the precursor. The first and second metals and metal-ligand-metal groups may be any of those described above with respect to the novel precursors of the present invention. Most preferably, the polymetallic precursors are the novel precursors described above and which meet the above criteria.

In the alternative embodiment, the polymetallic precursor may be any bimetallic or higher precursor having a first metal and a second metal, such as those described above, and at least one thermally degradable ligand. The thermally degradable ligand need not be interposed between two metal atoms, and may be any of the thermally degradable ligands described above with respect to ligand X in the novel precursors of the present invention. In the alternative embodiment, the precursors may be the novel precursors listed above as well as any bimetallic or higher precursors conventionally used or to be developed for nanocomposite forming methods provided the precursor selected has at least two different metals and the thermally degradable ligands have degradation temperatures lower than the degradation temperature of the core metals as those terms are described and defined above. In addition, other atoms or desired groups such as phosphides, sulfides, selenides and the like as described above may also be incorporated in the precursor and retained in the nanocomposite in accordance with the above criteria described in connection with the novel precursors described above.

In either embodiment of the methods for making supported polymetallic nanoparticles, the polymetallic precursors have a stoichiometric ratio of the first metal atoms to the second metal atoms which is approximately equal to the selected atomic ratio of first metal atoms to second metal atoms in the nanocomposite formed by the methods of the present invention. Exemplary precursors which may be used in either embodiment of the methods of the present invention include the preferred, novel precursors listed above as well as the precursors such as $\{Ru(2,2'\text{-bipyridine})_2PtCl_2(\mu\text{-bipyrimidine})\}[hexafluorophosphate]_2$; $Pt(triphenylphosphine)_2Phenyl)Sn(phenyl)_2Cl$; $Pt(triethylphosphine)_2(Cl)Sn(Cl_3)$; $\{Pt_3[\mu\text{-bis}(diphenylphosphino)methane]_3(\mu_3\text{-SnF}_3)(\mu_3\text{-CO})\}$ [hexafluorophosphate]; $\{Pt_3(\mu_3\text{-Au}(triphenyl\text{-phosphine})[\mu\text{-bis}(diphenylphosphino)methane]_3\}[hexafluorophosphate]$; and $Mo(heptahapto\text{-cycloheptatrienyl})(CO)_3(Ru)(pentahapto\text{-cyclopentadienyl})(CO)_2$.

In either method, the polymetallic precursor is deposited onto or within a support, for example by suspending the precursor in a liquid, contacting the liquid with the support, and evaporating the liquid or by using incipient wetness techniques. Thermal treatment of the precursor causes the thermally degradable ligand(s) of the precursor to dissociate from at least one first metal atom and from at least one second metal atom of the precursor, whereby first metal atoms and second metal atoms may combine under thermal treatment to form an alloy having an atomic ratio approximately equal to the stoichiometric ratio of the first metal to the second metal in the precursor. Formation of a catalyst having the selected atomic ratio of the first metal to the second metal may be improved if the thermal decomposition is performed in the substantial absence of an oxidizing agent, and preferably in the presence of a reducing agent such as hydrogen. As described below, the substantial absence of an oxidizing agent" is intended to mean that the atmosphere includes little or no oxidizing agents, although limited amounts of oxidizing agent may be present. However, in a reducing thermal treatment, it is not preferred. As will be understood by one skilled in the art, based on this disclosure, formation of a nanoparticle comprising a desired metal alloy may be affected by the rate of heating during the thermal treatment. Cooling may typically be performed by allowing the nanoparticles to come to room temperature naturally or by quenching. Known heating regimens are therefore included within the thermal treatments of the method of the invention.

Catalysts, particularly fuel cell catalysts, prepared using this method to generate polymetallic nanoparticles on a conductive support have utility as either anode or cathode fuel cell catalysts, particularly in DMFCs. The methods of the invention may also be used to generate polymetallic nanoparticles having the metal composition of many known polymetallic catalysts. The skilled artisan in the field of catalysis is enabled by this disclosure to prepare catalysts comprising nanoparticles which have these known metal compositions, and such catalysts and the methods of making them are included in the present invention.

The synthetic strategy described above is equally applicable to the preparation of ternary or higher metal alloy catalysts. In such instances, selected atomic ratios among the three or more metals in the polymetallic nanoparticles of the catalyst are obtained by selecting a polymetallic precursor having stoichiometric ratios among the three or more metals approximately equal to the selected atomic ratios.

The polymetallic precursor may be contacted with the support in a number of ways. For example, the precursor may be dissolved or suspended in a liquid, and the support may be mixed with the liquid having the dispersed or suspended precursor. The dissolved or suspended precursor is thus enabled to adsorb onto a surface of the support or to be absorbed by the support. As an alternative to adsorption or absorption by such method, the precursor may also be deposited onto a surface of the support by removing the liquid, such as by evaporation such that the precursor remains on the support. The liquid may be substantially removed from the support prior to thermally treating the support in accordance with the method of the invention, such as by heating the support at a temperature lower than the temperature achieved during subsequent thermal treatment or by reducing the pressure of the atmosphere surrounding the support. Preferably, the support is dried prior to heating it.

The support may be a bulk article such as a metal rod, or a microscopic article such as a particle of particulate carbon. The support may include substantially any material which, when heated to a temperature at which a polymetallic precursor is converted to a polymetallic nanoparticle on the surface thereof, does not melt, vaporize completely, or otherwise become incapable of supporting polymetallic nanoparticles. In the embodiment of the invention in which the contacted support is first heated in air and then heated in the substantial absence of an oxidizing agent as described herein, it is preferred that the support be conductive. Further, when the intended use of a nanocomposite is as a fuel cell electrode, it is important that the support be electrically conductive. Preferably, the fuel cell support exhibits a conductivity sufficiently high as to not limit current flow used by a working fuel cell.

The most preferred support for use with the precursors and for use in fuel cell catalyst compositions according to the invention, is carbon in a particulate form, such as carbon black. Preferably, the particulate carbon has a mean particle diameter less or equal to than about 30 nanometers or a surface area of at least about 250 $m^2/g$. The inventors have determined that the carbon black product having the trade name Vulcan™ XC-72R carbon, which is available from Cabot Corporation, Billerica, Mass., is a suitable material, owing in part to its high electrical conductivity and its high specific surface area (about 250 $m^2/g$). While carbon is most preferred, other materials, including but not limited to, conductive materials having similar thermal stability, surface area and electrical conductivity to the above-noted preferred carbon will suffice for use as conductive supports in the compositions and methods of the invention.

Non-conductive supports may be used in connection with the method according to the present invention based on the novel precursors of the invention as well as the further embodiment of the method according to the invention based on microwave heating as described further below. Suitable non-conductive supports include xerogels, aerogels and the like.

The precursor-contacted support is preferably heated to a temperature equal to or greater than the thermal degradation temperature of the thermally degradable ligand(s) X, and preferably all such thermally degradable ligands in the precursors as described above. The preferred heating temperature will depend to a large degree on the particular thermally degradable ligands used and the degradation temperature of the core metals and any other desired groups which are to remain in the nanoparticles. However, the preferred temperature is at least 350° C., and more preferably at least 650° C., including temperatures as high as 700° C. The heating of the precursor-contacted support occurs in the substantial absence of an oxidizing agent in each of the above described embodiments of the methods of the invention. However, in the embodiment of the method including the initial heating step in the presence of an oxidizing agent, heating in the substantial absence of an oxidizing agent occurs subsequently to heating in the presence of an oxidizing agent and is a final heat treatment step which may or may not be followed by annealing as described below.

During the final heating step in the substantial absence of an oxidizing agent, it is preferred that the support is heated in the presence of a reducing agent, for example, a hydrogen-containing gas such as getter gas, to improve the amount of polymetallic precursor which is converted to crystalline polymetallic nanoparticles. Getter gas is a mixture of about 10 volume percent hydrogen and about 90 volume percent nitrogen. However, it will be understood, based on this disclosure, that other reducing agents may be used. After heating in the substantial absence of an oxidizing agent and/or in the presence of a reducing agent, the polymetallic nanoparticles having the same first and second metal atoms as the precursors in a selected atomic ratio are formed. The selected atomic ratio of the metal atoms in the nanoparticles is approximately equal to, and preferably equal to, the stoichiometric ratio of the metal atoms in the precursor.

Thermal treatment of a support upon which a polymetallic precursor has been deposited may be performed, for example, as follows. A sample of the contacted support is placed into a ceramic boat which is then inserted into a quartz tube that is positionable within a tube furnace. Fittings on the quartz tube permit the control of gaseous environment surrounding the sample. The quartz tube can be purged with gas (e.g. hydrogen, getter gas, nitrogen, air; sustained purges are typically maintained at a rate of about 150 ml/minute). Thermal treatment of the sample can be controlled through automated regulation of the heating or cooling of the furnace. Heating rates are typically about 15° C. per minute in the Examples described herein, but can be varied for different effects, preferably at rates of from about 10 to about 20° C./min. Thermal conditions and reactive atmospheres are chosen such that the molecular precursor(s) break down and degradation of the thermally degradable ligands occurs with nearly complete retention of the metal content of the precursor. Reduction of metals to the metallic state is assured using reducing thermal treatment, and formation of crystalline intermetallic or metal alloy nanoparticulates is achieved, for example, by thermal annealing.

In a preferred embodiment of the method using the novel precursors described herein and in the embodiment of the method using novel and conventional precursors described herein, before heating in the absence of an oxidizing agent or reducing agent, the support is initially heated in the presence of an oxidizing agent from about room temperature (about 25° C.) to a temperature sufficient to initiate degradation of the ligand(s) in the precursors, preferably to a temperature from about 250 to about 500° C., and more preferably to a temperature from about 280 to about 450° C. The support is then heated as noted above in the substantial absence of an oxidizing agent and/or in the presence of a reducing agent to a temperature sufficient to initiate reduction of any metal intermediates formed during oxidation and to complete degradation of the degradable ligand(s) in the precursor, preferably to the preferred temperatures noted above with respect to final heating in the substantial absence of an oxidizing agent such that crystalline polymetallic nanoparticles are formed in or on the support. While it is theorized that such metal intermediates include metal oxides and/or suboxides, the inventors herein do not know the exact intermediate species formed.

This thermal treatment regimen, including the initial step of heating in the presence of an oxidizing agent, is preferable when a ligand of a polymetallic precursor comprises an atom or group which is not easily thermally degradable from a metal atom of the precursor. Such atoms or groups of atoms may be those which are in some instances tolerable or desirable, such as those described above based on phosphorus, sulfur and the like, but which for other purposes are not desirable in the final alloy. In order to remove such groups, the atoms may be dissociated from the metal atom by formation of intermediate, oxidized reaction products of the ligand, presumably metal oxides, and the intermediate may thereafter be reduced so that the metal atom may be incorporated into a polymetallic nanoparticle without the atom or group.

As used herein, the "substantial absence of an oxidizing agent" as noted above indicates that the atmosphere includes little or no oxidizing agents, although limited amounts of oxidizing agent may be present. More specifically, the "substantial absence of an oxidizing agent" as used herein means in the presence of a gas which does not comprise enough of a oxidizing agent to cause oxidation of 25% or more of the metal atoms of the precursors during the thermal treatment. Preferably, virtually no oxidizing agent is present under such conditions.

Preferably, as noted above, the final thermal treatment is performed in the substantial absence of an oxidizing agent. Polymetallic nanoparticles are formed on the surface of or within the support as a result of the final heating step. Thermal treatment in the presence of an oxidizing agent facilitates one or more of the following functions: degradation of the ligand(s), deposition of the metal atoms of the precursor on the support, inhibition of agglomeration of deposited metal atoms into large metallic complexes, thereby preventing formation of large or non-homogeneously-sized particles, and minimization of the loss of metal atoms from the support during the thermal treatment.

Essentially any method may be used to heat the support. By way of example, the support may be heated by convection, by conduction, or by absorption of radiation, such as infrared radiation, by the support.

In a further embodiment of a method according to the present invention, microwave heating of the support is used and yields improved nanocomposite properties, as further described below.

As described herein, a promising new method for preparing metal or metal alloy/carbon nanocomposites has been developed and may have wide generality and potential development for large-scale applications. The microwave heating method includes contacting a support susceptible to microwave heating, for example, the carbon described above, with a precursor having at least one metal and at least one degradable ligand which has a degradation temperature lower than the degradation temperature of the metal. The degradation temperature is as described above with respect to the polymetallic precursors and other embodiments of methods of the present invention. However, in the microwave heating method, any singular metallic precursor, such as supported Pt, Mo, Ru and the like, in addition to any of the conventional and novel polymetallic precursors described above may be used, regardless of whether such precursors are known or unknown. The contacted support is then heated in the substantial absence of an oxidizing agent by microwave radiation to the preferred temperatures noted above for formation of polymetallic nanoparticles. An intermediate heating step in the presence of an oxidizing agent may also be incorporated in this method as described above wherein the support is heated to a temperature sufficient to initiate degradation followed by heating to the final heating temperature in the substantial absence of an oxidizing agent. The support is contacted prior to heating in accordance with the contacting steps noted above for the method of making a nanocomposite in accordance with the invention.

An important feature of the microwave heating embodiment of the invention relates to the fact that various types of carbon black interact with microwave irradiation, leading to a sharp rise in temperature due to dielectric loss. Galema, *Chem. Soc. Rev.* 26:233 (1997); Sutton, *Am. Ceram. Soc. Bull.* 68:376 (1989). The use of microwave technology not only provides improved nanocomposites from various precursors, but does so in a significantly short treatment time as demonstrated below in the Examples herein.

As described herein, applicants have discovered that Vulcan carbon XC-72R, which has high electrical and thermal conductivity, is efficiently heated under microwave irradiation. Microwave irradiation of a particulate carbon contacted with, coated with or impregnated with a single metal precursor or polymetallic precursors under appropriate atmospheres has herein been shown to directly afford metal or metal alloy/particulate carbon nanocomposites of excellent uniformity in the metallic phase in less than one minute of total irradiation time.

For thermal treatment in the other embodiments of the invention using heating methods other than microwave radiation, the rate at which the contacted support is heated, the temperature to which it is heated, and the duration of heating affect the properties of the nanoparticles. Typically, a slower rate of heating, a higher temperature, and a longer duration of heating all favor formation of larger nanoparticles and greater non-uniformity of nanoparticle size. Conversely, a faster rate of heating, a lower temperature, and a shorter duration of heating typically all favor formation of smaller nanoparticles and greater uniformity of nanoparticle size. The step of final heating preferably includes thermally annealing the nanoparticles at the maximum final heating temperature for a period of time sufficient to form a desired crystalline nanoparticle structure and to promote particle growth. Variations of such annealing may be found in the Examples herein.

After the contacted support is heated, whether by standard methods or the novel microwave heating of the present invention, the support is preferably cooled to around room temperature, for example between about 10° C. and 30° C. by allowing the support to cool naturally. However, support may be merely quenched or the rate of cooling controlled in order to form an alloy having favorable properties by using any known or to be developed metallurgical techniques, as would be apparent to one of ordinary skill in the art based on this disclosure. The rate at which the support is cooled can affect the properties of the nanoparticles.

It is known in the art that maintaining a metal alloy at a particular temperature for a period of time (thermal annealing), cooling the alloy at a particular rate, or both, can affect the crystalline structure and the physical, mechanical, and chemical properties of the alloy. These effects are discernable both at the scale of bulk alloy and at the nanoparticle scale. Exemplary techniques such as those which are described in the Examples herein may be used to alter the properties of alloy nanoparticles. Thus, for example, the rate of heating the support may be controlled by increasing the temperature of the support at a particular rate, such as about 15° C. per minute. Similarly, the duration at which a nanocomposite is maintained at a particular temperature during annealing may be varied for achieving different particle sizes, and enhanced crystallinity for some materials. The rate at which the nanocomposite is permitted to cool may also be varied to achieve similar property variations as would be apparent to those skilled in the art based on this disclosure and the Examples included herein. Preferably the temperature conditions are controlled such that the nanoparticle which is formed has a mean diameter equal to or less than about twenty nanometers, and even more preferably equal to or less than about five nanometers.

In heating and contacting the support, the method may further comprise repeating the thermal treatments, contacting steps and/or the steps of precursor deposition to enhance crystalline growth and/or to increase metal loading on the support. In one embodiment, the thermally treated contacted support is contacted with the precursor a second time followed by additional thermal treatments as described above. In another such embodiment, the contacted support is heated in the presence of an oxidizing agent as described above, contacted with the support a second time, followed by further heating in the presence of an oxidizing agent, and repetition of these steps to provide enhanced metal loadings prior to final thermal treatment in the substantial absence of an oxidizing agent or in the presence of a reducing agent. Such repetitive treatments may continue until desired affects and/or preferred higher precursor on carbon loadings are achieved. As a further example, after contacting the support with the precursor initially, the support may be heated either in the presence of an oxidizing agent or without such an oxidizing agent, then contacted again with the precursor, and then heated in the substantial absence of an oxidizing agent or in the presence of a reducing agent. Such steps may then be repeated at least once, and more times if higher precursor on carbon loadings are desired. Alternatively, the support may be contacted with the precursor multiple times prior to heating in the substantial absence of an oxidizing agent.

The invention also includes a supported nanocomposite which includes an electrically conductive support and a plurality of polymetallic nanoparticles preferably conductively connected to the support. The nanoparticles have at least one first metal and at least one second metal. The first metal is preferably a noble metal, and the selected atomic ratio of the atoms of the first metal to those of the second metal is equal to or greater than one as described above with respect to the precursors according to the invention. The nanoparticles are preferably formed from the novel polymetallic precursors according to the invention having the same first and second metals and at least one metal-ligand-metal group $M_n$—X—$M'_p$ where M, M', X, n and p are as described above. Alternatively, the nanoparticles are formed by contacting a conductive support with a polymetallic precursor having at least one first metal, at least one second metal and at least one thermally degradable ligand as described above, heating the contacted support in the presence of an oxidizing agent to a first temperature to initiate degradation of the ligand(s), and further heating the contacted support to a second temperature in the substantial absence of an oxidizing agent. In either embodiment, in the nanoparticles, the stoichiometric ratio of first to second metal atoms in the polymetallic precursor chosen is preferably approximately equal, and more preferably equal, to the selected atomic ratio of first to second metal atoms in the nanoparticles. It is also preferred that the selected atomic ratio be at least about one such that there is at least about 50 at % of the first metal in the nanoparticles. Preferably, the nanoparticles are formed in accordance with the methods of the invention as described in detail above.

The precursor(s) used to form the nanoparticles may be any precursor useful in the methods described above according to the invention as described herein. This supported nanoparticles may be included in a fuel cell catalyst composition, but is not limited to such a composition. Further, while it is preferred that the nanoparticles have a mean diameter less than or equal to about twenty nanometers and preferably less than or equal to about five nanometers, other variations are within the scope of the invention provided the above-described criteria are otherwise met. Fuel cell catalyst compositions or other compositions including the nanoparticles of the invention and a conductive support preferably include at least about 0.5% by weight nanoparticles, and preferably at least about 40% by weight, and even more preferably at least about 50% by weight nanoparticles. Using the methods described herein, applicants have achieved 50 wt % nanoparticles with a particle sizes of 1.5–2 nm. The nanoparticles preferably have at least 50 atomic percent of the first metal which is preferably a noble metal such as platinum and as described above with respect to the precursors.

In accordance with a preferred embodiment of the invention, the nanocomposites are formed from one or more of the novel polymetallic precursors described above and preferably having at least one metal-ligand-metal groups as described above.

A standardized test DMFC having an anode including the supported nanocomposite composition of the invention exhibited an unoptimized current density of about 700 mA/m$^2$ when the anode potential is about 0.38 Volt. In the standardized test DMFC, the degree of anode loading was equivalent to 2 milligrams of total metal of catalyst/cm$^2$ (i.e. both the first and the second metal, combined), the degree of cathode loading was equivalent to 4 mg platinum catalyst/cm$^2$. The methanol flowrate was 2 ml/min and the methanol backpressure was 30 psig. The oxygen flowrate was 600 ml/min and the oxygen backpressure was 30 psig. A Nafion® 112 membrane was used in the cell. Based on extrapolation of DMFC test data from testing various nanocomposites formed according to the invention, greater than 1000 mA/cm$^2$ at 0.40 V anode potential is expected.

The nanoparticles in the nanocomposite of the present invention are preferably substantially formed of, and more preferably virtually solely formed of the crystalline alloy form of the first metal and the second metal. By way of example, such crystalline alloy forms would include PtRu, PtSn, Pt$_2$W, Pt$_3$Sn, Pt$_3$Ru, Pt$_3$Mo, RuMo, mixtures of various of these forms with PtP$_2$, and various other stoichiometric combinations of core metals of the precursors described herein.

The nanocomposites may also be used within fuel cell catalyst compositions which include the support and a plurality of nanoparticles as described above. The composition may be formed into an electrode, such as an anode or cathode, for use in a fuel cell such as a DMFC by standard methods using standard ink electrode technology. When methanol is added to the fuel cell and contacts the electrode in the presence of oxygen, the oxidation of methanol is catalyzed by the nanoparticles and electrons extracted from methanol can be passed through the conductive connection of the particles to the support, and through the support to an external circuit, whereby direct current may be generated.

In one embodiment, the invention includes a fuel cell catalyst composition comprising a supported nanocomposite. The nanocomposite comprises an electrically conductive support and a plurality of polymetallic nanoparticles preferably conductively connected to the support. The nanoparticles in the nanocomposite and/or the fuel cell catalyst composition are preferably are formed almost exclusively of a first metal and a second metal, more preferably from a noble metal and a second metal, and may further comprise a phosphide moiety or other desired moiety. The nanoparticles and nanocomposite may be any of the above described nanocomposites. The fuel cell is preferably a DMFC, and the catalyst composition may be within the anode or cathode, preferably the anode, of the fuel cell. However, it will be understood by those skilled in the art, based on this disclosure, that the nanocomposites, precursors and methods of the present invention have the potential for many other catalytic applications.

The invention is now described with reference to the following non-limiting Examples. These Examples are provided for the purpose of illustration only, and the invention should in no way be construed as being limited to these Examples, but rather should be construed to encompass any and all variations which become evident as a result of the teaching provided herein.

EXAMPLE 1
Particulate Carbon Nanocomposites Having Nanoparticles of Pt/Sn, PtSn/PtP$_2$, Pt$_3$Sn/PtP$_2$, and Pt$_3$Sn In this example, the conditions of thermal treatments and the identity of the molecular precursor were altered, and two congruently melting platinum/tin intermetallic compounds were formed as nanoparticles on a particulate carbon support. Adsorption of a known molecular precursor onto Vulcan XC-72R carbon was used to yield two different platinum/tin nanocomposite compositions, depending on the conditions of oxidative and reductive thermal treatments. Using this approach, platinum/tin nanoparticles comprising the two highest congruently melting Pt/Sn intermetallic phases were formed. Highly pure crystalline Pt$_3$Sn nanoparticles have also been formed.

The materials and methods used in the experiments presented in this Example are now described.

The chemical reagents, bis(diphenylphosphino)methane ("dppm"), dichloro(1,5-cyclooctadiene)platinum (II) ("Pt(COD)Cl$_2$"), silver acetate, and tin (II) fluoride were purchased from Strem Chemical, Inc., Newbury Port, Mass. Trifluoroacetic acid, ammonium hexafluorophosphate, and sodium fluoride were purchased from Aldrich Chemical Company (St. Louis, Mo.). Vulcan XC-72R carbon was obtained from the Cabot Corporation. Getter gas was purchased from the Liquid Air, Inc., and had the composition, 10.3% by volume H$_2$, 89.7% by volume N$_2$.

Reactions were performed in oven-dried glassware under a nitrogen or carbon monoxide atmosphere. Methylene chloride and acetone were dried by distillation from calcium hydride and molecular sieves using known methods. Tetrahydrofuran and ether were purified by distillation from NaK alloy/benzophenone. Water was purified using a commercial water purifying apparatus. Other solvents and reagents were used without further purification.

Thermal treatments of molecularly doped Vulcan XC-72R carbon were carried out in a Lindberg/Blue 55341 solid tube furnace. The Vulcan carbon samples were placed into a Fisher brand Combax® sample boat and inserted into the tube furnace. Reducing and oxidizing atmospheres were introduced into the system at different times as the temperature was increased at a rate of 15° C./min. After heating the sample, it was cooled to room temperature before being removed from the furnace.

Nanocomposite material characterization was carried out using a Philips CM20T transmission electron microscope operating at 200 kV. Samples were pipetted onto a 3 mm diameter copper grid covered with amorphous carbon as a substrate after being suspended in methylene chloride by sonication. Samples were analyzed using standard bright-field imaging methods to determine particle size distribution, X-ray energy dispersive spectroscopy (EDS) methods, and selected area diffraction methods to determine electron diffraction patterns for semiquantitative chemical composition.

XRD scans were performed using a Philips PWI800 θ/2θ automatic powder diffractometer equipped with a copper target and a post-sample monochromator. Samples for XRD were prepared by placing a uniform layer of powdered nanocomposite onto a double-sided tape affixed to the sample holder. An approximately 1 cm×1 cm sample was examined.

Synthesis of Dichloro(bis(diphenylphosphino)methane)platinum (II) (Compound 1):

Pt(COD)Cl$_2$, in an amount of 0.75 g (2.00 mmol) was added, under a nitrogen atmosphere, to a 100 ml 3-neck flask which contained a Teflon™-coated magnetic stirring bar. To the flask was added 25 ml of methylene chloride, and the solution was stirred until the solid was completely dissolved. To this stirred solution, a solution comprising bis(diphenylphosphino)methane ("dppm") (0.77 g, 2.00 mmol) in 25 ml of methylene chloride was added dropwise over a 3-hour period from an addition funnel under a nitrogen atmosphere. After stirring overnight, a white precipitate formed and was filtered through a fine glass frit. The resulting white solid was dried under vacuum for 4 hours at 160° C. to yield Compound 1 (1.19 g, 87% yield) in accordance with reaction (VII) below.

The formation of the $\mu_3$-carbonyltris[$\mu$-[methylenebis[diphenylphosphine]-P:P']]-[$\mu_3$-(trifluorostannyl)]triplatinum (1$^+$)-triangulo hexafluorophosphate(1$^-$) molecular precursor described below as {Pt$_3$($\mu_3$-CO)[$\mu$-bis(diphenylphosphine)methane]$_3$($\mu_3$-SnF$_3$)} [hexafluorophosphate] (Compound 5) was undertaken as described by Jennings et al., *Organometallics* 10:585 (1991), herein incorporated by reference, and as shown in the following reaction sequence (VII)–(XI):

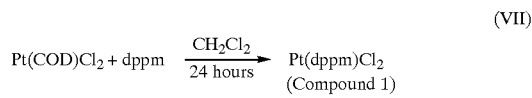
(Compound 1)

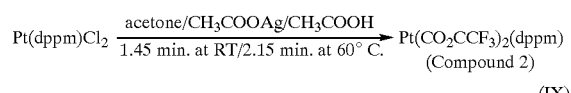
(Compound 2)

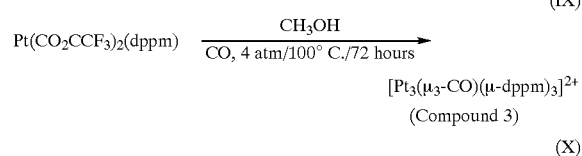
(Compound 3)

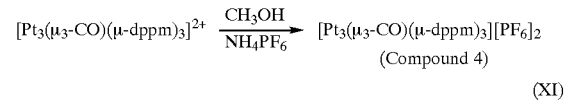
(Compound 4)

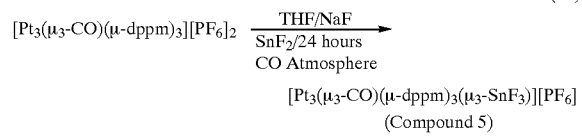
(Compound 5)

Adsorption of Compound 5 onto Vulcan XC-72R Carbon:

A sample of Compound 5 (0.109 g) was added to a 250 ml beaker along with Vulcan XC-72R carbon (0.158 g). A Teflon™-coated magnetic stirring bar and 50 ml of acetone were added to the beaker. The solution was stirred overnight. The solution was centrifuged, and acetone was decanted from the solid. The molecularly doped Vulcan carbon was allowed to air dry for 72 hours to yield Compound 6 (0.260 g).

Thermal Reduction of Compound 6 in a Hydrogen Atmosphere:

A sample of Compound 6 (0.100 g) was heated at 700° C. for 2 hours in a hydrogen atmosphere. The resulting black powder nanocomposite (Composite 7; 0.071 g) was analyzed by transmission electron microscopy (TEM) and EDS, which indicated that both PtSn and $PtP_2$ nanoparticles had been formed. EDS analysis: $PtL_\alpha$, $PtL_\beta$, $PtL_\gamma$, $PtM_\alpha$, $PtM_\beta$, $SnL_\alpha$, and $SnL_\beta$. Electron diffraction: interplanar d-spacings of both PtSn and $PtP_2$. The reaction sequence for formation of Compound 6 and Composite 7 is shown below in (XII) and (XIII):

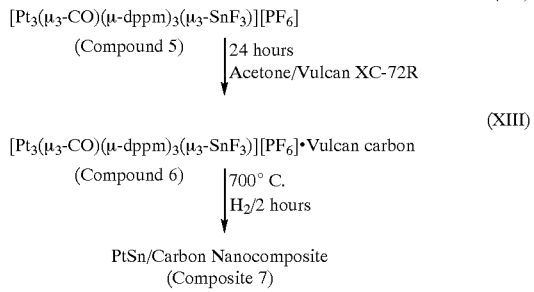

Thermal Reduction of Compound 6 in a Getter Gas Atmosphere:

A sample of Compound 6 (0.100 g) was heated to 650° C. at a rate of 15° C./min in a getter gas atmosphere in accordance with reaction (XIV) below.

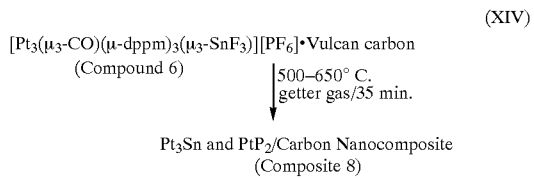

In reaction (XIV), after the temperature had reached 650° C., the atmosphere was changed to nitrogen and the temperature was maintained for 2 hours. The resulting black powder nanocomposite (Composite 8) (0.074 g) was analyzed by TEM and EDS, which indicated that both $Pt_3Sn$ and $PtP_2$ nanoparticles had been formed. EDS analysis: $PtL_\alpha$, $PtL_\beta$, $PtL_\gamma$, $PtM_\alpha$, $PtM_\beta$, $SnL_\alpha$, and $SnL_\beta$. Electron diffraction: interplanar d-spacings of both $Pt_3Sn$ and $PtP_2$.

Thermal Oxidation of Compound 6 in an Air Atmosphere Followed By Thermal Reduction in a Getter Gas Atmosphere:

A sample of Compound 6 (0.100 g) was heated to 280° C. at a rate of 15° C./min in an air atmosphere. After the temperature had reached 280° C., the temperature was held constant, and the atmosphere was purged with nitrogen for 10 minutes. The temperature was then increased at a rate of 15° C./min under a getter gas atmosphere until it reached 650° C. as shown below in reaction (XV).

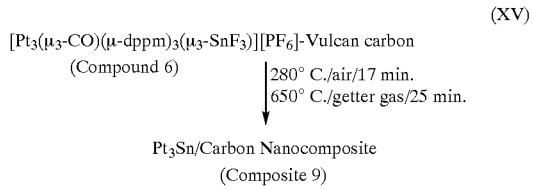

In reaction (XV) above, at 650° C., the atmosphere was changed to nitrogen and the temperature was maintained for 2 additional hours. The resulting black powder nanocomposite (Composite 9; 0.073 g) was analyzed by TEM and EDS, which showed that only $Pt_3Sn$ nanoparticles had been formed. EDS analysis: $PtL_\alpha$, $PtL_{62}$, $PtL_\gamma$, $PtM_\alpha$, $PtM_\beta$, $SnL_\alpha$, and $SnL_\beta$. Electron diffraction: interplanar d-spacings for only $Pt_3Sn$.

TEM analysis of Composite 7 revealed nanocrystalline particulates dispersed throughout the Vulcan carbon support. The thermal treatment that was used was one that left the molecular precursor metal stoichiometry which was somewhat impure. The particles were crystalline enough to produce an adequate selected area diffraction (SAD) ring pattern. PtSn and $PtP_2$ particle diameters exhibited a monomodal distribution of particle sizes ranging from 8.3 to 20.0 nm, with an average particle diameter of 12.7 nm measured by TEM, as indicated in Table 1 below.

TABLE 1

| Particle Diameter Range (nm) | Percentage (%) |
|---|---|
| 8.5–9.5 | 20 |
| 10.5–11.5 | 33 |
| 12.5–13.5 | 24 |
| 14.5–15.5 | 10 |
| 16.5–17.5 | 8 |
| 18.5–19.5 | 5 |

As indicated in FIG. 1, the energy dispersive spectrum (EDS) of Composite 7 indicated the presence of $PtL_\alpha$, $PtL_\beta$, $PtL_\gamma$, $PtM_\alpha$, $PtM_\beta$, $SnL_\alpha$, and $SnL_\beta$ emissions. EDS analysis also indicated the presence of $CuK_\alpha$ and $CuK_\beta$ emissions, due to the copper sample holder used for TEM analysis. These two copper emissions are therefore always present in the EDS spectra described herein.

The results of SAD analysis for nanocomposite 7 are listed in Table 2 which shows selected area electron diffraction d-spacings measured in Angstroms which were obtained for Composite 7. These data clearly identify the PtSn and $PtP_2$ crystalline phases and indicate that $Pt_3Sn$, $Pt_2Sn_3$1 or $PtSn_2$ crystalline nanoparticles were not present in Composite 7, as indicated in Table 3.

TABLE 2

| d-spacing - PtSn (published) (Å) | d-spacing - $PtP_2$ (published) (Å) | d-spacing observed (Å) | Percentage Error (%) |
|---|---|---|---|
| 2.157 | | 2.12 | 1.72 |
| | 2.010 | 2.01 | 0.00 |
| | 1.720 | 1.73 | 0.58 |
| 1.485 | | 1.50 | 1.01 |
| | 1.310 | 1.30 | 0.76 |
| | 1.270 | 1.27 | 0.00 |
| 1.203 | | 1.23 | 2.24 |
| | 1.164 | 1.17 | 0.52 |
| 1.132 | | 1.14 | 0.71 |
| | 1.097 | 1.06 | 3.37 |
| 0.781 | | 0.78 | 0.13 |

Table 3 below shows a comparison of PtSn and $PtP_2$ d-spacing data (in angstroms) obtained by SAD (and as shown in Table 2) with other known PtSn phases (top half) and a listing of important (non-PtSn and $PtP_2$) reflections not observed for Composite 7 (bottom half). The indication xxx in the top half of Table 3 indicates that no reflections matching the observed d-spacings are possible in the particular phase listed. In the bottom half of Table 3, the numbers in parentheses represent relative intensities of reflections for important indentifying reflections of the other known PtSn phases in Table 3 which were not observed in Composite 7.

TABLE 3

| d-spacings (observed) (Å) | $Pt_3Sn$ | $Pt_2Sn_3$ | $PtSn_2$ |
|---|---|---|---|
| 2.12 | xxx | | xxx |
| 1.50 | xxx | | |
| 1.23 | | | |
| 1.14 | | | |
| 0.78 | xxx | xxx | xxx |
| | 2.311 (100) | 2.442 (70) | 2.268 (80) |
| | 1.415 (35) | 1.612 (60) | 1.311 (100) |
| | 0.895 (35) | 1.011 (50) | 1.016 (80) |
| | 0.817 (53) | | 0.857 (100) |

Figure 2:
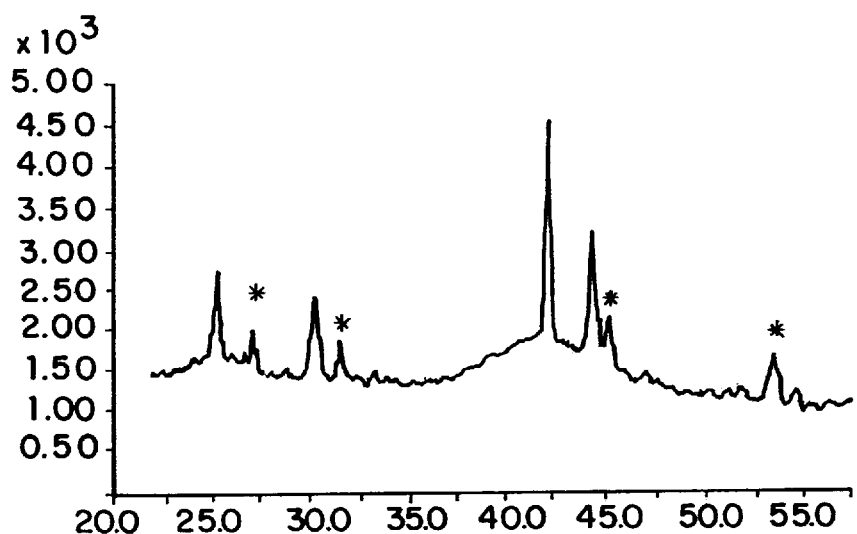
FIG. 2 is the x-ray diffraction (XRD) pattern of the nanocomposite Composite 7 formed in accordance with Example 1.

An XRD scan obtained using Composite 7, is shown in FIG. 2. The observed peaks match well in 2θ values and in relative intensities with the corresponding 100, 101, 102, and diffraction peaks of standard PtSn and the 111, 200, and 311 diffraction peaks of standard $PtP_2$. In conjunction with the data from EDS and SAD, the XRD data confirm that both PtSn and $PtP_2$ phases were formed in Composite 7 by heating in a hydrogen atmosphere.

A second series of doping and thermal treatments were performed using Compound 6. The treatments were performed over a wide temperature range using a getter gas (10 vol % $H_2$-90 vol % $N_2$) atmosphere to form Composite 8. The temperature of the reaction was varied from 500–650° C. in 50° C. increments. The resulting nanoparticles were characterized.

TEM analysis of Composite 8 formed at 650° C. revealed nanocrystalline particulates dispersed throughout the carbon support. Thermal reduction at 650° C. led to formation of both $Pt_3Sn$ and $PtP_2$ nanoparticles. Nanoparticles formed by thermal treatment at 500, 550, or 600° C. did not exhibit enough crystallinity to produce electron diffraction ring patterns.

As indicated in Table 4, $Pt_3Sn$ and $PtP_2$ particle diameter in Composite 8, formed at 650° C., exhibited a monomodal distribution. The particle sizes ranged from 3.0 to 15.3 nm, with an average particle diameter of 9.0 nm as measured by TEM.

TABLE 4

| Particle Diameter Range (nm) | Percentage (%) |
|---|---|
| 5.5–6.5 | 23 |
| 7.5–8.5 | 30 |
| 9.5–10.5 | 21 |
| 11.5–12.5 | 13 |
| 13.5–14.5 | 13 |

Figure 3:
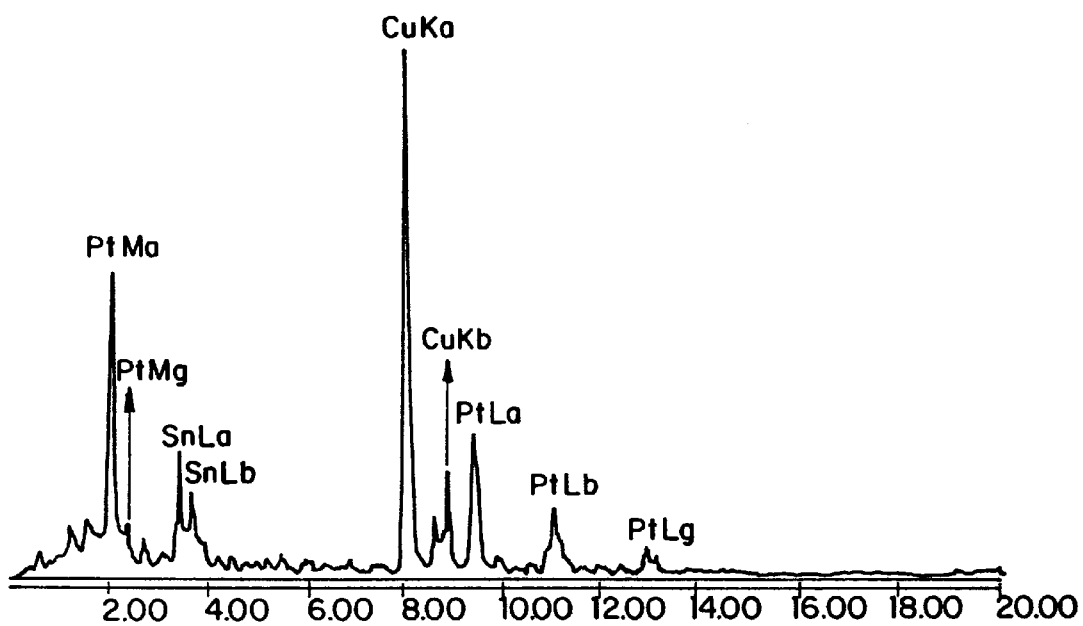
FIG. 3 is the EDS spectrum of the nanocomposite Composite 8 formed in accordance with Example 1.

The results of SAD analysis of Composite 8 formed at 650° C. are presented in Table 5 which shows that the observed d-spacings, measured in Angstroms, match those published for standard samples of $Pt_3Sn$ and $PtP_2$. These data clearly identify the $Pt_3Sn$ and $PtP_2$ crystalline phases and indicate that crystalline nanoclusters of PtSn, $Pt_2Sn_3$, or $PtSn_2$ were not present in Composite 8, as indicated in Table 6. As indicated in FIG. 3, the EDS analysis of Composite 8 revealed the presence $PtL_\alpha$, $PtL_\beta$, $PtL_\gamma$, $PtM_\alpha$, $PtM_\beta$, $SnL_\alpha$, and $SnL_\beta$ emissions.

TABLE 5

| d-spacing $Pt_3Sn$ (Published) (Å) | d-spacing $PtP_2$ (Published) (Å) | d-spacing (Observed) (Å) | Percentage Error (%) |
|---|---|---|---|
| | | 2.33 | 0.82 |
| | 2.010 | 2.02 | 0.50 |
| 1.415 | 1.420 | 1.43 | 1.06, 0.70 |
| 1.207 | | 1.21 | 0.25 |
| 0.895 | | 0.90 | 0.56 |

Table 6 below shows a comparison of $Pt_3Sn$ and $PtP_2$ d-spacing data, measured in angstroms as obtained by SAD and as set forth in Table 5 above, with other known PtSn phases (top in the top portion). In Table 6, xxx designates that no reflections matching the observed d-spacings were possible in the particular phase. A listing of important reflections for the other known PtSn phases which were not observed for Composite 8 are shown in the bottom portion of Table 6, with the intensities of those reflections noted in parentheses.

TABLE 6

| d-spacings (Observed) (Å) | PtSn | $Pt_2Sn_3$ | $PtSn_2$ |
|---|---|---|---|
| 2.33 | xxx | xxx | xxx |
| 1.43 | | | xxx |
| 1.21 | xxx | xxx | |
| 0.90 | xxx | xxx | |
| | 2.157 (100) | 2.168 (100) | 2.268 (80) |
| | 1.485 (80) | 1.519 (70) | 1.604 (100) |
| | 1.025 (40) | 1.142 (50) | 1.311 (100) |
| | | | 1.016 (80) |
| | | | 0.857 (100) |

Figure 4:
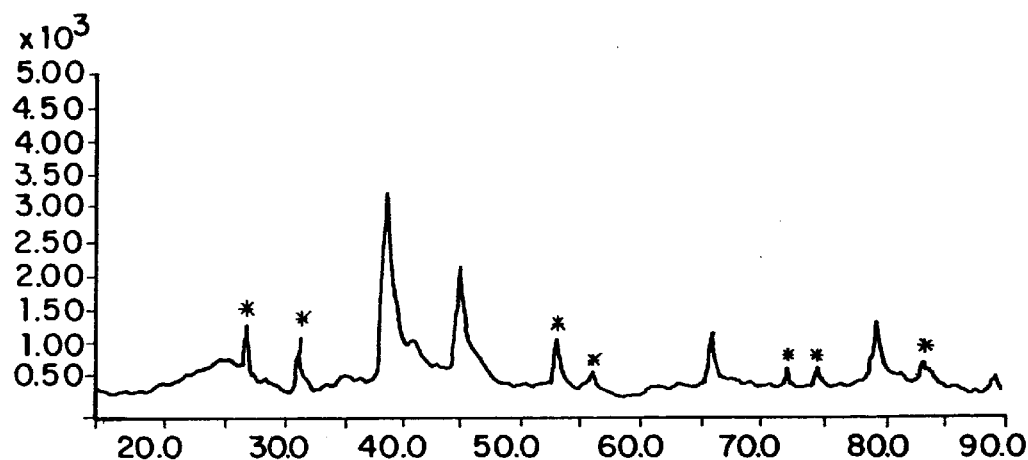
FIG. 4 is the XRD diffraction pattern of the nanocomposite Composite 8 formed in accordance with Example 1.

An XRD scan obtained using Composite 8 is shown in FIG. 4. The observed peaks match 2θ values and relative intensities of the corresponding 111, 200, 220, and 311 diffraction peaks of standard $Pt_3Sn$, as well as 110, 200, 220, 311, 222, 331, 420, 422, and 511 diffraction peaks of standard $PtP_2$. In conjunction with the data from EDS and SAD, the XRD data confirms that both $Pt_3Sn$ and $PtP_2$ phases were formed in Composite 8 by thermal reduction in a getter gas atmosphere.

A third series of doping and thermal treatments were performed using Compound 6. The treatments comprised thermal oxidation in air followed by thermal reduction in a getter gas atmosphere to yield Composite 9.

TEM analysis of Composite 9 revealed nanocrystalline particles dispersed throughout the Vulcan carbon support. Thermal oxidation to 280° C. followed by a thermal reduction up to 650° C. led to formation of crystalline $Pt_3Sn$ and prevented formation of $PtP_2$. The particles were sufficiently crystalline to produce an adequate SAD ring pattern. The particle sizes ranged from 4.2 to 14.2 nm, with an average particle diameter of 8.1 nm measured by TEM. As indicated in Table 7, $Pt_3Sn$ particle diameters exhibited a monomodal distribution.

TABLE 7

| Particle Diameter (nm) | Percentage (%) |
|---|---|
| 4.5–5.5 | 16 |
| 6.5–7.5 | 30 |
| 8.5–9.5 | 23.5 |

TABLE 7-continued

| Particle Diameter (nm) | Percentage (%) |
|---|---|
| 10.5–11.5 | 19 |
| 12.5–13.5 | 11.5 |

Figure 5:
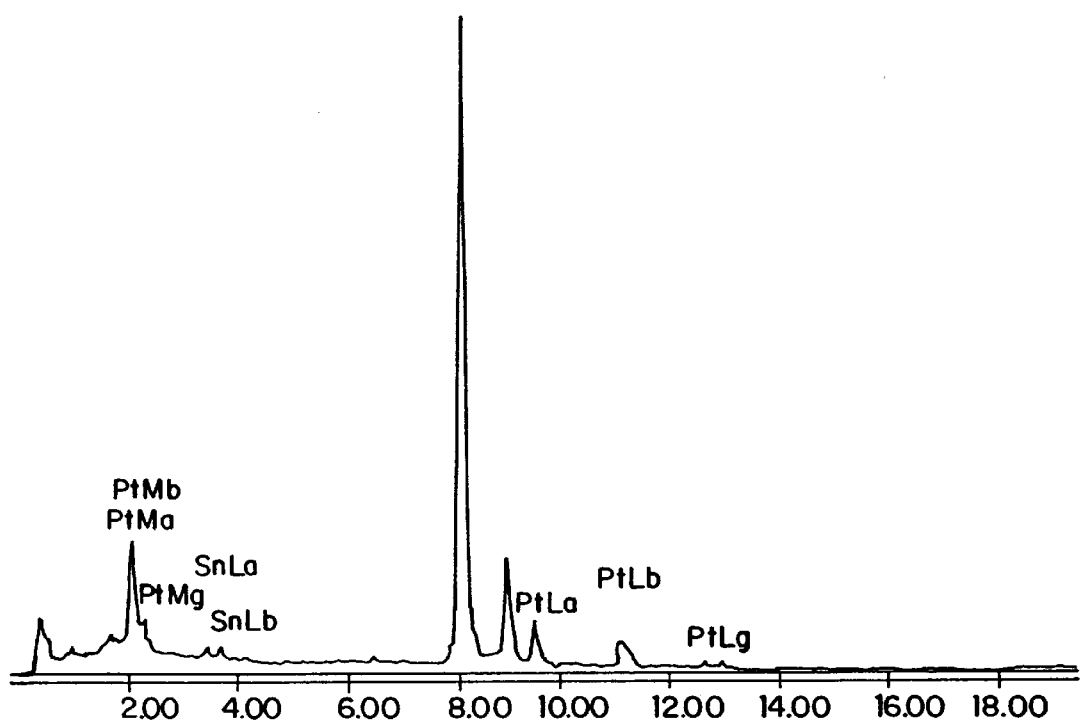
FIG. 5 is the EDS spectrum of the nanocomposite Composite 9 formed in accordance with Example 1.

The results of SAD analysis of Composite 9 are presented in Table 8. The observed d-spacings, measured in angstroms, match those published for a standard sample of $Pt_3Sn$. These data indicate that $Pt_3Sn$ was the only crystalline phase present in Composite 9 and further indicate that crystalline particles of PtSn, $Pt_2Sn_3$, $PtSn_2$, or $PtP_2$ were not present, as indicated in Table 9. As indicated in FIG. 5, EDS analysis of Composite 9 indicated the presence of $PtL_\alpha$, $PtL_\beta$, $PtL_\gamma$, $PtM_\alpha$, $PtM_\beta$, $SnL_\alpha$, and $SnL_\beta$ emissions and also demonstrate a 3:1 atomic ratio of Pt to Sn.

TABLE 8

| d-spacing $Pt_3Sn$ (Published) (Å) | d-spacing (Observed) (Å) | Percentage Error (%) |
|---|---|---|
| 2.311 | 2.32 | 0.39 |
| 2.001 | 2.03 | 1.45 |
| 1.415 | 1.43 | 1.06 |
| 1.207 | 1.22 | 1.08 |
| 0.895 | 0.89 | 0.56 |

A comparison of $Pt_3Sn$ d-spacing data, measured in angstroms and as set forth above in Table 8, with other known PtSn phases is shown in the top portion of Table 9 below where xxx indicates that no reflections matching the observed d-spacings were possible for the particular phase listed. The bottom of Table 9 below shows a list of important reflections for other known PtSn phases which are not $Pt_3Sn$ which were not observed for Composite 9.

TABLE 9

| d-spacing (Observed) (Å) | PtSn | $Pt_2Sn_3$ | $PtSn_2$ | $PtP_2$ |
|---|---|---|---|---|
| 2.32 | xxx | xxx | xxx | xxx |
| 2.03 |  | xxx | xxx |  |
| 1.43 | xxx |  | xxx |  |
| 1.22 |  | xxx |  |  |
| 0.89 | xxx | xxx | xxx |  |
|  | 2.157 (100) | 2.168 (100) | 2.268 (80) | 1.720 (65) |
|  | 1.485 (80) | 1.519 (70) | 1.604 (70) | 1.310 (55) |
|  | 1.025 (40) | 1.142 (50) | 1.311 (100) | 1.164 (55) |
|  |  |  | 1.016 (80) |  |
|  |  |  | 0.857 (100) |  |

Figure 6A:
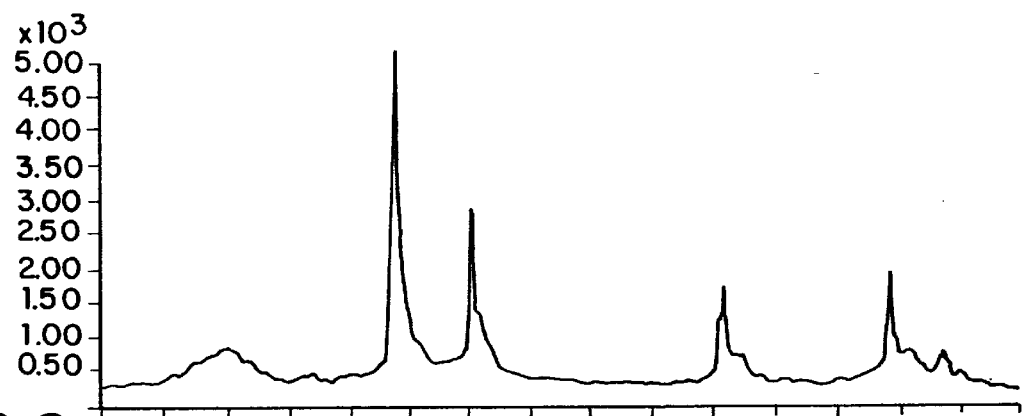
FIG. 6a–FIG. 6b is the XRD diffraction pattern of the nanocomposite Composite 9 formed in accordance with Example 1.
Figure 6B:
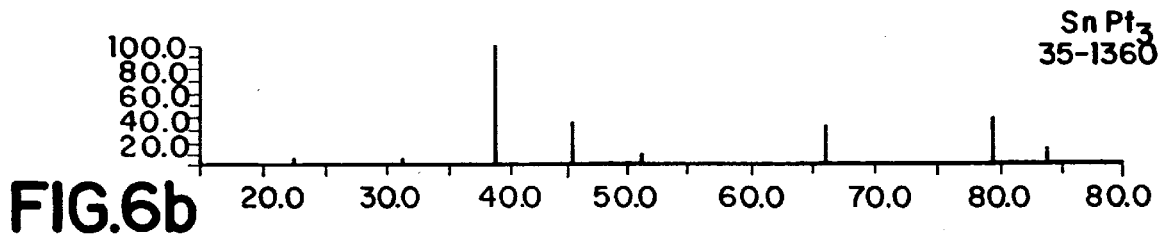

An XRD scan obtained using Composite 9 is shown in FIG. 6. The observed peaks match 2θ values and relative intensities of the corresponding 111, 200, 220, 311, and 222 diffraction peaks of standard $Pt_3Sn$. In conjunction with the data from EDS and SAD, the XRD data confirm that the only intermetallic phase present in Composite 9 is $Pt_3Sn$ though some small amount of metallic platinum is also evident. Presumably, mild thermal oxidation in air oxidizes the phosphorus present in Compound 5, thereby precluding the formation of $PtP_2$. In addition, thermal reduction under getter gas is sufficiently mild to prevent extensive loss of platinum from the nanocomposite.

EXAMPLE 2
Particulate Carbon Nanocomposites Comprising Pt/Au and $Pt_2W$ Nanoparticles:

Polymetallic precursors different from those in Example 1 were used in accordance with the method of the present invention to form platinum-rich nanocomposites in the form of $Pt_2W$ and PtAu alloys.

The materials and methods used in this Example are the same as those used in Example 1, with the exception of the use of chloro(triphenylphosphine) gold (I), and cyclopentadienyltungsten tricarbonyl dimer which were purchased from Strem Chemical, Inc. All other apparatus, materials, methods and rates of heating, and doping the carbon are the same as those described in Example 1.

Synthesis of tris[μ-[methylenebis[diphenylphosphine]-P:P′[$μ_3$-(triphenylphosphine)gold]triplatinum ($I^+$) hexafluorophosphate ($1^-$) (Compound 10) was performed as reported by Payne et al., Inorg. Chem. 30:4052 (1991), herein incorporated by reference, and as represented by the following reaction sequence (XVI):

(XVI)

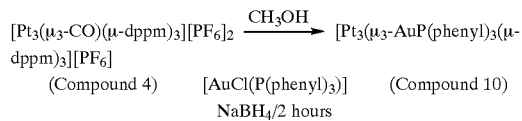

[$Pt_3(μ_3$-CO)(μ-dppm)$_3$][$PF_6$]$_2$ $\xrightarrow{CH_3OH}$ [$Pt_3(μ_3$-AuP(phenyl)$_3$(μ-dppm)$_3$][$PF_6$]

(Compound 4)      [AuCl(P(phenyl)$_3$)]      (Compound 10)
                  $NaBH_4$/2 hours Adsorption of Compound 10 onto Vulcan XC-72R Carbon An aliquot of Compound 10 (0.023 g, 9.82 pmol) was added to a 250 ml beaker along with Vulcan XC-72R carbon (0.06 g, 3.00 mmol). A Teflon™-coated magnetic stirring bar and 50 ml of acetone were added to the beaker. The solution was stirred overnight. The solution was centrifuged, and acetone was decanted from the solid. The molecularly doped Vulcan carbon was allowed to air dry for 72 hours to yield Compound 11 (0.08 g).

Thermal Oxidation of Compound 11 in an Air Atmosphere Followed By Thermal Reduction in a Getter Gas Atmosphere Reaction sequence (XVII)–(XVIII), below, shows formation of Compound 11 as described above and subsequent oxidation and thermal reduction of Compound 11 to form Composite 12.

(XVII)

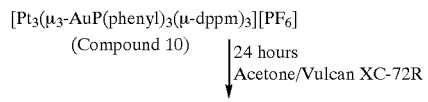

[$Pt_3(μ_3$-AuP(phenyl)$_3$(μ-dppm)$_3$][$PF_6$]
(Compound 10)   | 24 hours
                | Acetone/Vulcan XC-72R (XVIII)

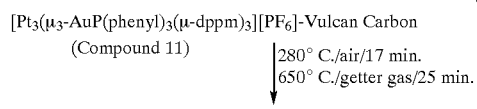

[$Pt_3(μ_3$-AuP(phenyl)$_3$(μ-dppm)$_3$][$PF_6$]-Vulcan Carbon
(Compound 11)   | 280° C./air/17 min.
                | 650° C./getter gas/25 min.

PtAu/Carbon Nanocomposite
(Composite 12)

In accordance with the above reaction sequence, an aliquot of Compound 11 (0.08 g) was heated to 280° C. at a rate of 15° C./min in an air atmosphere. After the temperature had reached 280° C., the temperature was maintained, the atmosphere was purged with nitrogen and the temperature was maintained 10 additional minutes. The temperature was then increased at a rate of 15° C./min under a getter gas atmosphere until it reached 650° C. At 650° C., the atmosphere was changed to nitrogen and this temperature was maintained for 2 hours. The resulting black powder (Composite 12; 0.047 g) was analyzed by TEM and EDS, which indicated that nanoparticles of Pt and Au had formed. EDS analysis: $PtL_\alpha$, $PtL_\beta$, $PtL_\gamma$, $PtM_\alpha$, $PtM_\beta$, $PtM_\gamma$, $AuL_\alpha$, $AuL_\beta$, $AuL_\gamma$, $AuM_\alpha$, and $AuM_\beta$.

Synthesis of tris[μ-[methylenebis[diphenylphosphine]-P:P']]-[(pentahapto-cyclopentadienyl) tungstencarbonyl]triplatinum(1+) Hexafluorophosphate(1−) (Compound 13)

Reaction sequence (XIX), below shows the synthesis of Compound 13.

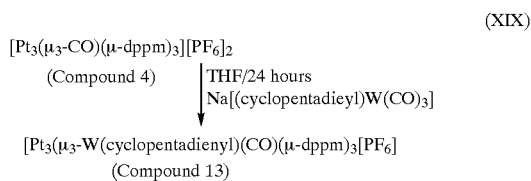

(XIX)

[Pt$_3$(μ$_3$-CO)(μ-dppm)$_3$][PF$_6$]$_2$
(Compound 4)
    | THF/24 hours
    | Na[(cyclopentadieyl)W(CO)$_3$]

[Pt$_3$(μ$_3$-W(cyclopentadienyl)(CO)(μ-dppm)$_3$[PF$_6$]
(Compound 13)

In accordance with the above reaction sequence, cyclopentadienyltungsten tricarbonyl dimer (0.100 g, 0.150 mmol) was added to Na/Hg amalgam (prepared by adding 2 g of Na to 7 ml of Hg) and 10 ml THF. The reaction mixture was allowed to stir under a nitrogen atmosphere for 2 hours. The bright green solution was filtered through cotton into a clean flask purged with nitrogen. Next, (μ$_3$-carbonyl)tris[μ-bis(diphenyl-phosphino)methane)-triangulo-triplatinum(2+) hexafluorophosphate (0.300 g, 0.142 mmol) was added, forming a blood-red solution. The solution was stirred for 20 hours, and the solvent was removed under reduced pressure. The solid was redissolved in THF and chromatographed on a thin-layer chromatography (TLC) plate using CH$_2$Cl$_2$ as the mobile phase. This yielded a deep red solid (Compound 13; 0.247 g, 73% yield), which had the following properties: mp 196–199° C.; $^1$H NMR (CD$_2$Cl$_2$) δ 5.33 (s, cyclopentadienyl ring), 6.9–7.7 (m, aromatic).

Adsorption of Compound 13 onto Vulcan XC-72R Carbon

Reaction sequence (XX)–(XXI) shows the adsorption of Compound 13 onto Vulcan XC-72R carbon to form Compound 14, and the following thermal reduction of Compound 14 to form a platinum/tungsten (Pt$_2$W) nanocomposite.

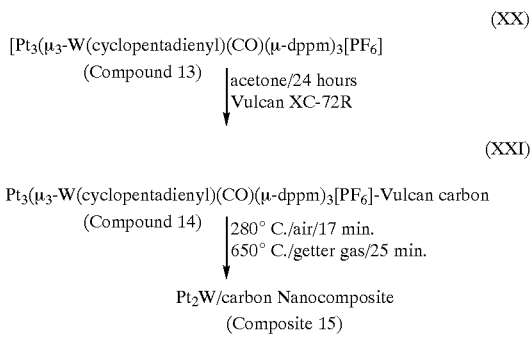

(XX)

[Pt$_3$(μ$_3$-W(cyclopentadienyl)(CO)(μ-dppm)$_3$[PF$_6$]
(Compound 13)
    | acetone/24 hours
    | Vulcan XC-72R (XXI)

Pt$_3$(μ$_3$-W(cyclopentadienyl)(CO)(μ-dppm)$_3$[PF$_6$]-Vulcan carbon
(Compound 14)
    | 280° C./air/17 min.
    | 650° C./getter gas/25 min.

Pt$_2$W/carbon Nanocomposite
(Composite 15)

In accordance with reaction (XX), an aliquot of Compound 13 (0.100 g, 46.3 μmol) was added to a 250 ml beaker along with Vulcan XC-72R carbon (0.300 g, 0.025 mol). A Teflon™-coated magnetic stirring bar and 60 ml of acetone were added to the beaker. The solution was stirred overnight. The solution was centrifuged, and acetone was decanted from the solid. The doped Vulcan carbon was allowed to air dry for 72 hours to yield Compound 14 (0.314 g).

In accordance with above-reaction (XXI), a sample of Compound 14, (0.080 g) was heated to 280° C. at a rate of 15° C./min in an air atmosphere. After the temperature had reached 280° C., the temperature was maintained and the atmosphere was changed to nitrogen by purging for 10 minutes. The temperature was then increased at a rate of 15° C./min under a getter gas atmosphere until it reached 650° C. At 650° C., the atmosphere was changed to nitrogen and the temperature was maintained for 2 hours. The resulting black powder nanocomposite (Composite 15; 0.058 g) was analyzed by TEM and EDS, which indicated that both Pt$_2$W and PtP$_2$ nanoparticles had been formed. EDS analysis: PtL$_\alpha$, PtL$_\beta$, PtL$_\gamma$, PtM$_\alpha$, PtM$_\beta$, PtM$_\gamma$, WL$_\beta$, WM$_\alpha$, and WM$_\beta$.

The results of the above syntheses are presented as follows. Carbon nanocomposites comprising nanoparticles of each of Pt and Au were synthesized by oxidative thermal treatment in air of a composite comprising Vulcan carbon and a known Pt$_3$Au molecular precursor as an adsorbate followed by reductive thermal treatment in getter gas. The Pt$_3$Au precursor cluster Compound 10, was synthesized from Compound 4 as shown in reaction (XVI) above.

TEM analysis of Composite 12 revealed nanocrystalline particles dispersed throughout the Vulcan carbon support. Thermal oxidation to 280° C. followed by thermal reduction to 650° C. led to the formation of a mixture of crystalline Pt and crystalline Au nanoparticles.

As indicated in Table 10, Pt and Au particle diameters exhibited a monomodal distribution. The particle sizes ranged from 3.4 to 14.6 nm, with an average particle diameter of 8.6 nm as measured by TEM.

TABLE 10

| Particle Size Range (nm) | Percentage (%) |
|---|---|
| 3.5–4.5 | 9.5 |
| 5.5–6.5 | 18 |
| 7.5–8.5 | 19.5 |
| 9.5–10.5 | 27.5 |
| 11.5–12.5 | 18 |
| 13.5–14.5 | 7.5 |

Figure 7:
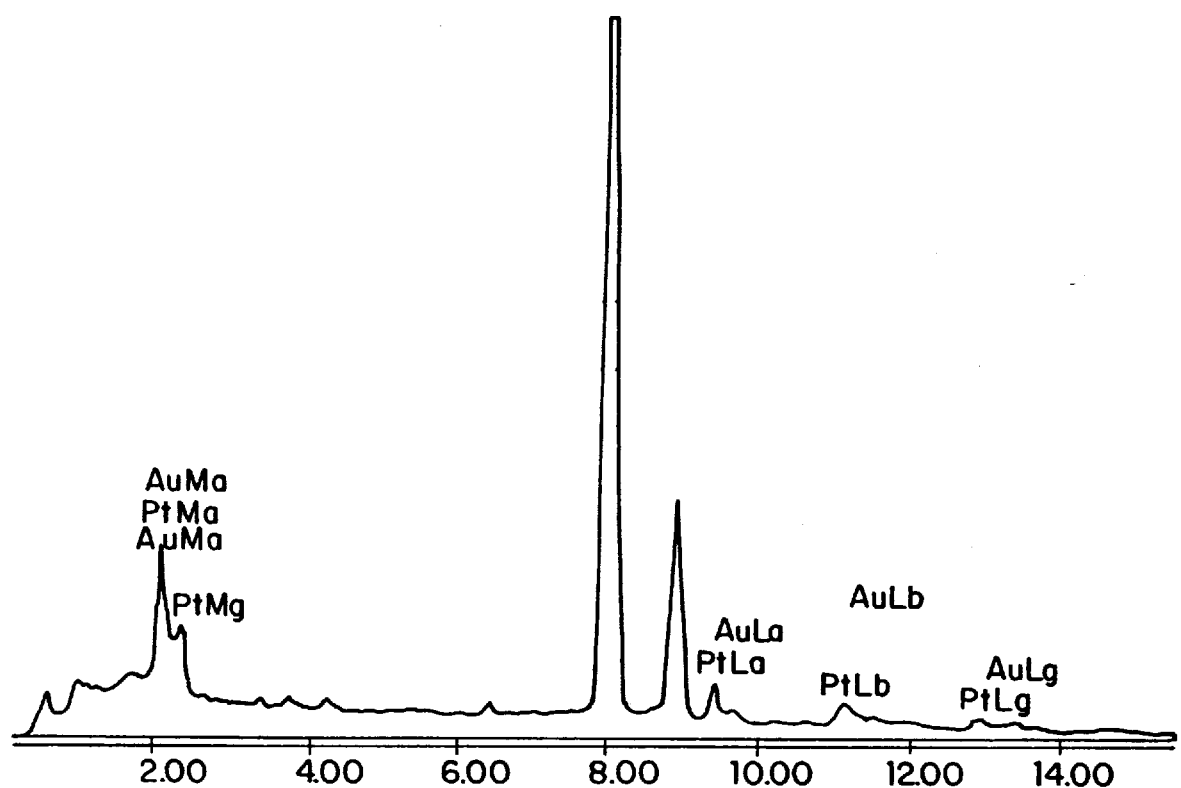
FIG. 7 is the EDS spectrum of the nanocomposite Composite 12 formed in accordance with Example 2.

As indicated in FIG. 7, the energy dispersive spectrum of Composite 12 revealed the presence of PtL$_\alpha$, PtL$_\beta$, PtL$_\gamma$, PtM$_\alpha$, PtM$_\beta$, PtM$_\gamma$, AuL$_\alpha$, AuL$_\beta$, AuL$_\gamma$, AuM$_\alpha$, and AuM$_\beta$, emissions and the spectra also exhibited a 3:1 atomic ratio of Pt to Au.

Figure 8:
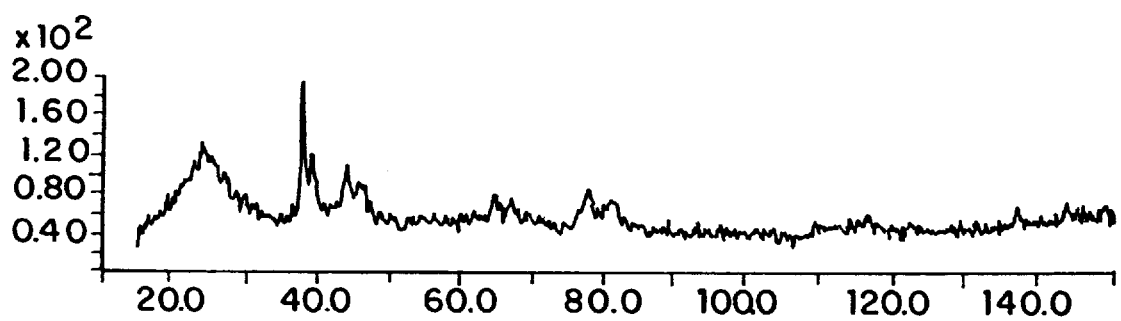
FIG. 8 is the XRD diffraction pattern of the nanocomposite Composite 12 formed in accordance with Example 2.

An XRD scan obtained using Composite 12 is shown in FIG. 8. The observed peaks match 2θ values and relative intensities of the corresponding 111, 200, 220, 222, and 321 diffraction peaks of standard Au as well as the 111, 200, 220, and 311 diffraction peaks of standard Pt. By using standard techniques to find the unit cell size of the alloy, it was calculated that the unit cell was approximately 0.407 nm. This value matches the value of the unit cell size of Au (0.407 nm). From this calculation and the XRD data, the nanoparticles of Composite 12 were determined not to comprise a Pt$_3$Au alloy phase, but separate Pt and Au phases instead. Upon thermal treatment, Compound 11 metal atoms apparently phase-separated into the elemental forms of Pt and Au. While the results are good in comparison with prior art attempts, gold is much more difficult to alloy in such nanoparticles.

Carbon nanocomposites comprising nanoparticles of Pt$_2$W were synthesized by oxidative thermal treatment in air followed by reductive thermal treatment in getter gas. The Pt$_3$W molecular precursor, Compound 13, was synthesized in accordance with reaction (XIX) above.

TEM analysis of Composite 15 revealed nanocrystalline particles dispersed throughout the Vulcan carbon support. Thermal oxidation to 280° C. followed by thermal reduction to 650° C. led to the formation of crystalline Pt$_2$W and a small amount of PtP$_2$ as nanoparticles. Bright-field imaging of Composite 15 indicated the presence of crystalline nanoclusters dispersed throughout the support. The particulate features exhibited sharp edges and some exhibited a hexagonal projection.

As indicated in Table 11, $Pt_2W$ particle diameter exhibited a monomodal distribution of particle sizes ranging from 10 to 38.3 nm. The average particle diameter of Composite 15 was 17.0 nm as measured by TEM.

TABLE 11

| Particle Diameter Range (nm) | Percentage (%) |
| --- | --- |
| 10.5–11.5 | 6.5 |
| 12.5–13.5 | 13 |
| 14.5–15.5 | 22.5 |
| 16.5–17.5 | 33 |
| 13.5–19.5 | 16.5 |
| 20.5–21.5 | 8.5 |

Figure 9:
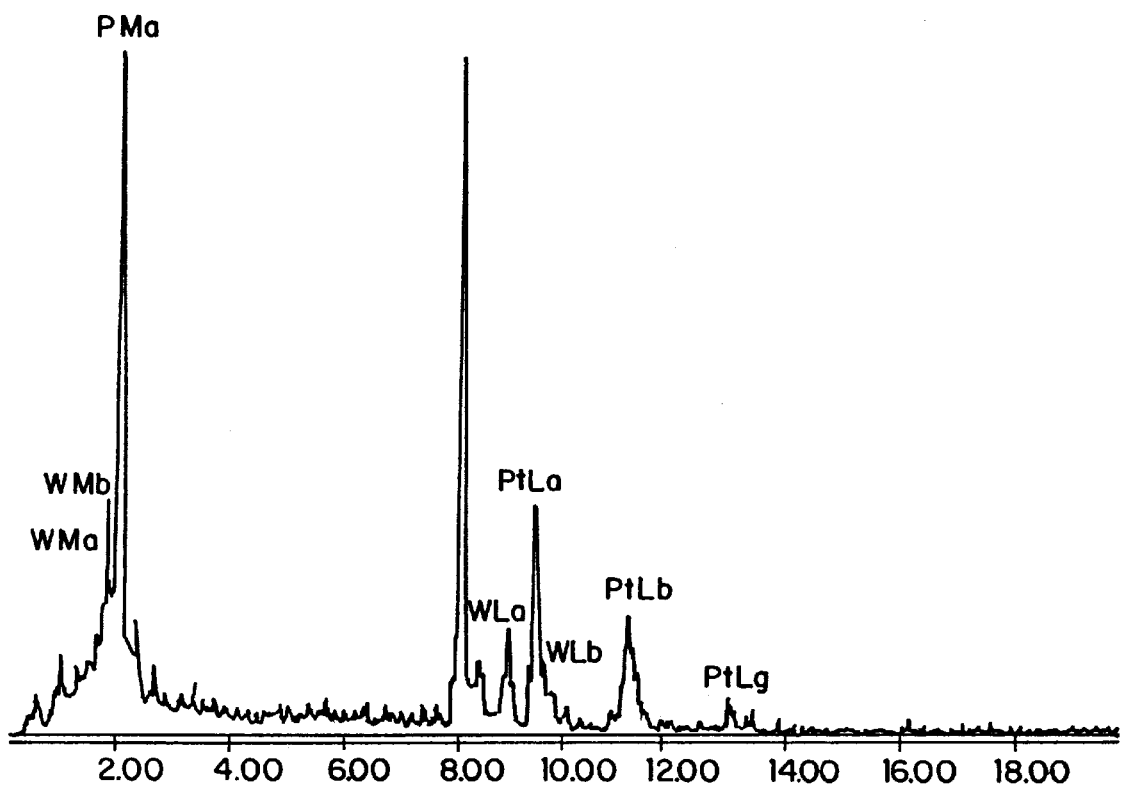
FIG. 9 is the EDS spectrum of the nanocomposite Composite 15 formed in accordance with Example 2.

As indicated in FIG. 9, EDS analysis of Composite 15 revealed the presence of $PtL_\alpha$, $PtL_\beta$, $PtL_\gamma$, $PtM_\alpha$, $PtM_\beta$, $WL_\gamma$, $WM_\alpha$, and $WM_\beta$ emissions and also indicated a 3:1 atomic ratio of Pt to W. This Pt/W ratio is the result of the presence of nanoparticles comprising $PtP_2$ and amorphous platinum due to phase separation of the $Pt_3W$ core. From these data, it can be concluded that the $Pt_3W$ alloy, which was the core stoichiometry of the molecular precursor, was not formed, but rather phase separation of $Pt_2W$ occurred to yield nanoparticles comprising the more stable intermetallic phase. Crystalline Pt or W nanoparticles were not observed.

Figure 10:
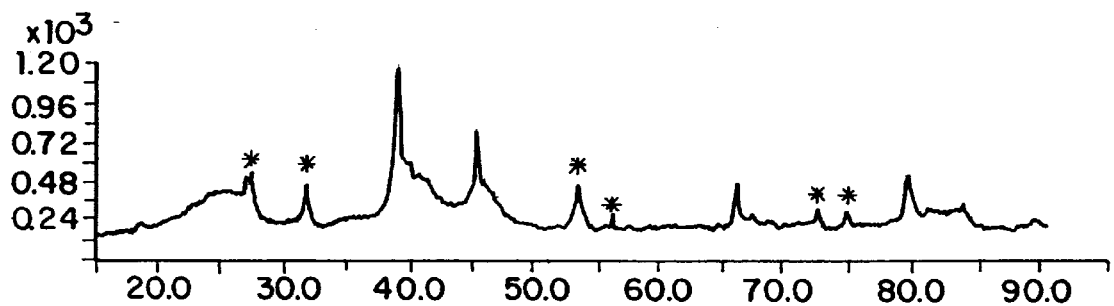
FIG. 10 is the XRD diffraction pattern of the nanocomposite Composite 15 formed in accordance with Example 2.

An XRD scan obtained using Composite 15 is shown in FIG. 10. The observed peaks match 2θ values and relative intensities of the corresponding 101, 002, 132, and 231 diffraction peaks of standard $Pt_2W$ and 111, 200, 311, 222, 331, and 420 diffraction peaks of standard $PtP_2$. In conjunction with the data from EDS, the XRD data confirm that only $Pt_2W$ intermetallic nanoparticles and a small amount of $PtP_2$ nanoparticles were present in Composite 15.

These data suggest that the nanocomposite phase, $Pt_3W$, separates to the more stable $Pt_2W$ intermetallic phase during thermal treatment. Excess platinum was apparently present as amorphous platinum, as indicated by peak integration in the EDS spectra.

Using techniques described herein, mixed-metal cluster and metal phosphide nanocomposites have been prepared and characterized. Nanocomposites that have been prepared are summarized in Table 12 along with the particle size and heating conditions for synthesizing those compounds.

TABLE 12

| Nanocomposite Phase | Particle Size (nm) | Heating Conditions |
| --- | --- | --- |
| $PtSn/PtP_2$ | 12.7 | $H_2$, 700° C., 2 hours |
| $Pt_3Sn/Pt_2$ | 9.0 | Getter Gas, 650° C., 40 min., $N_2$, 650° C., 2 hours |
| $Pt_3Sn$ | 8.1 | Air, 280° C., 17 min Getter Gas, 650° C., 25 min., $N_2$, 650° C., 2 hours |
| Pt/Au | 8.6 | Air, 280° C., 17 min Getter Gas, 650° C., 25 min., $N_2$, 650° C., 2 hours |
| $Pt_2W/PtP_2$ | 17.0 | Air, 280° C., 17 min., Getter Gas, 650° C., 25 min, $N_2$, 650° C., 2 hours |

A goal of certain studies described herein was to make a pure, highly crystalline $Pt_3Sn$/carbon nanocomposite. A known molecular precursor was chosen and synthesized. The precursor was then adsorbed onto the surface of Vulcan XC-72R carbon. Thermal treatment of this composite under hydrogen led to the production of nanoparticulate PtSn and $PtP_2$. The reductive conditions were determined to be too severe and caused phase separation. To avoid this result, the reductive conditions were lessened. The reductive treatment was performed under a getter gas atmosphere (10% by volume $H_2$, 90% by volume $N_2$). This led to the formation of the desired $Pt_3Sn$ phase, but the resulting nanocomposite consisted of both $Pt_3Sn$ and $PtP_2$ nanoparticulates.

To minimize formation of the undesired $PtP_2$, the thermal treatment was altered by adding a oxidative treatment step before the reductive treatment step in order to oxidize any phosphorus which was present to a phosphorus oxide prior to reductive treatment. Phosphorus oxidation was achieved by thermally treating the preparation in an air atmosphere and thereafter performing the reductive treatment in a getter gas atmosphere. These steps led to the successful formation of a substantially chemically pure $Pt_3Sn$ nanocomposite. This process was then performed using other polymetallic precursors.

EXAMPLE 3

Rapid Synthesis of Pd, Pt or $Pt_1Ru_1$ Nanoparticles on a Carbon Support using Metallic and Polymetallic Precursors and Microwave Irradiation Metal/carbon nanocomposites of commercial importance were prepared in less than one minute of reaction time by microwave irradiation of conductive carbon powder supported metallic or polymetallic precursors. Pd or Pt halide complexes were used as precursors for nanoparticles comprising those metals, while a non-cluster-type Pt—Ru bimetallic precursor was used as a single-source precursor to generate nanoparticles having the composition $Pt_1Ru_1$. Average metal particle sizes for these Pd, Pt, and $Pt_1Ru_1$ nanoparticles were 7.0, 5.3, and 2.8 nm, respectively by TEM. Microwave irradiation can be thus used for the rapid synthesis of metal or metal alloy nanoparticles from single precursors on a conductive carbon support. Non-cluster, bimetallic precursors for the synthesis of Pt—Ru nanoparticles having a controlled alloy stoichiometry of commercial importance were formed.

Vulcan carbon nanocomposites were prepared comprising nanoparticles of Pd metal, Pt metal, or a $Pt_1Ru_1$ metal alloy. The simple halide complexes, $Na_2[PdCl_4]$ or $K_2[PtCl_4]$, were used as single metal precursors of Pd or Pt metal particles, respectively, and the non-cluster, bimetallic complex, [(trihapto:trihapto-2,7-dimethyloctadienediyl)-Ru$(Cl)(\mu$-$Cl)_2$Pt(triethylphosphine)(Cl)] was used as a single source bimetallic precursor of $Pt_1Ru_1$ nanoparticles. The bimetallic precursor was prepared according to the procedure reported for the preparation of the corresponding complex containing tributylphosphine as a ligand. Severin et al., *Inorg. Chim. Acta* 240:339 (1995). Prepared [(trihapto:trihapto-2,7-dimethyloctadienediyl)Ru(Cl) (P-Cl)$_2$Pt(triethylphosphine)(Cl)] had the following properties: brown powder; mp 144–146° C.; $^1$H NMR [300 MHZ, $CDCl_3$] δ 1.24 (δ of t, $CH_2CH_3$, 9H), 1.86 (δ of q, $CH_2CH_3$, 6H), 2.33 (s, $CH_2CHC(CH_3)CH_2$, 3H), 2.35 (s, $CH_2CHC(CH_3)CH_2$, 3H), 2.40 (m, $CH_2CHC(CH_3)CH_2$, 2H), 2.5–2.8 (m, $CH_2CHC(CH_3)CH_2$, 2H), 4.53 (m, $CH_2CHC(CH_3)CH_2$, 1H), 4.97 (s, $CH_2CHC(CH_3)CH_2$, 1H), 4.97 (s, $CH_2CHC(CH_3)CH_2$, 1H), 5.35 (s, $CH_2CHC(CH_3)CH_2$, 1H), 5.54 (s, $CH_2CHC(CH_3)CH_2$, 1H), 6.01 (s, $CH_2CHC(CH_3)CH_2$, 1H); $^{13}$C NMR [75 MHZ, $CDCl_3$] δ 7.58 (δ, $CH_2CH_3$, $^2J_{PC}$=3.2 Hz), 14.2 (d, $CH_2CH_3$), $^1J_{PC}$=40.5 Hz); 19.8, 20.4 ($CH_2CHC(CH_3)CH_2$), 34.1, 34.9 ($CH_2CHC(CH_3)CH_2$), 83.2, 85.5 ($CH_2CHC(CH_3)CH_2$), 93.9, 94.1 ($CH_2CHC$ (CH$_3$)CH$_2$), 124.7, 126.9 (CH$_2$CHC(CH$_3$)CH$_2$); $^{31}$P NMR [121 MHZ, CDCl$_3$] δ 8.39 ($^1$J$_{PtP}$=3784 Hz).

Anal. for C$_{16}$H$_{31}$,Cl$_4$PPtRu: C, 27.76; H, 4.51; P, 4.47. Found: C, 27.55; H, 4.64; P, 4.37.

Each precursor was deposited in the form of an acetone or aqueous solution onto Vulcan carbon XC-72R by evaporation of solvent. Excess solvent was removed by rotoevaporation. Precursor loadings were arbitrarily selected to be 10 weight percent total metal for this study. Samples of these molecularly doped carbon composites having a mass of about 0.05 grams were placed inside a one-half dram glass vial, filling it to a depth about 1 cm. The assembly was then embedded within a 1 cm deep layer of Vulcan carbon within a two dram glass vial. The outer volume of carbon powder had a mass of about 0.15 grams and was used as a thermal bath for more efficient microwave heating. The reaction assembly was placed into a 100 ml glass beaker to afford mechanical stability.

Thermal treatment was accomplished using a microwave oven (Sharp Corporation, Model R-2M52B) operating at 2.45 GHz with a fixed power level of 600 Watts. Control studies using untreated Vulcan carbon indicated that the temperature of the carbon powder present within the inner vial increased rapidly upon microwave irradiation. Using successive irradiation periods of 15 seconds duration, the temperature of the inner carbon mass, as measured by thermocouple immersion, was 233° C. after one irradiation period, 405DC after two irradiation periods, and 511° C. following three irradiation periods. Imprudently prolonged microwave irradiation can lead to softening of the glass vials, and caution in using glass vials is therefore recommended. A beaker of cold water was placed within the microwave oven to protect the oven from irradiation damage.

Thermal treatment of the molecular precursor/carbon nanocomposites by microwave irradiation was conducted under an air atmosphere to oxidatively degrade the precursor complex, followed by irradiation under getter gas to reduce the metal ions to metal. Between repetitive oxidative thermal treatments, the air atmosphere above the inner sample was replenished by mild flushing. The reaction assembly was evacuated to about 0.01 mm Hg and filled with nitrogen gas between oxidative and reductive thermal treatments to preclude formation of potentially explosive air/hydrogen mixtures. Getter gas was supplied using a partially filled Helium-grade balloon at a pressure slightly above one atmosphere. The filled balloon was affixed to the mouth of the two-dram outer vial using tape.

The resulting metal or metal alloy/carbon nanocomposites were characterized by TEM, EDS, and powder XRD using a Philips CM20T instrument for TEM and a Scintag X1 Diffraction System for XRD. Particle-size distributions, average particle diameters, and median particle sizes were determined by TEM analysis. XRD patterns were used to confirm the crystallinity and identity of the nanocrystal substance. In addition, a volume-weighted average nanocrystal particle size was obtained from XRD peak widths using Scherrer's equation. Prior to peak width measurements diffraction peaks were corrected for background scattering and were stripped of the Kα$_2$ portion of the diffraction intensity. EDS spectral analysis was used to confirm the elemental composition of the nanoparticles for elements heavier than fluorine.

Microwave irradiation of the molecular precursors and particulate carbon in air (15 seconds irradiation on; 45 seconds irradiation off; 10 seconds irradiation on) followed by an identical reduction treatment using the same heating regimen in getter gas yielded the Pd, Pt or Pt$_1$Ru$_1$/carbon nanocomposites. TEM analysis revealed good contrast between the crystalline, nearly spheroidal metal nanoparticles and the amorphous carbon matrix. Metal nanoparticle sizes for these nanocomposites exhibited monomodal particle-size distributions. The average particle size (standard deviation; median diameter) for each nanocomposite was determined: Pd, 7.0 (2.9; 6.6) nm; Pt, 5.3 (2.7; 4.6) nm; Pt$_1$Ru$_1$, 2.8 (0.5; 2.8) nm. Particles less than about 15 Å in diameter were not easily counted.

XRD diffraction patterns for the three nanocomposites are shown in FIGS. 11, 12 and 13. XRD patterns for the Pd and Pt/carbon nanocomposites indicated the presence of crystalline NaCl and KCl. These salts were removed by aqueous washing. XRD scans of the Pd or Pt/carbon nanocomposites revealed the patterns characteristic of the pure metals. XRD scans of the Pt$_1$Ru$_1$/carbon nanocomposite were consistent with a face-centered cubic cell having a lattice constant of 3.867 (0.005) Å. This pattern is the pattern predicted for a 1:1 solid solution of Pt and Ru. Radmilovic et al., J. Catal. 154:98 (1995). The widths of the XRD peaks reflect the small sizes of the nanocrystalline phases and indicate the following calculated average particle sizes (standard deviations): Pd, 8.3 (1.2) nm; Pt, 9.4 (2.4) nm; Pt$_1$Ru$_1$, 2.1 (0.7) nm.

A close correspondence between average particle sizes determined from TEM and XRD measurements is consistent with a nanocrystal size distribution lacking significant numbers of unusually large particles. The presence of even a small fraction of atypically large particles is reflected in larger average particle sizes determined by XRD relative to average sizes measured by TEM. For such distributions, the median particle size would also be greater than the number-average particle size.

EDS spectra revealed X-ray emissions from the expected metals and essentially complete loss of chlorine from the precursors. Integrated EDS intensities confirmed a Pt to Ru atomic ratio of 1.0 in the Pt$_1$Ru$_1$/carbon nanocomposite.

Metal nanocrystal formation presumably occurred by thermal diffusion of incipient metal atoms or polyatomic clusters of metal atoms along a complex carbon surface and eventual agglomeration to form nanocrystals. Nanocrystal average size was affected by total irradiation time. Doubling the duration of each irradiation period yielded average nanoparticle diameters (standard deviation; median diameter) of 7.1 (3.1; 6.7) nm for Pd, 8.7 (6.0; 6.8) nm for Pt, and 3.6 (0.7; 3.5) nm for Pt$_1$Ru$_1$ as determined by TEM, and average nanoparticle diameters (standard deviation) of 52.7 (13.4) nm for Pd, 31.1 (0.6) nm for Pt, and 2.1 (0.6) nm for the Pt$_1$Ru$_1$ nanocrystals, as determined by XRD. Doubling the total irradiation time increased the fraction of larger particles, as predicted by diffusion-controlled growth mechanistic models. Liu et al., *J. Appl. Phys.* 68:28 (1990). The fraction of atypically large nanoclusters formed under prolonged heating was greater for the Pd and Pt nanocomposites than for the Pt$_1$Ru$_1$ nanocomposite.

Nanoparticles average size was also affected by the depth of the precursor in the glass vial. Pt$_1$Ru$_1$ nanoparticles formed within the top half of the sample had an average diameter of 3.9 (0.6) nm, while those formed in the bottom half had a slightly larger average diameter of 4.7 (0.8) nm. These results indicate that uneven heating of the reaction sample probably occurred due to a carbon-bath effect and may be minimized by using a thinner layer of sample or through other techniques.

The results of the experiments presented in this Example indicate that nanoparticle size distributions for these metal or metal alloy/carbon nanocomposites are affected by the duration of the microwave irradiation and the geometry of the reaction assembly. Manipulation of these experimental parameters provides considerable control over nanocrystal average size and at least some control over the width of particle-size distributions.

Production of metal/carbon nanocomposites by this method on a larger scale is possible using commercial microwave irradiation technology, such as the microwave technology described by Sutton et al., Eds., Microwave Processing of Materials, MRS Symposium Proceedings, Vol. 124, Materials Research Society, Pittsburgh (1988).

EXAMPLE 4
Preparation of a Carbon Supported Catalyst of Metal Composition PtRu The binuclear non-cluster precursor, Pt(triphenylphosphine)(Cl)($\mu$-Cl$_2$)Ru(Cl)(trihapto:trihapto-2,7-dimethyloctadienediyl), in an amount of 0.08 g was dissolved in 15 ml of acetone. The resulting solution was stirred with 0.24 g of carbon support. Deposition of the precursor onto the carbon support was achieved by removal of the liquid phase by evaporation. The resulting precursor/carbon composite was placed into a tube furnace and treated thermally under the following conditions: 25 to 280° C. under air; 280 to 650° C. under getter gas; anneal under N$_2$ gas at 650° C. for 2.5 hours, after which time the sample was cooled to room temperature.

EXAMPLE 5
Preparation of a Carbon Supported Catalyst of Metal Composition PtRu The binuclear non-cluster precursor, Pt(triphenylphosphine)(Cl)($\mu$-Cl$_2$)Ru(Cl)(trihapto:trihapto-2,7-dimethyloctadienediyl), in an amount of 0.10 g, was dissolved in 15 ml of acetone. The resulting solution was stirred with 0.18 g of carbon support. Deposition of the precursor onto the carbon support was achieved by removal of the liquid phase by evaporation. The resulting precursor/carbon composite was placed into a tube furnace and is treated thermally under the following conditions: 25 to 350° C. under air; 350 to 650° C. under getter gas; anneal under N$_2$ gas at 650° C. for 10 minutes, after which time the sample was cooled to room temperature. A second deposition/thermal treatment cycle was performed using 0.13 g of the precursor complex followed by thermal treatments of 25 to 350° C. under air, 350 to 650° C. under getter gas, and anneal at 650° C. for 85 minutes under nitrogen, after which time the sample was cooled to room temperature.

EXAMPLE 6
Preparation of a Carbon Supported Catalyst of Metal Composition PtRu The binuclear non-cluster precursor, Pt(triphenylphosphine)(Cl)($\mu$-Cl$_2$)Ru(Cl)(trihapto:trihapto-2,7-dimethyloctadienediyl), in an amount of 0.12 g, was dissolved in 15 ml of acetone. The resulting solution was stirred with 0.16 g of carbon support. Deposition of the precursor onto the carbon support was achieved by removal of the liquid phase by evaporation. The resulting precursor/carbon composite was placed into a tube furnace and treated thermally under the following conditions: 25 to 280° C. under air; 280 to 650° C. under getter gas; anneal under N$_2$ gas at 650° C. for 10 minutes, after which time the sample was cooled to room temperature. A second deposition of 0.12 g of precursor was performed on this carbon nanocomposite, followed by repeating the thermal treatment described in this Example, with the exception that the final annealing step was held for 2.5 hours.

EXAMPLE 7
Preparation of a Carbon Supported Catalyst of Metal Composition PtRu The binuclear non-cluster precursor, Pt(triphenylphosphine)(Cl)($\mu$-Cl$_2$)Ru(Cl)(trihapto:trihapto-2,7-dimethyloctadienediyl), in an amount of 0.31 g was dissolved in 40 ml of acetone. The resulting solution was stirred with 0.27 g of carbon support. Deposition of the precursor onto the carbon support was achieved by removal of the liquid phase by evaporation. The resulting precursor/carbon composite was placed into a tube furnace and treated thermally under the following conditions: 25 to 350° C. under air; 350 to 650° C. under getter gas; anneal under N$_2$ gas at 650° C. for 5 minutes, after which time the sample was cooled to room temperature. A second deposition cycle was performed using 0.31 g of the precursor complex and the same thermal treatments described in this Example for the first cycle. A third deposition cycle was performed using 0.32 g of the precursor complex followed by the same thermal treatment, except that the final annealing step was performed for 50 minutes.

EXAMPLE 8
Preparation of a Carbon Supported Catalyst of Metal Composition PtRu A binuclear non-cluster precursor, {Ru(2,2'-bipyridine)$_2$($\mu$-bipyrimidine)PtCl$_2$}[hexafluorophosphate]$_2$, in the amount of 0.69 g was dissolved in 50 ml of acetonitrile. The resulting solution was stirred with 0.42 g of carbon support. Deposition of the precursor onto the carbon support was achieved by removal of the liquid phase by evaporation. The resulting precursor/carbon composite was placed into a tube furnace and treated thermally under the following conditions: 25 to 450° C. under air; 450 to 650° C. under getter gas; anneal under N$_2$ gas at 650° C. for 60 minutes, after which time the sample was cooled to room temperature.

EXAMPLE 9
Preparation of a Carbon Supported Catalyst of Metal Composition Pt$_3$Ru A tetranuclear cluster precursor having the presumed composition, {Pt$_3$[$\mu$-bis(diphenylphosphino)methane]$_3$(Ru)(pentahapto-cyclopentadienyl)}[hexafluorophosphate], in the amount of 0.50 g was dissolved in 10 ml of acetone. The resulting solution was stirred with 0.59 g of carbon support. Deposition of the precursor onto the carbon support was achieved by removal of the liquid phase by evaporation. The resulting precursor/carbon composite was placed into a tube furnace and treated thermally under the following conditions: 25 to 280° C. under air; 280 to 650° C. under getter gas; anneal under N$_2$ gas at 650° C. for 60 minutes, after which time the sample was cooled to room temperature.

EXAMPLE 10
Preparation of a Carbon Supported Catalyst of Metal Composition Pt$_3$Ru The tetranuclear non-cluster precursor, Ru($\mu$-2,3-bis(2-pyridyl)quinoxaline)PtCl$_2$)$_3$][tetrafluoroborate]$_2$, in the amount of 0.17 g was dissolved in 100 ml of acetonitrile. The resulting solution was stirred with 0.15 g of carbon support. Deposition of the precursor onto the carbon support was achieved by removal of the liquid phase by evaporation. The resulting precursor/carbon composite was placed into a tube furnace and treated thermally under the following conditions: 25 to 450° C. under air; 450 to 650° C. under getter gas; anneal under $N_2$ gas at 650° C. for 30 minutes, after which time the sample was cooled to room temperature.

EXAMPLE 11
Preparation of a Carbon Supported Catalyst of Metal Composition PtSn The binuclear cluster precursor, Pt(triphenylphosphine)$_2$(phenyl)-Sn(phenyl)$_2$Cl, in an amount of 0.29 g was dissolved in 60 ml of heptane. The resulting solution was stirred with 0.31 g of carbon support. Deposition of the precursor onto the carbon support was achieved by absorption of the precursor. The resulting precursor/carbon composite was isolated by centrifugation, placed into a tube furnace and treated thermally under the following conditions: 25 to 700° C. under hydrogen gas, and maintaining the temperature at 700° C. for two hours, after which time the sample was cooled to room temperature.

EXAMPLE 12
Preparation of a Carbon Supported Catalyst of Metal Composition PtSn The binuclear cluster precursor, Pt(triethylphosphine)$_2$(Cl)Sn(Cl$_3$), in an amount of 0.51 g was dissolved in 50 ml of methylene chloride. The resulting solution was stirred with 0.44 g of carbon support. Deposition of the precursor onto the carbon support was achieved by evaporation of the solvent. The treated carbon support was permitted to dry at room temperature. The resulting precursor/carbon composite was placed into a tube furnace and treated thermally under the following conditions: 25 to 250° C. under air; 250 to 650° C. under getter gas; anneal under $N_2$ gas at 650° C. for one hour, after which time the sample was cooled to room temperature.

EXAMPLE 13
Preparation of a Carbon Supported Catalyst of Metal Composition Pt$_3$Sn The tetranuclear cluster precursor, {Pt$_3$[$\mu$-(bis(diphenylphoshine)methane)]$_3$($\mu$-SnF$_3$)($\mu_3$-CO)}[hexafluorophosphate], in an amount of 0.11 g was dissolved in 50 ml of acetone. The resulting solution was stirred with 0.16 g of carbon support. Deposition of the precursor onto the carbon support was achieved by direct absorption of the precursor. The resulting precursor/carbon composite was isolated by centrifugation, placed into a tube furnace, and treated thermally under the following conditions: 25 to 280° C. under air; 280 to 650° C. under getter gas; anneal under $N_2$ gas at 650° C. for two hours, after which time the sample was cooled to room temperature.

EXAMPLE 14
Preparation of a Carbon Supported Catalyst of Metal Composition Pt$_3$Mo The tetranuclear cluster precursor, {Pt$_3$[$\mu$-(bis(diphenylphosphine)methane)]$_3$[1$_3$-Mo](pentahapto-cyclopentadienyl)(CO)}[hexafluorophosphate], in an amount of 0.20 g was dissolved in 5 ml of acetone. The resulting solution was stirred with 0.23 g of carbon support. Deposition of the precursor onto the carbon support was achieved by removal of the liquid phase by evaporation. The resulting precursor/carbon composite was placed into a tube furnace and treated thermally under the following conditions: 25 to 280° C. under air; 280 to 650° C. under getter gas; anneal under $N_2$ gas at 650° C. for one hour, after which time the sample was cooled to room temperature.

EXAMPLE 15
Preparation of a Carbon Supported Catalyst of Metal Composition Pt$_3$Mo A tetranuclear cluster precursor having the presumed composition, {Pt$_3$[$\mu$-(bis(diphenylphosphine)methane)]$_3$[$\mu_3$-Mo](pentahapto-cyclopentadienyl)(CO)}[tetraphenylborate], in the amount of 0.39 g was dissolved in 35 ml of methylene chloride. The resulting solution was stirred for 18 hours with 0.25 g of carbon support. Deposition of the precursor onto the carbon support was achieved by removal of the liquid phase by evaporation. The resulting precursor/carbon composite was placed into a tube furnace and heated to 350° C. under air, and then cooled to room temperature. This treated carbon composite was stirred for 18 hours with a solution containing 0.47 g of the precursor dissolved in 35 ml of methylene chloride. After removal of the liquid phase by evaporation, the resulting composite was placed into a tube furnace and treated thermally under the following conditions: 25 to 350° C. under air; 350 to 650° C. under getter gas; anneal under nitrogen gas at 650° C. for one hour, followed by cooling to room temperature; 25–350° C. over 10 minutes under air, followed by cooling to room temperature.

EXAMPLE 16
Preparation of a Carbon Supported Catalyst of Metal Composition RuMo The binuclear cluster precursor, Mo(heptahapto-cycloheptatrienyl)(CO)$_3$Ru(pentahapto-cyclopentadienyl)(CO)$_2$, in an amount of 0.71 g was dissolved in 35 ml of acetone. The resulting solution was stirred with 0.30 g of carbon support. Deposition of the precursor onto the carbon support was achieved by removal of the liquid phase by evaporation. The resulting precursor/carbon composite was placed into a tube furnace and treated thermally under the following conditions: 25 to 280° C. under air; 280 to 700° C. under getter gas, maintaining the temperature at 700° C. for 30 minutes; anneal under $N_2$ gas at 700° C. for 60 minutes, after which time the sample was cooled to room temperature.

EXAMPLE 17
Characterization of the Nanocomposites Prepared in Examples 4–16

The catalysts prepared as Examples 4–16 were characterized by transmission electron microscopy (TEM), energy dispersive spectroscopy (EDS), x-ray diffraction (XRD), and by chemical elemental analysis. Average catalyst nanoparticle sizes were estimated by measuring particle diameters from at least one TEM image of each sample. Results of these analyses are listed in Table 13 which shows the estimated average diameter of the alloy nanoparticles measured in nanometers, the metal chemical compositions, measured in weight percent, and the Pt/M' [or Ru/Mo(*)] atomic ratios as determined by chemical elemental analysis or from EDS. The precursor core Pt/M' or Ru/Mo(*) atomic ratios are also shown.

Experience reveals significant error in chemical elemental analyses for metal content in such carbon nanocomposites, particularly when small (i.e. less than 20 mg) sample sizes are used for the analyses. Atomic ratios determined by EDS were obtained directly from application of commercial software without using calibrated internal standard procedures.

Synthetic control of nanocluster elemental composition through the choice of a single-source molecular precursor was evident from the characterization of these carbon nanocomposites. The atomic ratio of metals in the catalyst composites, as determined by either bulk chemical elemental analysis or by EDS, were consistent with that metal stoichiometry present in the precursor molecule.

Figure 15A:
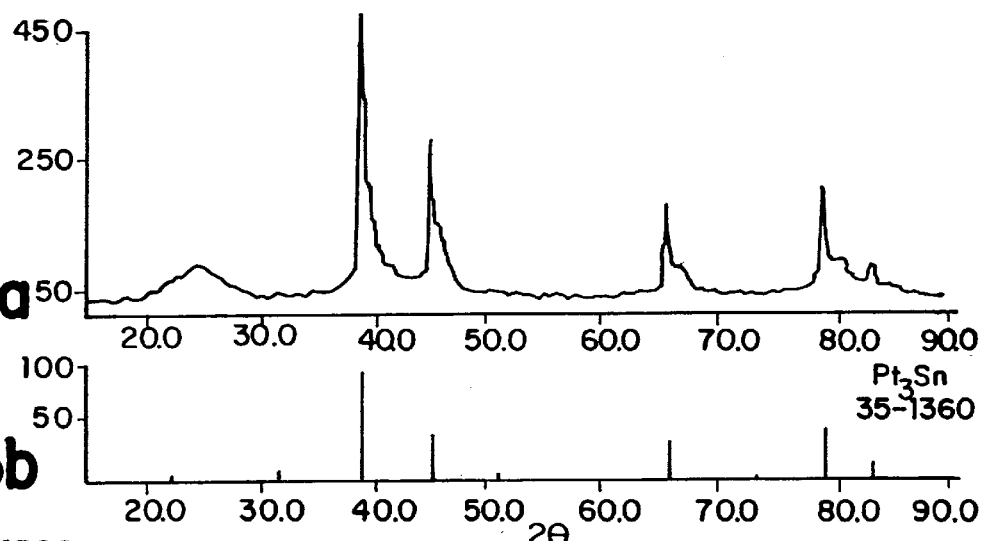
Figure 16A:
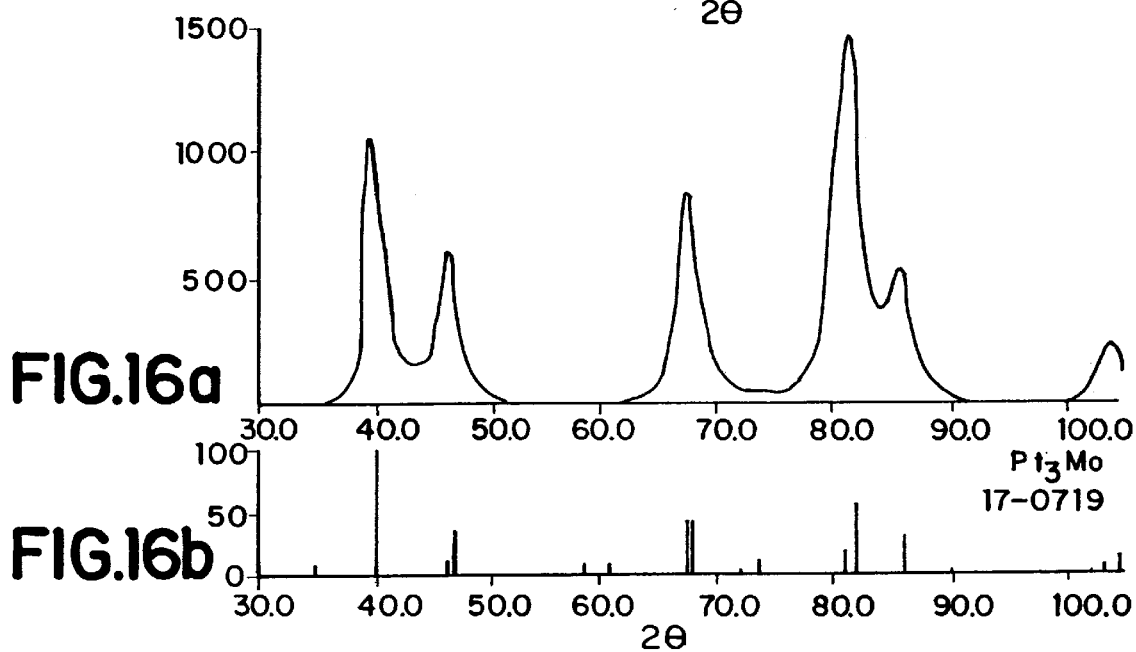

Stronger evidence for the control of nanocluster metal stoichiometry was obtained using XRD data. Crystalline intermetallic substances, such as PtSn, Pt$_3$Sn, and Pt$_3$Mo, have unique XRD patterns. FIGS. 14, 15 and 16 show the powder XRD patterns of the PtSn/C, Pt$_3$Sn/C, or Pt$_3$Mo/C catalysts, respectively, typifying XRD patterns for catalysts prepared as in Examples 12, 13, or 15, respectively. In each of these Figures, the XRD pattern of the corresponding pure substance is shown below the experimental result as a line pattern obtained from the standard Powder Diffraction Files. Broad peaks near 25° 2θ are formed from amorphous scattering from the carbon substrate. Diffraction peaks of the metal nanoclusters broaden as the volume weighted average particle size of the catalyst particles becomes smaller.

TABLE 13

| Catalyst | Ave. Dia. (nm) | Metal Chemical Composition (wt %) | | | | Pt/M' At. Ratio | EDS Pt/M' At. Ratio | Precursor Pt/M' At. Ratio |
| --- | --- | --- | --- | --- | --- | --- | --- | --- |
| | | Pt | Ru | Sn | Mo | | | |
| Example 4 | 3.6 | 4.43 | 2.70 | | | 0.9 | 0.9 | 1.0 |
| Example 5 | 3.9 | 15.9 | 9.84 | | | 0.8 | 1.0 | 1.0 |
| Example 6 | 2.8 | 17.8 | 8.99 | | | 1.0 | 1.2 | 1.0 |
| Example 7 | 3.7 | 24.53 | 12.77 | 1.0* | | 1.0 | 1.2 | 1.0 |
| Example 8 | 3.8 | 13.80 | 7.29 | | | 1.0 | 1.2 | 1.0 |
| Example 9 | 6.0 | | | | | | 2.5 | 3.0 |
| Example 10 | 3.8 | | | | | | 3.3 | 3.0 |
| Example 11 | 5.0 | 8.19 | | 6.18 | | 0.8 | 1.0 | 1.0 |
| Example 12 | 17.7 | 19.98 | | 6.79 | | 1.8 | 1.1 | 1.0 |
| Example 13 | 8.1 | | | | | | 3.3 | 3.0 |
| Example 14 | 3.5 | | | | | | — | 3.0 |
| Example 15 | 3.4 | 25.08 | | | 4.23 | 2.9 | 3.0 | 3.0 |
| Example 16 | 2.5 | | 17.90 | | 25.05 | 0.7* | 0.9* | 1.0* |

Comparison of the observed XRD pattern of each nanocomposite with that of the pure intermetallic substance reveals close agreement in both the 2θ values of peak positions and relative peak intensities, thereby confirming that crystalline intermetallic nanoclusters having metal compositions identical to those of the molecular precursors were formed.

Figure 17:
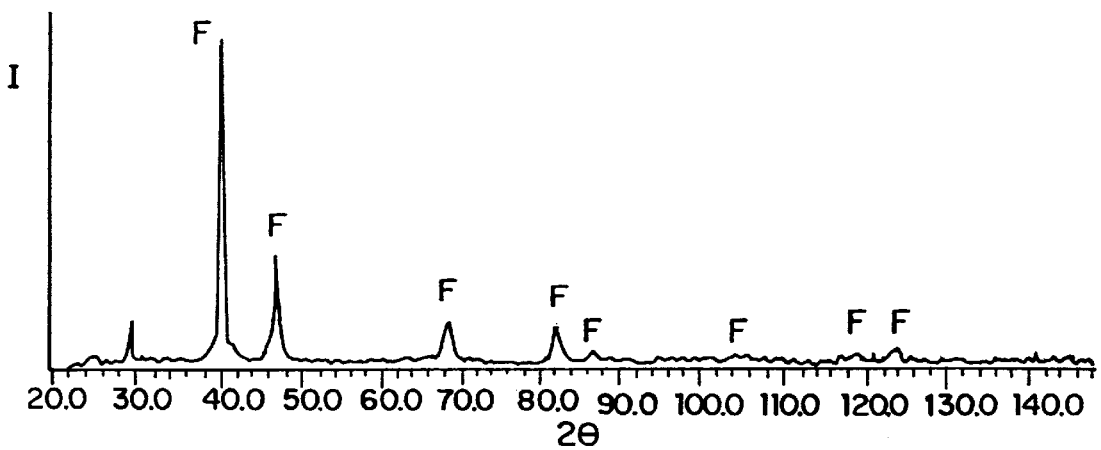
FIG. 17 is an XRD diffraction pattern of the platinum-ruthenium ($Pt_3Ru$) nanocomposite formed in accordance with Example 10.

XRD pat terns obtained from metal alloy nanoparticles are less unique. Usually, these catalyst composites yielded a pattern consistent with the high symmetry unit cell of one of the constituent metals. The unit cell parameter obtained from these alloy XRD patterns differed slightly from the unit cell parameters known for the pure metal constituents, because atoms of different elements have different atomic radii. For example, XRD patterns of the PtRu/C composites, such as those prepared as Examples 4–8, revealed a set of peaks that could be indexed using a face-centered-cubic (fcc) unit cell having a lattice constant, ao, of 3.87 Å. This value is consistent with the value predicted for a 1:1 alloy of Pt and Ru. The fcc unit cell parameter of pure platinum is 3.92 Å. Likewise, the Pt$_3$Ru/C composite prepared in Example 10 yielded a powder XRD pattern shown in FIG. 17. This pattern is consistent with a face-centered-cubic crystalline structure having a unit cell parameter of 3.91 Å. A slightly larger cell parameter is expected for nanocrystals of composition Pt$_3$Ru, relative to those having a PtRu composition because Pt atoms are slightly larger than Ru atoms.

EXAMPLE 18
Performance of the Nanocomposites Prepared in Examples 4–16 as Fuel Cell Catalysts Several of the crystalline nanocomposites prepared as Examples 4–16 were tested as either anode or cathode catalysts in DMFCs or by electrochemical means. The results summarized below represent non-optimized performance levels obtained usually from a single testing laboratory.

Electrochemical testing of the Pt$_3$Mo/C catalyst prepared in Example 14 revealed catalytic activity for oxygen reduction and methanol tolerance. Testing this catalyst in a DMFC confirmed slight methanol tolerance when this catalyst was used as a cathode catalyst.

Other metal alloy composites described herein have been tested as DMFC anode catalysts. DMFC tests were performed by standard methods as described above with estimated catalyst loadings at the anode as indicated in Table 14. The test fixture was fabricated with a membrane comprising the polymetallic material designated Nafion® 117, and test conditions included an oxygen flow rate of 400 ml/min and a back pressure of 10 psig, a methanol concentration of 0.5 M, a methanol flow rate of 25 ml/min, and a methanol back pressure of zero psig. The temperature of the test fixture was 90° C. Performance results are presented as current density (mA/cm$^2$) measured at about 0.4V are shown in Table 14. Current densities were extracted from the corresponding experimentally recorded I-V curves for each test sample. Catalyst performance values reported in Table 14 are not optimized. Of particular note, the Pt$_3$Ru/C catalyst, Example 9, has a higher open-circuit potential 15 than does a commercial PtRu/C catalyst, indicating that this catalyst has an intrinsic catalytic activity superior to that of commercially available DMFC catalysts.

TABLE 14

| Catalyst | Composition | Current Density (mA/cm$^2$) | Total Metal Loading (mg/cm$^2$) | Platinum Loading (mg/cm$^2$) |
| --- | --- | --- | --- | --- |
| Example 4 | PtRu | 63 | 0.30 | 0.20 |
| Example 6 | PtRu | 100 | 0.26 | 0.17 |
| Example 9 | Pt$_3$Ru | 83 | 0.33 | 0.28 |
| Example 11 | PtSn | 47 | 0.30 | 0.19 |
| Example 13 | Pt$_3$Sn | 40 | 0.36 | 0.30 |

Figure 18:
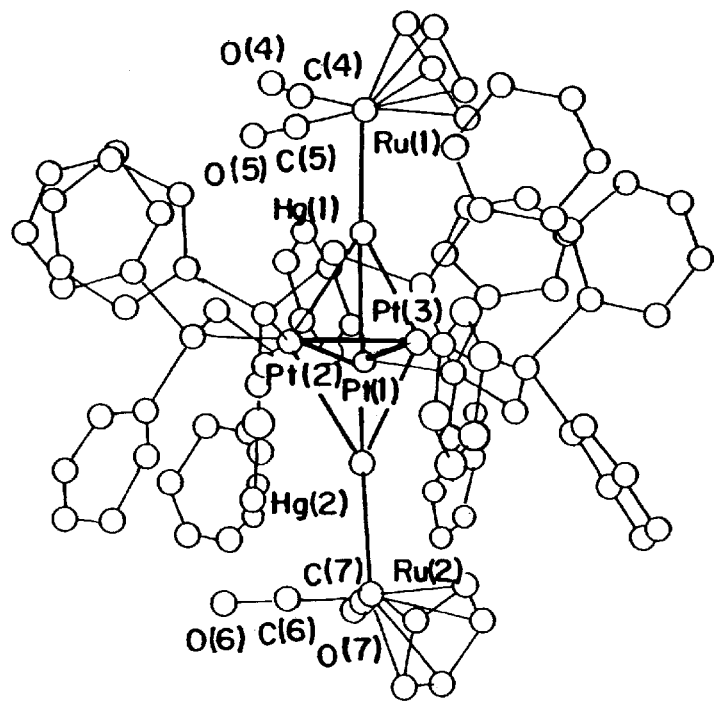
FIG. 18 is a schematic representation of the molecular structure of the tetrametallic precursor, $\{Pt_3[\mu$-bis(diphenylphosphino)methane$]_3[\mu_4$-Hg—Ru(pentahapto-cyclopentadienyl)(CO)$_2]_2\}[PF_6]_2$, showing the metal, phosphorus, oxygen, and carbon atoms of the compound.
Figure 19:
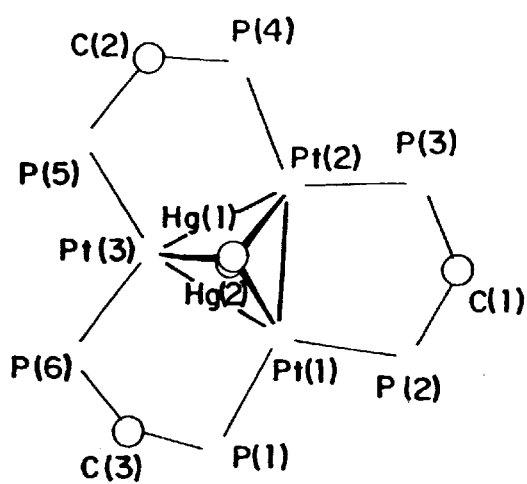
FIG. 19 is a schematic representation of the structure of the molecular core of the precursor of FIG. 18.

EXAMPLE 19
Synthesis of a Polymetallic Precursor Comprising Pt, Ru, and Hg, and the Preparation of Carbon-Supported Metal Nanoparticles Using this Precursor Several transition metal complexes comprising mercury are known, including complexes comprising a Hg—Pt or Hg—Ru bond. In this Example, synthesis, characterization and use of a novel complex as a polymetallic precursor to form a supported nanocomposite comprising polymetallic nanoparticles are described. The novel polymetallic precursor has the formula {Pt$_3$[,$\mu$-bis(diphenylphosphine) methane]$_3${$\mu_4$-Hg—Ru(pentahapto-cyclopentadienyl)(CO)$_2$]$_2$}[hexafluorophosphate]$_2$ and is depicted in FIG. 18. FIG. 19 shows the trigonal-bypyramidal core of the precursor of FIG. 18.

{Pt$_3$[$\mu$-bis(diphenylphosphine)methane]$_3${$\mu_4$-Hg—Ru(pentahapto-cyclopentadienyl)(CO)$_2$]$_2$}[hexafluorophosphate]$_2$ was prepared as follows. A reactant solution was made by stirring a solution comprising the dimer, [cyclopentadienylRu(CO)$_2$]$_2$, in THF in the presence of a Na/Hg amalgam for 3.5 hours. The reactant solution was filtered through glass wool into a solution comprising the triplatinum cluster, [Pt$_3$(dppm)$_3$(CO)][PF$_6$]$_2$ in THF, thereby forming the heteronuclear precursor, {Pt$_3$[$\mu$-bis(diphenylphosphine)methane]$_3${$\mu_4$-Hg—Ru(pentahapto-cyclopentadienyl)(CO)$_2$]$_2$}[hexafluorophosphate]$_2$. This compound was recovered in 40% overall yield following chromatographic purification.

Figure 20:
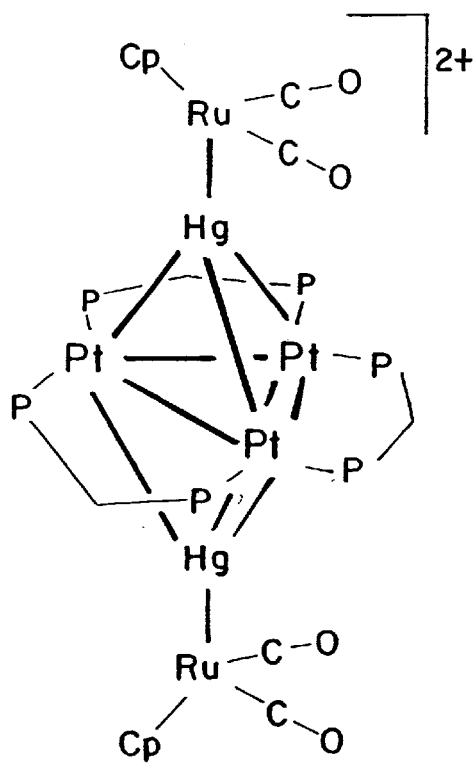
FIG. 20 is a schematic representation of general structure of the molecular structure of tetrametallic precursor, $\{Pt_3[\mu$-bis(diphenylphosphino)methane$]_3[\mu_4$-Hg—Ru(pentahapto-cyclopentadienyl)(CO)$_2]_2\}[PF_6]_2$.

The {Pt$_3$[$\mu$-bis(diphenylphosphine)methane]$_3${$\mu_4$-Hg—Ru(pentahapto-cyclopentadienyl)(CO)$_2$]$_2$}[hexafluorophosphate]$_2$ prepared as described in this Example, had the following properties: $^1$H NMR: 5.15 (s, 10H, Cp), 5.58 (tr, br, 6H CH$_2$), 6.9–7.3 (m, 60H, Phenyl); $^{13}$C{$^1$H} NMR: 84.8 (Cp), 128.8, 131.2, 132.1 (Phenyl); $^{13}$PP{$^1$H} NMR: −5.3 [dppm, $^1$J(PtP)=2927 Hz, $^2$J(PtP)= 184 Hz, $^2$J(HgP)=127 Hz, $^3$J(PP)=212 Hz], −143.3 [hp, PF$_6$, $^1$J(PF)=667 Hz]; IR 1972 and 2007 cm$^{-1}$ (CO); Elemental Analysis, Calc. for Pt$_3$Hg$_2$Ru$_2$C$_{89}$H$_{76}$P$_8$O$_4$Fl$_2$: C, 37.20; H, 2.67; P, 8.62; Found: C, 37.20; H, 2.82; P, 8.17. The prepared precursor had a trigonalbipyramidal Pt$_3$Hg$_2$ structural moiety, as depicted in FIG. 20.

Figure 21:
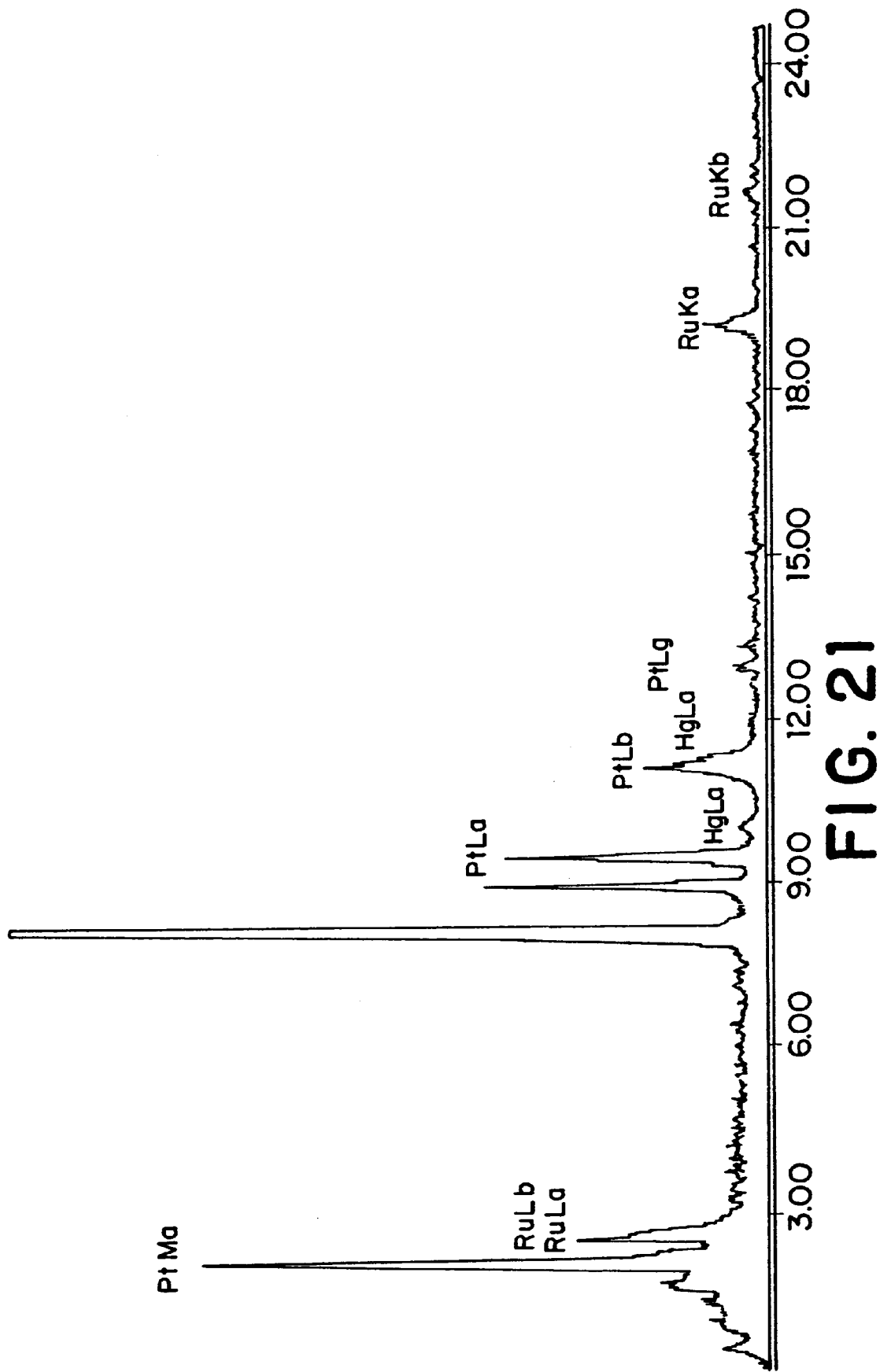
FIG. 21 is an EDS spectrum of the platinum-ruthenium ($Pt_3Ru_2$) nanocomposite formed in accordance with Example 19.
Figure 22:
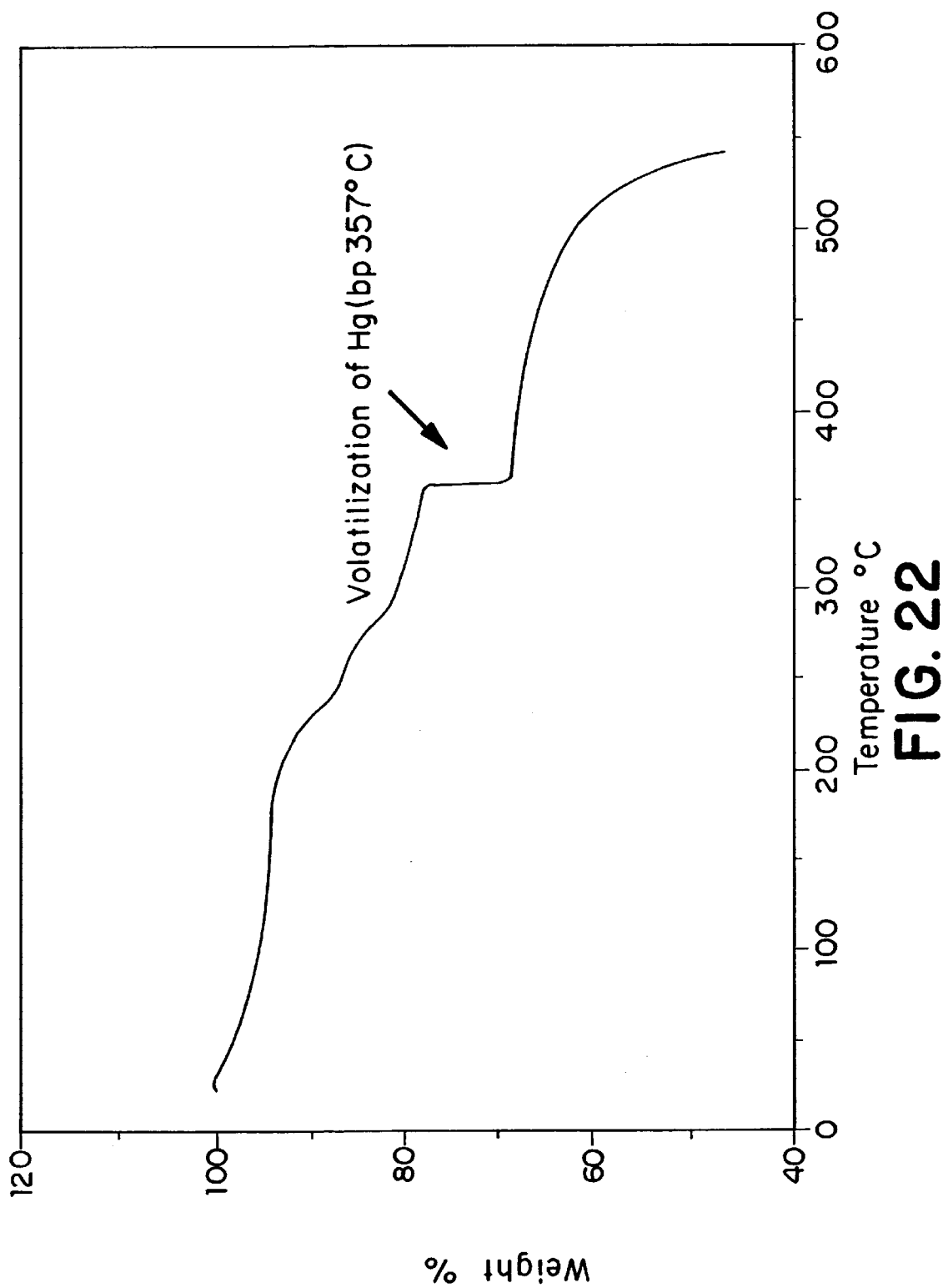
FIG. 22 is a graphic representation of the thermal gravimetric analysis of the platinum-ruthenium ($Pt_3Ru_2$) nanocomposite formed in accordance with Example 19.
Figure 23:
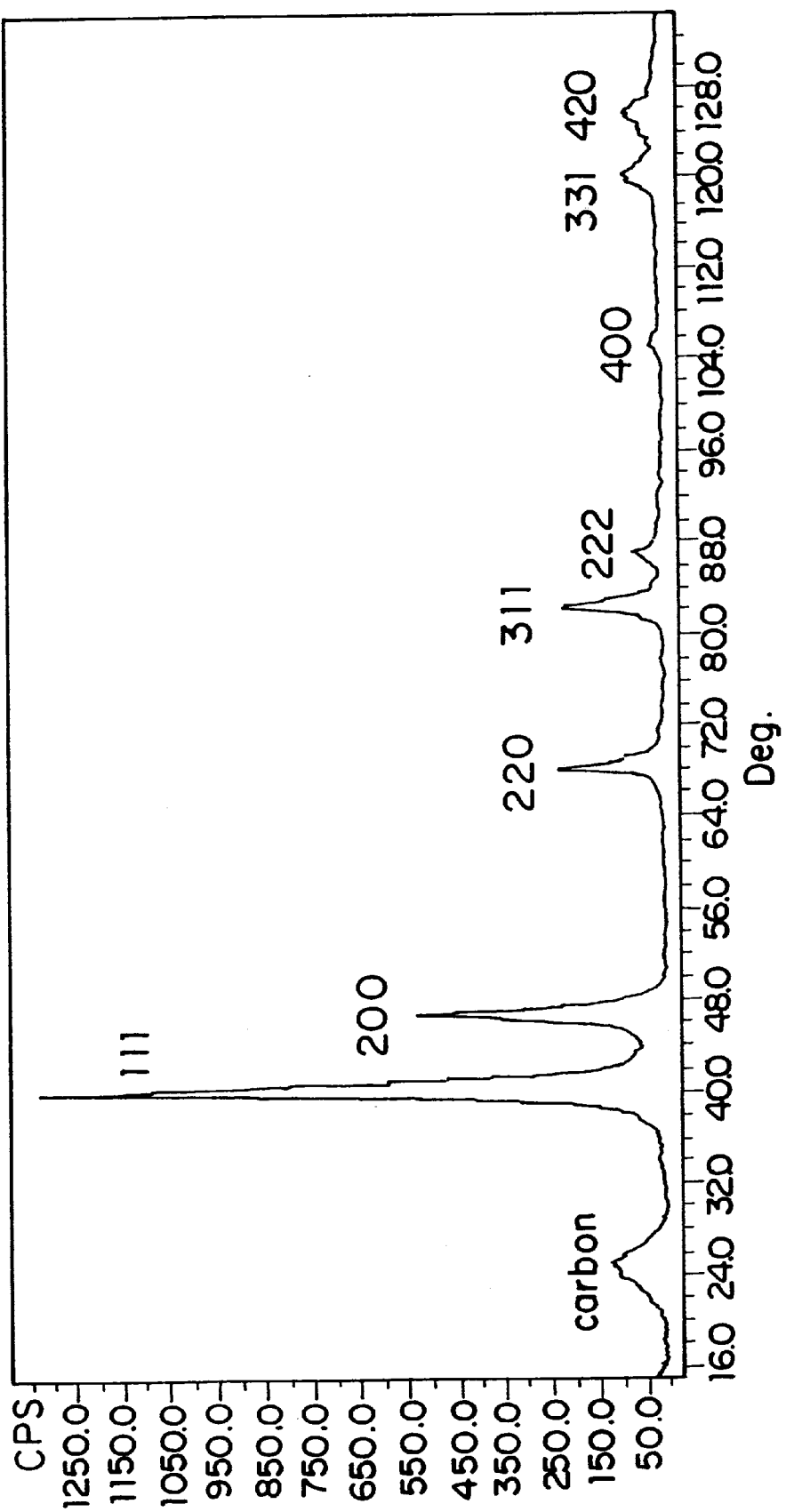
FIG. 23 is the XRD diffraction pattern of the platinum-ruthenium ($Pt_3Ru_2$) nanocomposite formed in accordance with Example 19.

{Pt$_3$[$\mu$-bis(diphenylphosphine)methane]$_3${$\mu_4$-Hg—Ru(pentahapto-cyclopentadienyl)(CO)$_2$]$_2$}[hexafluorophosphate]$_2$ was adsorbed onto Vulcant® particulate carbon by an incipient wetness technique. The doped particulate carbon was heated from 25 to 380° C. in the presence of air and from 380 to 650° C. in the presence of nitrogen and held at 650° C. in getter gas. The treatment was then repeated but initially heated from 25 to 400° C. in air, then heated from 400 to 650° C. in nitrogen and held at 650° C. in getter gas a sufficient time to form a nanocomposite comprising nanoparticles having a composition in which the atomic ratio of Pt to Ru was approximately 3:2 and in which the proportion of metal atoms which were Hg was less than 3%, as indicated by the EDS spectrum shown in FIG. 21. A thermal gravimetric analysis of the nanocomposite is shown in FIG. 22, and an XRD scan of the nanocomposite is shown in FIG. 23. XRD analysis indicated that the nanoparticles had an average diameter of 7.5 nm, with a standard deviation of 0.4 nm, and revealed a set of peaks that could be indexed using a face-centered-cubic (fcc) unit cell having a lattice constant, a, of 3.875 Å (standard deviation 0.002). This value is consistent with the value (3.876) predicted for a 3:2 alloy of Pt and Ru. TEM analysis indicated that the nanoparticles exhibited a monomodal diameter distribution, the average nanoparticle diameter being 3.87 nm, the standard deviation being 2.0 nm, and the median diameter being 3.38 nm.

EXAMPLE 20

The binuclear non-cluster precursor complex, [Ru(2,2'-bipyridine)$_2$($\mu$-bipyrimidine)PtCl$_2$[tetrafluoroborate]$_2$, in an amount of 0.53 g was dissolved in 50 ml acetonitrile. The resulting solution was stirred with 0.16 g of carbon support. Deposition of the precursor onto the carbon support was achieved by removal of the liquid phase by evaporation. The resulting precursor/carbon composite was placed into a tube furnace as described above and was treated thermally under the following conditions: 25 to 650° C. under nitrogen at 30° C. per minute; held at 650° C. under getter gas (90/10 nitrogen/hydrogen mixture) for 20 minutes; switching to nitrogen gas with cooling to room temperature at a rate of 2.5° C./min. From preliminary testing, the nanocomposite shows a high degree of purity and with negligible phosphorus.

EXAMPLE 21

The tetranuclear non-cluster precursor complex [Ru($\mu$-2,3-bis($\mu$-pyridyl)quinoxaline)PtCl$_2$)$_3$][tetrafluoroborate]$_2$, in an amount of 1.10 g was dissolved in 50 ml of acetonitrile. The resulting solution was deposited onto 0.39 g of carbon support in three deposition/heat treatment cycles using nearly equal amounts of precursor solution. Each deposition of the precursor onto the carbon support is achieved by removal of the liquid phase by evaporation followed by heating the sample in a tube furnace from 25 to 350° C. under getter gas at a heating rate of 15° C./min and then cooling to room temperature under a nitrogen purge. The final heat treatment included an annealing of the sample at 350° C. under nitrogen for 30 minutes followed by cooling to room temperature.

EXAMPLE 22

The Pt$_3$Ru/Vulcan carbon nanocomposite prepared in accordance with Example 21 was subjected to a subsequent oxidative thermal treatment including heating the nanocomposite from 25° C. to 350° C. in air at a rate of 15° C./min followed by a 10 minute purge with nitrogen and a subsequent heating of the sample from 350° C. to 650° C. in getter gas at a rate of 15° C./min. The sample was then annealed at 650° C. under nitrogen and was then permitted to cool to room temperature under nitrogen.

EXAMPLE 23

The binuclear non-cluster precursor complex [Ru($\mu$-bipyrimidine)(2,2'-bipyridine)$_2$PtCl$_2$][hexafluorophosphate]$_2$ in an amount of 0.29 g was dissolved in 50 ml of acetonitrile. The resulting solution was stirred with 0.31 g of carbon support. Deposition of the precursor onto the carbon support was achieved by removal of the liquid phase by evaporation. The resulting precursor/carbon composite was placed into a tube furnace as described above and was treated thermally under the following conditions: 25 to 280° C. under air; 280 to 650° C. under getter gas, after which time the sample was cooled to room temperature. A second deposition of 0.27 g of the precursor complex noted above in this Example was performed likewise using a solution in acetonitrile and solvent evaporation. The resulting precursor/carbon composite was placed into a tube furnace as described above and was treated thermally under the following conditions: 25 to 280° C. under air; 280 to 650° C. under getter gas followed by thermal annealing at 650° C. under nitrogen for 60 minutes after which time the sample was cooled to room temperature. This sample demonstrated good fuel cell properties in a DMFC test cell.

EXAMPLE 24

The dinuclear non-cluster precursor complex Pt(dihapto-ethylene)(Cl)($\mu$-Cl)$_2$Ru(Cl)(trihapto:trihapto-2,7- dimethyloctadienediyl), in an amount of 0.11 g was dissolved in 15 ml of acetone and was added to a flask containing 0.16 g of Vulcan carbon having the specified criteria noted above in previous examples. Deposition of the precursor onto the carbon support was achieved by removal of the liquid phase by evaporation. The above deposition and heat treatment steps in Example 23 were repeated twice. The final heat treatment included an annealing at 350° C. under nitrogen for 15–20 minutes followed by cooling to room temperature. The nanocomposite included very pure PtRu alloy nanocrystals.

EXAMPLE 25

The PtRu/Vulcan carbon nanocomposite prepared in Example 24 was subjected to a subsequent oxidative thermal treatment including heating the nanocomposite from 25° C. to 350° C. in air at a rate of 15° C./min followed by a 10 minute purge with nitrogen followed by heating the sample from 350 to 650° C. in getter gas at a rate of 15° C./min. The sample was then annealed at 650° C. under nitrogen and was permitted to cool to room temperature under nitrogen. The air treatment helps ensure that crystal surfaces are free of organic residue for use in DMFC catalysis.

EXAMPLE 26

The trinuclear cluster precursor complex, {Pt[bis-(pentahapto-cyclopentadienylmolybdenumtricarbonyl)](bispyridine)} in an amount of 0.44 g was dissolved in 80 ml of dimethylsulfoxide under a nitrogen atmosphere. The resulting solution was stirred with 0.13 g of carbon support. Deposition of the precursor onto the carbon support was achieved by removal of the liquid phase by evaporation. The resulting precursor/carbon composite was dried at reduced pressure at 100° C. for four hours then placed into a tube furnace as described above. This sample was treated thermally under the following conditions: 25 to 280° C. under air; 280 to 650° C. under getter gas; anneal at 650° C. under nitrogen for 50 minutes after which time the sample was cooled to room temperature. The resulting nanocomposite having a $PtMo_2$ stoichiometry exhibited properties useful as a cathode catalyst.

EXAMPLE 27

The di-nuclear non-cluster precursor complex Pt(triphenylphosphine)(Cl)($\mu$-Cl)$_2$Ru(Cl)(trihapto:trihapto-2,7-dimethyloctadienediyl), in the amount of 0.31 g was dissolved in 10 ml of acetone and was added to a flask containing 0.34 g of Vulcan carbon. Deposition of the precursor onto the carbon support was achieved by removal of he liquid phase by evaporation. This sample was placed into a tube furnace and was heated from 25 to 350° C. under getter gas and was cooled to room temperature under nitrogen. A second deposition and heat treatment was performed following the above procedure using 0.31 g of molecular precursor and 15 ml of acetone. A third deposition and heat treatment was performed following the above procedure using 0.33 g of molecular precursor and 15 ml of acetone. The obtained sample was then treated with 0.15 g of triphenylphosphine dissolved in 20 ml of acetone followed by evaporation of solvent. This final sample was heated from 25 to 420° C. in getter gas followed by heating at 420° C. under nitrogen for 10 minutes and was then cooled to room temperature. The resulting composite had a ternary $PtRuP_2$ alloy in which phosphorus was intentionally retained by not using air treatment.

Available testing results from Examples 20–27 are included below in Table 15 below.

EXAMPLE 28

The precursor of Example 24 was prepared following procedures reported for the synthesis of analogous complexes as set forth in Severin et al., *Inorg Chim. Acta*, 240, 339 (1995). 0.640 g (1.06 mmol) of $Pt_2Cl_2(\mu_2\text{-Cl})_2(C_2H_4)_2$ and 0.637 g (1.03 mmol) of $Ru_2Cl_2(\mu_2\text{-Cl})_2$(trihapto:trihapto-2,7-dimethyloctadienediyl)$_2$ were placed in a round bottom flask and dissolved in approximately 75 ml of $CH_2Cl_2$. The solution was left stirring for several hours under a nitrogen atmosphere. The solvent was removed from the reddish brown solution to give a brown powder. Recrystallization from methylene chloride/hexane solution gave 1.187 g (1.97 mmol, 95% yield) of the precursor of Example 24 having a melting point of 140–146° C. Spectroscopic data indicated that small amounts of a second isomer were also present in the sample. The isomer in which the dihapto-ethylene and trihapto:trihapto-2,7-dimethyloctadienediyl ligands occupy mutually trans orientations is most often observed for cluster molecules having somewhat similar structures, but isomeric mixtures have been reported as well. Spectroscopic data was generated for the major isomer of the precursor under $^1$H NMR and $^{13}$C NMR.

Anal. Calc. for $C_{12}H_{20}Cl_4PtRu$: C, 23.93; H, 3.35. Found: C, 24.43; H 3.72.

EXAMPLE 29

The precursor of Example 27 was synthesized by the Severin procedure as noted in Example 28. 718 mg (0.680 mmol) of $Pt_2Cl_2(\mu\text{-Cl})_2$(triphenylphosphine)$_2$ and 417 mg (0.677) mmol of $Ru_2Cl_2(\mu\text{-Cl})_2$(trihapto:trihapto-2,7-dimethyloctadienediyl)$_2$ were placed in a round bottom flask and dissolved in approximately 100 ml of $CH_2Cl_2$. The solution was left stirring overnight under a nitrogen atmosphere. the solvent was removed from the reddish-brown solution to give a brown powder. Recrystallization from acetone/hexane solution gave 981 mg of the precursor of Example 27 (86% yield) with a melting point of 140–146° C. Spectroscopic data indicated that small amounts of a second isomer were also present in the sample. Spectroscopic data was generated for the major isomer of the precursor under $^1$H NMR, $^{13}$C NMR and $^{31}$P NMR.

Anal. Calc. for $C_{28}H_{31}Cl_4PPtRu$: C, 40.20; H, 3.74; P, 3.70; found: C, 39.75; H, 3.66; P, 3.81.

TABLE 15

| Catalyst | Ave. Dia. (nm) | Metal Chemical Composition (wt %) | | | | Pt/M' At. Ratio | EDS Pt/M' At. Ratio | Precursor Pt/M' At. Ratio |
|---|---|---|---|---|---|---|---|---|
| | | Pt | Ru | Sn | Mo | | | |
| Example 20 | 4.3 | 20.08 | 8.20 | | | 1.3 | 1.2 | 1.0 |
| Example 21 | 5.7 | 29.79 | 4.82 | | | 3.2 | 4.3 | 3.0 |

TABLE 15-continued

| Catalyst | Ave. Dia. (nm) | Metal Chemical Composition (wt %) | | | | Pt/M' At. Ratio | EDS Pt/M' At. Ratio | Precursor Pt/M' At. Ratio |
| --- | --- | --- | --- | --- | --- | --- | --- | --- |
| | | Pt | Ru | Sn | Mo | | | |
| Example 22 | | | | | | | | 3.0 |
| Example 23 | 44.0 | | | | | | | 1.0 |
| Example 24 | 2.6 | 22.28 | 12.88 | | | 0.90 | | 1.0 |
| Example 25 | | | | | | | | 1.0 |
| Example 26 | 3.5 | 29.32 | | | 28.90 | 0.52 | 0.50 | 0.50 |
| Example 27 | 3.6 | | | | | | | 1.0 |

EXAMPLE 30

The precursor of Example 20 was prepared in accordance with the following procedure. Initially, bis-(2,2'-bipyridine)-2,2'-bipyrimidineruthenium (II) tetrafluoroborate (referred to herein as "[Ru(bpy)$_2$(bpm)][BF$_4$]$_2$")was prepared by a modification of the method reported by Nallas et al., *Inorgan. Chem.* 35,6974 (1996) for synthesis of the PF$_6^-$ salt of this compound. 0.465 g (0.96 mmol) of Ru(2,2'-bipyridine)$_2$Cl$_2$ was dissolved in 50 mol of a 2:1 ethanol/water solution. To this solution was added 0.276 g (1.75 mmol) of 2,2'-bipyrimidine. The suspension was stirred and heated at reflux under nitrogen atmosphere for 2 hours. Upon cooling, the solution was added to 50 ml of an aqueous solution containing 1.0 g (9.1 mmol) of NABF$_4$. No precipitate was observed, so the solvent was removed with a rotary evaporator. The residue was then dissolved in a 3:2 toluene/acetonitrile solution, and developed on an adsorption alumina column using the toluene/acetonitrile solution as the eluent. A single orange band was collected and the solvent was removed by rotoevaporation. The product was then redissolved in a minimal amount of acetonitrile, flash precipitated with diethyl ether, and collected by vacuum filtration. The bright orange solid was washed with diethyl ether, and dried in vacuo at 80° C. to give 0.357 g (0.48 mmol) at a 50% yield of [Ru(bpy)$_2$(bpm)][BF$_4$]$_2$.

Anal. Calcd. for C$_{28}$H$_{22}$N$_8$B$_2$F$_8$Ru.3H$_2$O: C, 42.08; H, 3.56; N, 14.22. Found: C, 41.81; H, 3.41; N, 13.91.

The above synthesized [Ru(bpy)$_2$(bpm)][BF$_4$]$_2$ was then used to synthesize the precursor of Example 20. The synthesis of that precursor was undertaken using a modified method reported by Sahai et al., *Inorg. Chim. Act*, 118, L35 (1986) for the synthesis of ClO$_4$ salt of this compound. 0.200 g (0.474 mmol) of (DMSO)$_2$PtCl$_2$ and 0.353 g (0.474 mmol) of the [Ru(bpy)$_2$(bpm)][BF$_4$]$_2$ synthesized as above were dissolved in 50 ml of deoxygenated methanol. This solution was heated at reflux in the dark under a nitrogen atmosphere for approximately 12 hours. Upon cooling, a precipitate formed which was collected by vacuum filtration, washed with diethyl ether, and dried in vacuo for 4 hours to give 0.443 g of brick-red solid (0.42 mmol) at a 92.5% yield.

Anal. Calcd. for C$_{28}$H$_{22}$N$_8$B$_2$F$_8$RuPt: C, 33.26; H, 2.19; N, 11.08. Found: C, 33.28; H, 2.23; N, 11.16.

EXAMPLE 31

The precursor of Example 21 was prepared by first synthesizing tris-(2,3-bis(2-pyridyl)quinoxaline)ruthenium (II) tetrafluoroborate ("Ru(dpq)$_3$[BF$_4$]$_2$"). This compound was prepared using a modification of the procedure reported in Rillema et al., *Inorg. Chem.* 26, 578 (1987) for the synthesis of PF$_6$ salt of this compound. 0.306 g (1.48 mmol) of RuCl$_3$.nH$_2$O and 2.52 g (8.86 mmol) of 2,3-bis(2-pyridyl)quinoxaline were added to 50 ml of ethylene glycol. The mixture was stirred and heated at reflux under nitrogen atmosphere for about 2 hours. The solution was then allowed to cool to room temperature and filtered to remove any unreacted ligand. The value was doubled with water and the resulting solution was added to a saturated aqueous solution containing 1.0 g (9.1 mmol) of NaBF$_4$. A precipitate formed which was collected by vacuum filtration. The solid was then dissolved in a minimal amount of acetonitrile and developed on a neutral alumina column using acetonitrile as the eluent. The major red band was collected leaving a green band of unknown byproduct on the column. The solvent was then removed from the sample using a rotary evaporator. Finally, the product was redissolved in a minimal amount of acetonitrile, and precipitated with diethyl ether. The red powder was collected by vacuum filtration, washed with diethyl ether, and dried in vacuo at 80° C. for approximately 4 hours to give 1.02 g (0.86 mmol) at 65% yield.

Anal. Calcd. for C$_{54}$H$_{36}$N$_{12}$B$_2$F$_8$Ru.3H$_2$O: C, 54.89; H, 3.58; N, 14.22. Found: C, 54.68; H, 3.54; N, 14.33.

From the above synthesized Ru(dpq)$_3$[BF$_4$]$_2$, the precursor of Example 21 was prepared. The synthesis of the precursor was undertaken using a modification of the procedure reported in Rillema et al., *J. Chem. Commun*, 1133 (1986) for the preparation of the PF$_6$ salt of this compound. 0.301 g (0.267 mmol) of Ru(dpq)$_3$[BF$_4$]$_2$ and 0.470 g (1.11 mmol) of cis-(DMSO)$_2$PtCl$_2$ were dissolved in 100 ml of deoxygenated methanol. The solution was heated at reflux, under a nitrogen atmosphere in the dark for about 12 hours. The dark purple suspension was cooled to 30° C. for 6 hours and filtered. The resulting purple solid was washed with cold methanol and dried in vacuo at 80° C. for approximately 4 hours to give 0.370 g (0.187 mmol) at a 70% yield of the precursor of Example 21. Elemental analysis revealed that the sample was a trihydrate.

Anal. Calcd. for C$_{54}$H$_{36}$N$_{12}$B$_2$C$_{16}$F$_8$RuPt$_3$.3H$_2$O: C, 32.76; H, 2.14; N, 8.49. Found: C, 33.04; H, 2.45; N, 8.37.

EXAMPLE 32

The precursor of Example 14 was prepared using a procedure similar to that reported by Ferguson et al., *Organometallics*, 5, 344 (1986) by the reaction of {Pt$_3$($\mu_3$-CO)[$\mu$-bis(diphenylphosphino)methane]$_3$[PF$_6$]$_2$ and Na[(pentahapto-cyclopentadienyl)Mo(CO)$_3$]. An analog of the precursor of Example 14 including a tetraphenyl borate anion instead of a PF$_6$ anion was also synthesized.

Na[(pentahapto-cyclopentadienyl)Mo(CO)$_3$] in an amount of 0.2480 g (0.506 mmol) was added to Na/Hg (prepared by dissolving about 2 g Na in 7 ml of Hg) in 10 ml of THF in nitrogen flow. The reaction mixture was allowed to stir under nitrogen for 3 hours. Color changed from red to olive-green. The olive-colored solution was filtered through celite into another shlenk flask purged with nitrogen then {Pt₃(μ₃-CO)[μ-bis(diphenylphosphino)methane]₃}[PF₆]₂ as added in an amount of 0.2005 g (0.0975 mmol) and the color turned to blood-red. The reaction mixture was stirred for 24 hours, solvent was removed under vacuum, and the residue redissolved in about 3 ml of THF and purified on a silica column packed in methylene chloride. Product was eluted with methylene chloride (dark red band). The spectroscopic data generated for the precursor of Example 14 was as follows: $^1$H NMR $\delta^{CDCl_3}$ 7.5–6.9 (60H, m), 5.42 (5H, s); $^{31}$P-NMR $\delta^{CDCl_3}$ 51.4 (septet, $PF_6^-$, J=713 Hz),–8.2 (m, dppm, $J^1_{P-Pt}$=3872 Hz, $J^2_{P-Pt}$=392 Hz). Several attempts to obtain single crystals followed by the crystal structure have failed presumably due to loss of solvate from crystals.

The [tetraphenylborate]₂ analog of the Precursor of Example 14 in which [tetraphenylborate]₂ was used instead of the [PF₆] anion was prepared by the same procedure of Ferguson et al. referenced herein with a two-fold excess of Na[(pentahapto-cyclopentadienyl)Mo(CO)₃] instead of 10 as used above. Recrystallization was performed with methylene chloride/pentane. $^1$H-NMR $\delta^{CDCl_3}$ 7.5–7.3 (m, tetraphenylphosphine), 7.2–6.8 (60H, m, dppm's Ph), 4.79 (5H, s, pentahaptocyclopentadienyl).

Anal. Calcd. for $C_{105}H_{91}B_1O_1P_6Pt_3Mo_1$: C, 56.13; H, 4.08; P, 8.27. Found: C, 54.37; H, 4.16; P, 7.86.

The disclosures of each and every reference, publication or patent cited herein is hereby incorporated by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A polymetallic precursor having at least one first metal and at least one second metal and comprising at least one metal-ligand-metal group represented by the formula:

$$M_n\text{—}X\text{—}M'_p,$$

wherein M is an atom of the first metal; X is a thermally degradable ligand having a degradation temperature lower than degradation temperatures of M and M' and X is selected from the group consisting of a single atom, compound or moiety having an atom selected from the group consisting of a halogen, a mercury atom, a phosphorus atom, an atom from Groups 14–17 of the Periodic Table; organic ligands selected from the group consisting of alkyl, alkenyl, alkynyl, aryl, aralkyl, alkylphosphino, aryphosphino, alkylsulfide, arylsulfide, alkylselenide, arylselenide, arlkylmercuric, and arylmercuric; ammonia; amine; alkene; heteroatomic aromatic molecules; arsenes; and derivatives thereof; M' is an atom of the first metal or the second metal; and n and p are each at least one.

2. The polymetallic precursor according to claim 1, wherein the polymetallic precursor is a non-cluster polymetallic precursor.

3. The polymetallic precursor according to claim 1, wherein the at least one first metal is platinum and the stoichiometric ratio of the at least one first metal to the at least one second metal is greater than or equal to about 1.

4. The polymetallic precursor according to claim 1, wherein X is a bridging ligand.

5. The polymetallic precursor according to claim 1, wherein M is platinum, X is mercury and the precursor comprises a trigonal-bipyramidal Pt₃Hg₂ moiety.

6. A polymetallic precursor having at least one first metal and at least one second metal and comprising at least one metal-ligand-metal group represented by the formula:

$$M_n\text{—}X\text{—}M'_p,$$

wherein M is an atom of the first metal; X is a thermally degradable ligand having a degradation temperature lower than degradation temperatures of M and M'; M' is an atom of the first metal or the second metal; and n and p are each at least one, and the precursor is selected from the group consisting of Pt(triphenylphosphine)(Cl)-(μ-Cl₂)Ru(Cl)(trihapto:trihapto-2,7-dimethyloctadienediyl); {Pt₃[μ-bis(diphenylphosphino)methane]₃(Ru)(pentahapto-cyclopentadienyl)}[hexafluorophosphate]; [Ru(μ-2,3-bis(2-pyridyl)quinoxaline)PtCl₂)₃][tetrafluoroborate]₂; {Pt₃[μ-bis(diphenylphosphino)methane]₃(μ₃-Mo)(pentahapto-cyclopentadienyl)(CO)}[hexafluorophosphate]; {Pt₃[bis(diphenylphosphino)methane]₃(μ₃-Mo)(pentahapto-cyclopentadienyl)(CO)}[tetraphenylborate]; {Pt₃[μ-bis(diphenylphosphino)methane]₃[μ₄-Hg—Ru(pentahapto-cyclopentadienyl)(CO)₂]₂}[hexafluorophosphate]₂; [Ru(2,2'-bipyridine)₂(μ-bipyrimidine)PtCl₂][tetrafluoroborate]₂; Pt(dihaptoethylene)(Cl)(μ-Cl)₂Ru (Cl)(trihapto:trihapto-2,7-dimethyloctadienediyl); and {Pt₃(μ-W)(pentahapto-cyclopentadienyl) (CO)[μ-bis(diphenylphosphino)-methane]₃}[hexafluorophosphate].

7. A method of making a supported polymetallic nanoparticle, the method comprising (a) contacting a support with a polymetallic precursor comprising at least one first metal and at least one second metal and at least one metal-ligand-metal group represented by the formula:

$$M_n\text{—}X\text{—}M'_p,$$

wherein M is an atom of the first metal; X is a thermally degradable ligand having a degradation temperature lower than degradation temperatures of M and M' and X is selected from the group consisting of a single atom, compound or moiety having an atom selected from the group consisting of a halogen, a mercury atom, a phosphorus atom, an atom from Groups 14–17 of the Periodic Table; organic ligands selected from the group consisting of alkyl, alkenyl, alkynyl, aryl, aralkyl, alkylphosphino, arylphosphino, alkylsulfide, arylsulfide, alkylselenide, arylselenide, arlkylmercuric, and arylmercuric; ammonia; amine; alkene; heteroatomic aromatic molecules; arsenes; and derivatives thereof; M' is an atom of the first metal or the second metal; and n and p are each at least one; and (b) heating the contacted support in the substantial absence of an oxidizing agent to form a supported polymetallic nanoparticle comprising the first metal and the second metal at a selected atomic ratio, wherein the selected atomic ratio is approximately equal to a stoichiometric ratio of the first metal to the second metal in the polymetallic precursor.

8. The method according to claim 7, wherein step (b) further comprises heating the support in the presence of a hydrogen-containing gas reducing agent.

9. The method according to claim 7, wherein step (b) further comprises heating the support to a temperature greater than the degradation temperature of X.

10. The method according to claim 9, wherein step (b) further comprises thermally annealing the polymetallic nanoparticles by holding the support at that temperature for a period of time sufficient to form a crystalline structure.

11. The method according to claim 7, further comprising, after step (a):
(i) heating the contacted support in the presence of an oxidizing agent;
(ii) contacting the support after step (i) with the polymetallic precursor a second time;
(iii) heating the support after step (ii) a second time in the presence of an oxidizing agent; and
(iv) repeating steps (i) through (iii) at least once.

12. The method according to claim 7, further comprising, after step (a)
(i) heating the contacted support;
(ii) contacting the heated support after step (i) with the polymetallic precursor;
(iii) heating the support after step (ii) in the substantial absence of an oxidizing agent; and
(iv) repeating steps (i) through (iii) at least once.

13. The method according to claim 7, wherein the at least one first metal is platinum and the stoichiometric ratio of the first metal to the second metal is equal to at least about 1.

14. The method according to claim 7, wherein at least one of the first metal and the second metal is a noble metal.

15. The method according to claim 7, wherein step (a) further comprises contacting the support with a liquid composition comprising the precursor, wherein the composition is selected from the group consisting of a solution of the precursor and a suspension of the precursor.

16. The method according to claim 15, further comprising the step of substantially removing the liquid from the support prior to step (b).

17. The method according to claim 7, wherein the step (b) further comprises heating the support using microwave radiation.

18. The method according to claim 7, wherein step (b) further comprises controlling a rate of heating of the support, wherein the rate of heating is from about 10 to about 20° C./min.

19. The method according to claim 7, wherein the support is electrically conductive.

20. The method according to claim 19, wherein the support comprises particulate carbon having a mean particle diameter less than about 30 nanometers and a specific surface area of at least about 250 m²/g.

21. A supported nanocomposite comprising an electrically conductive support and a plurality of polymetallic nanoparticles, wherein the polymetallic nanoparticles comprise at least one first metal and at least one second metal and are formed from a polymetallic precursor comprising a metal-ligand-metal group represented by the formula

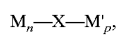

wherein M is an atom of the first metal; X is a thermally degradable ligand having a degradation temperature lower than degradation temperatures of M and M' and X is selected from the group consisting of a single atom, compound or moiety having an atom selected from the group consisting of a halogen, a mercury atom, a phosphorus atom, an atom from Groups 14–17 of the Periodic Table; organic ligands selected from the group consisting of alkyl, alkenyl, alkynyl, aryl, aralkyl, alkylphosphino, arylphosphino, alkylsulfide, arylsulfide, alkylselenide, arylselenide, arlkylmercuric, and arylmercuric; ammonia; amine; alkene; heteroatomic aromatic molecules; arsenes; and derivatives thereof; M' is an atom of the first metal or the second metal; and n and p are each at least one, and a stoichiometric ratio of the first metal atoms to the second metal atoms in the polymetallic precursor is approximately equal to a selected atomic ratio of the first metal atoms to the second metal atoms in the polymetallic nanoparticles.

22. The nanocomposite according to claim 21, wherein the nanoparticles have a mean diameter less than or equal to about twenty nanometers.

23. The composition according to claim 22, wherein the nanoparticles have a mean diameter less than or equal to about five nanometers.

24. A method for making a metallic nanocomposite, comprising
(a) contacting a support with a metallic precursor having at least one metal and at least one degradable ligand, wherein a degradation temperature of the at least one ligand is lower than a degradation temperature of the metal in the precursor;
(b) heating the contacted support in the substantial absence of an oxidizing agent by microwave radiation to degrade the at least one ligand and form a metallic nanocomposite.

25. The method according to claim 24, wherein the metallic precursor is a polymetallic precursor.

26. The method according to claim 24, further comprising after step (a) but before step (b):
(i) heating the precursor by microwave radiation in the presence of an oxidizing agent.

* * * * *

UNITED STATES PATENT AND TRADEMARK OFFICE
CERTIFICATE OF CORRECTION

| | | |
|---|---|---|
| PATENT NO. | : 6,232,264 B1 | Page 1 of 1 |
| APPLICATION NO. | : 09/099556 | |
| DATED | : June 18, 1998 | |
| INVENTOR(S) | : Lukehart et al. | |

It is certified that error appears in the above-identified patent and that said Letters Patent is hereby corrected as shown below:

Column 4, line 24,

"PtPb" should be -- PtPd --

Signed and Sealed this

Second Day of October, 2007

JON W. DUDAS
*Director of the United States Patent and Trademark Office*

UNITED STATES PATENT AND TRADEMARK OFFICE
CERTIFICATE OF CORRECTION

PATENT NO. : 6,232,264 B1 Page 1 of 1
APPLICATION NO. : 09/099556
DATED : May 15, 2001
INVENTOR(S) : Lukehart et al.

It is certified that error appears in the above-identified patent and that said Letters Patent is hereby corrected as shown below:

Column 4, line 24,

"PtPb" should be -- PtPd --

This certificate supersedes the Certificate of Correction issued October 2, 2007.

Signed and Sealed this

Fifteenth Day of January, 2008

JON W. DUDAS
*Director of the United States Patent and Trademark Office*